US011771821B2

(12) United States Patent
Damiano et al.

(10) Patent No.: US 11,771,821 B2
(45) Date of Patent: Oct. 3, 2023

(54) INFUSION SYSTEM AND COMPONENTS THEREOF

(71) Applicants: Trustees of Boston University, Boston, MA (US); Beta Bionics, Inc., Boston, MA (US)

(72) Inventors: Edward R. Damiano, Acton, MA (US); Rajendranath Selagamsetty, Boston, MA (US); Firas H. El-Khatib, Allston, MA (US); Bryan D. Knodel, Flaggstaff, AZ (US); Raymond A. Carr, Lutz, FL (US)

(73) Assignees: Trustees of Boston University, Boston, MA (US); Beta Bionics, Inc., Concord, MA (US)

( * ) Notice: Subject to any disclaimer, the term of this patent is extended or adjusted under 35 U.S.C. 154(b) by 419 days.

(21) Appl. No.: 17/110,497

(22) Filed: Dec. 3, 2020

(65) Prior Publication Data

US 2021/0106750 A1    Apr. 15, 2021

Related U.S. Application Data

(63) Continuation of application No. 16/503,269, filed on Jul. 3, 2019, now Pat. No. 10,857,287, which is a
(Continued)

(51) Int. Cl.
*A61M 37/00* (2006.01)
*A61M 5/14* (2006.01)
(Continued)

(52) U.S. Cl.
CPC ............ *A61M 5/1408* (2013.01); *A61J 1/201* (2015.05); *A61J 1/2065* (2015.05);
(Continued)

(58) Field of Classification Search
CPC ........... A61M 2005/14208; A61M 2039/1094; A61M 2205/276; A61M 2205/6045;
(Continued)

(56) References Cited

U.S. PATENT DOCUMENTS 1,930,929 A    10/1933  Eisenberg
3,807,467 A     4/1974  Tascher et al.
(Continued)

FOREIGN PATENT DOCUMENTS

CN    106061528 A    10/2016
EP      2678056 A2    1/2014
(Continued)

OTHER PUBLICATIONS

Boston University, Jan. 2014, Bionic Pancreas: Introducing the iLet 1294 1000, http://sites.bu.edu/bionicpacreas/introducing-the-ilet-1294-1000/, 3 pp.
(Continued)

*Primary Examiner* — Rebecca E Eisenberg
(74) *Attorney, Agent, or Firm* — BainwoodHuang

(57) ABSTRACT

Multi-medicament infusion systems prevent cross-channeling of medicaments. A system may include one or more of an infusion pump, medicament reservoirs, a multi-channel fluid conduit, and an infusion set. Medicament reservoirs and/or collars may be sized and shaped differently such that the medicament reservoirs can only be inserted into the system under selected configurations.

16 Claims, 33 Drawing Sheets

Related U.S. Application Data continuation of application No. PCT/US2018/012636, filed on Jan. 5, 2018.

(60) Provisional application No. 62/444,244, filed on Jan. 9, 2017, provisional application No. 62/443,616, filed on Jan. 6, 2017.

(51) Int. Cl.
   *A61J 1/20* (2006.01)
   *A61M 5/168* (2006.01)
   *A61J 1/14* (2023.01)

(52) U.S. Cl.
   CPC .......... *A61M 5/1684* (2013.01); *A61J 1/1406* (2013.01); *A61J 1/1481* (2015.05); *A61J 1/2037* (2015.05); *A61J 1/2096* (2013.01); *A61J 2200/70* (2013.01); *A61J 2205/10* (2013.01); *A61J 2205/60* (2013.01)

(58) Field of Classification Search
   CPC ...... A61M 5/1413; A61M 5/162; A61J 1/201; A61J 1/2065; A61J 1/1481; A61J 1/2037; A61J 1/1406; A61J 1/2096
   See application file for complete search history.

(56) References Cited

U.S. PATENT DOCUMENTS

| | | |
|---|---|---|
| 4,150,673 A | 4/1979 | Watt |
| 4,253,501 A | 3/1981 | Ogle |
| 4,515,584 A | 5/1985 | Abe et al. |
| 4,585,439 A | 4/1986 | Michel |
| 4,608,042 A | 8/1986 | Vanderveen et al. |
| 4,675,006 A | 6/1987 | Hrushesky |
| 5,085,643 A | 2/1992 | Larkin et al. |
| 5,243,982 A | 9/1993 | Mostl |
| 5,298,023 A | 3/1994 | Haber |
| 5,356,380 A | 10/1994 | Hoekwater et al. |
| 5,411,480 A | 5/1995 | Kriesel |
| 5,472,403 A | 12/1995 | Cornacchia |
| 5,505,704 A | 4/1996 | Pawelka et al. |
| 5,522,803 A | 6/1996 | Teissen-Simony |
| 5,545,152 A | 8/1996 | Funderburk et al. |
| 5,616,124 A | 4/1997 | Hague et al. |
| 5,916,494 A | 6/1999 | Widman et al. |
| 5,954,697 A | 9/1999 | Srisathapat et al. |
| 5,961,494 A | 10/1999 | Hogan |
| 5,971,972 A | 10/1999 | Rosenbaum |
| 6,106,498 A | 8/2000 | Friedli et al. |
| 6,132,416 A | 10/2000 | Broselow |
| 6,248,067 B1 | 6/2001 | Causey, III et al. |
| 6,259,587 B1 | 7/2001 | Sheldon et al. |
| 6,360,784 B1 | 3/2002 | Philippens et al. |
| 6,362,591 B1 | 3/2002 | Moberg |
| 6,368,314 B1 | 4/2002 | Kipfer et al. |
| 6,390,130 B1 | 5/2002 | Guala |
| 6,485,465 B2 | 11/2002 | Moberg et al. |
| 6,551,276 B1 | 4/2003 | Mann et al. |
| 6,551,298 B1 | 4/2003 | Zhang et al. |
| 6,554,798 B1 | 4/2003 | Mann et al. |
| 6,555,986 B2 | 4/2003 | Moberg |
| 6,558,320 B1 | 5/2003 | Causey, III et al. |
| 6,572,545 B2 | 6/2003 | Knobbe et al. |
| 6,585,695 B1 | 7/2003 | Adair et al. |
| 6,620,138 B1 | 9/2003 | Marrgi et al. |
| 6,641,533 B2 | 11/2003 | Causey, III et al. |
| 6,652,483 B2 | 11/2003 | Slate |
| 6,656,148 B2 | 12/2003 | Das et al. |
| 6,659,980 B2 | 12/2003 | Moberg et al. |
| 6,719,728 B2 | 4/2004 | Mason et al. |
| 6,736,797 B1 | 5/2004 | Larsen et al. |
| 6,752,787 B1 | 6/2004 | Causey, III et al. |
| 6,801,420 B2 | 10/2004 | Talbot et al. |
| 6,809,653 B1 | 10/2004 | Mann et al. |
| 6,811,534 B2 | 11/2004 | Bowman et al. |
| 6,821,421 B2 | 11/2004 | Murakami |
| 6,854,620 B2 | 2/2005 | Ramey |
| 6,872,200 B2 | 3/2005 | Mann et al. |
| 6,878,132 B2 | 4/2005 | Kipfer |
| 6,936,029 B2 | 8/2005 | Mann et al. |
| 6,939,329 B1 | 9/2005 | Verkaart |
| 6,958,705 B2 | 10/2005 | Lebel et al. |
| 6,960,198 B2 | 11/2005 | Sarmiento |
| 6,979,326 B2 | 12/2005 | Mann et al. |
| 6,997,920 B2 | 2/2006 | Mann et al. |
| 7,025,226 B2 | 4/2006 | Ramey |
| 7,025,743 B2 | 4/2006 | Mann et al. |
| 7,098,803 B2 | 8/2006 | Mann et al. |
| 7,109,878 B2 | 9/2006 | Mann et al. |
| 7,187,528 B2 | 3/2007 | Talbot et al. |
| 7,193,521 B2 | 3/2007 | Moberg et al. |
| 7,281,314 B2 | 10/2007 | Hess et al. |
| 7,285,105 B2 | 10/2007 | Kim et al. |
| 7,291,133 B1 | 11/2007 | Kindler et al. |
| 7,324,012 B2 | 1/2008 | Mann et al. |
| 7,342,508 B2 | 3/2008 | Morgan et al. |
| 7,460,350 B2 | 12/2008 | Talbot et al. |
| 7,534,226 B2 | 5/2009 | Mernoe et al. |
| 7,602,310 B2 | 10/2009 | Mann et al. |
| 7,621,893 B2 | 11/2009 | Moberg et al. |
| 7,625,354 B2 | 12/2009 | Hochman |
| 7,628,772 B2 | 12/2009 | McConnell et al. |
| 7,628,782 B2 | 12/2009 | Adair et al. |
| 7,648,494 B2 | 1/2010 | Kornerup et al. |
| 7,654,127 B2 | 2/2010 | Krulevitch et al. |
| 7,655,618 B2 | 2/2010 | Green et al. |
| 7,658,734 B2 | 2/2010 | Adair et al. |
| 7,678,762 B2 | 3/2010 | Green et al. |
| 7,678,763 B2 | 3/2010 | Green et al. |
| 7,683,027 B2 | 3/2010 | Green et al. |
| 7,708,717 B2 | 5/2010 | Estes et al. |
| 7,760,481 B2 | 7/2010 | Talbot et al. |
| 7,766,873 B2 | 8/2010 | Moberg et al. |
| 7,776,030 B2 | 8/2010 | Estes et al. |
| 7,789,859 B2 | 9/2010 | Estes et al. |
| 7,794,427 B2 | 9/2010 | Estes et al. |
| 7,794,428 B2 | 9/2010 | Estes et al. |
| 7,815,602 B2 | 10/2010 | Mann et al. |
| 7,819,843 B2 | 10/2010 | Mann et al. |
| 7,831,310 B2 | 11/2010 | Lebel et al. |
| 7,833,196 B2 | 11/2010 | Estes et al. |
| 7,879,010 B2 | 2/2011 | Hunn et al. |
| 7,879,026 B2 | 2/2011 | Estes et al. |
| 7,887,512 B2 | 2/2011 | Estes et al. |
| 7,892,206 B2 | 2/2011 | Moberg et al. |
| 7,914,449 B2 | 3/2011 | Kouchi et al. |
| 7,922,708 B2 | 4/2011 | Estes et al. |
| 7,951,112 B2 | 5/2011 | Patzer |
| 7,967,785 B2 | 6/2011 | Morgan et al. |
| 7,981,084 B2 | 7/2011 | Estes et al. |
| 7,981,105 B2 | 7/2011 | Adair et al. |
| 7,988,683 B2 | 8/2011 | Adair et al. |
| 7,998,111 B2 | 8/2011 | Moberg et al. |
| 7,998,131 B2 | 8/2011 | Adair et al. |
| 8,004,422 B2 | 8/2011 | Hess et al. |
| 7,938,803 B2 | 10/2011 | Mernoe et al. |
| 8,034,026 B2 | 10/2011 | Grant et al. |
| 8,057,436 B2 | 11/2011 | Causey et al. |
| 8,062,257 B2 | 11/2011 | Moberg et al. |
| 8,065,096 B2 | 11/2011 | Moberg et al. |
| 8,088,096 B2 | 1/2012 | Lauchard et al. |
| 8,105,279 B2 | 1/2012 | Mernoe et al. |
| 8,106,534 B2 | 1/2012 | Spurlin et al. |
| 8,142,397 B2 | 3/2012 | Patzer |
| 8,167,846 B2 | 5/2012 | Chong et al. |
| 8,177,767 B2 | 5/2012 | Kristensen et al. |
| 8,182,447 B2 | 5/2012 | Moberg et al. |
| 8,192,394 B2 | 6/2012 | Estes et al. |
| 8,197,444 B1 | 6/2012 | Bazargan et al. |
| 8,206,350 B2 | 6/2012 | Mann et al. |
| 8,206,353 B2 | 6/2012 | Chong et al. |
| 8,211,059 B2 | 7/2012 | Kriesel et al. |
| 8,211,062 B2 | 7/2012 | Estes et al. |

(56) References Cited

U.S. PATENT DOCUMENTS

| | | |
|---|---|---|
| 8,251,959 B2 | 8/2012 | Johner et al. |
| 8,257,345 B2 | 9/2012 | Adair et al. |
| 8,267,893 B2 | 9/2012 | Moberg et al. |
| 8,273,061 B2 | 9/2012 | McConnell et al. |
| 8,282,601 B2 | 10/2012 | Mernoe et al. |
| 8,287,495 B2 | 10/2012 | Michaud et al. |
| 8,287,516 B2 | 10/2012 | Kornerup et al. |
| 8,298,184 B2 | 10/2012 | Diperna et al. |
| 8,303,572 B2 | 11/2012 | Adair et al. |
| 8,372,039 B2 | 2/2013 | Mernoe et al. |
| 8,409,142 B2 | 4/2013 | Causey et al. |
| 8,430,847 B2 | 4/2013 | Mernoe et al. |
| 8,430,849 B2 | 4/2013 | Smith et al. |
| 8,454,575 B2 | 6/2013 | Estes et al. |
| 8,469,942 B2 | 6/2013 | Kow et al. |
| 8,475,408 B2 | 7/2013 | Mernoe et al. |
| 8,480,623 B2 | 7/2013 | Mernoe et al. |
| 8,483,980 B2 | 7/2013 | Moberg et al. |
| 8,500,716 B2 | 8/2013 | Adair et al. |
| 8,512,276 B2 | 8/2013 | Talbot et al. |
| 8,512,289 B2 | 8/2013 | Chong et al. |
| 8,523,803 B1 | 9/2013 | Favreau |
| 8,551,045 B2 | 10/2013 | Sie et al. |
| 8,551,046 B2 | 10/2013 | Causey et al. |
| 8,556,856 B2 | 10/2013 | Bazargan et al. |
| 8,556,866 B2 | 10/2013 | Krulevitch et al. |
| 8,562,565 B2 | 10/2013 | Fonacier et al. |
| 8,562,587 B2 | 10/2013 | Kovatchev et al. |
| 8,568,349 B2 | 10/2013 | Shergold |
| 8,573,027 B2 | 11/2013 | Rosinko et al. |
| 8,579,813 B2 | 11/2013 | Causey, III et al. |
| 8,597,269 B2 | 12/2013 | Chong et al. |
| 8,603,026 B2 | 12/2013 | Favreau |
| 8,603,027 B2 | 12/2013 | Favreau |
| 8,603,033 B2 | 12/2013 | Bazargan et al. |
| 8,613,726 B2 | 12/2013 | Causey, III et al. |
| 8,613,731 B2 | 12/2013 | Hansen et al. |
| 8,617,110 B2 | 12/2013 | Moberg et al. |
| 8,622,966 B2 | 1/2014 | Causey, III et al. |
| 8,628,510 B2 | 1/2014 | Bazargan et al. |
| 8,641,671 B2 | 2/2014 | Michaud et al. |
| 8,647,074 B2 | 2/2014 | Moberg et al. |
| 8,647,296 B2 | 2/2014 | Moberg et al. |
| 8,663,103 B2 | 3/2014 | Causey, III et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,696,633 B2 | 4/2014 | Estes et al. |
| 8,747,368 B2 | 6/2014 | Mernoe et al. |
| 8,747,369 B2 | 6/2014 | Mernoe et al. |
| 8,758,323 B2 | 6/2014 | Michaud et al. |
| 8,771,229 B2 | 7/2014 | Amirouche et al. |
| 8,777,901 B2 | 7/2014 | Smith et al. |
| 8,790,307 B2 | 7/2014 | Amirouche et al. |
| 8,821,442 B2 | 9/2014 | Haaar |
| 8,823,528 B2 | 9/2014 | Blomquist |
| 8,834,420 B2 | 9/2014 | Estes et al. |
| 8,841,012 B2 | 9/2014 | Fonacier et al. |
| 8,864,726 B2 | 10/2014 | Halili et al. |
| 8,864,737 B2 | 10/2014 | Hasegawa et al. |
| 8,864,739 B2 | 10/2014 | Moberg et al. |
| 8,870,829 B2 | 10/2014 | Halili et al. |
| 8,876,770 B2 | 11/2014 | Kraft et al. |
| 8,900,206 B2 | 12/2014 | Halili et al. |
| 8,905,972 B2 | 12/2014 | Smith et al. |
| 8,915,879 B2 | 12/2014 | Smith et al. |
| 8,936,573 B2 | 1/2015 | Blomquist |
| 8,945,068 B2 | 2/2015 | Halili et al. |
| 8,974,435 B2 | 3/2015 | Friedli |
| 8,992,475 B2 | 3/2015 | Mann et al. |
| 8,992,507 B2 | 3/2015 | Aeschlimann et al. |
| 8,998,840 B2 | 4/2015 | Hanson et al. |
| 8,998,842 B2 | 4/2015 | Lauchard et al. |
| 8,998,858 B2 | 4/2015 | Chong et al. |
| 9,011,371 B2 | 4/2015 | Moberg et al. |
| 9,033,925 B2 | 5/2015 | Moberg et al. |
| 9,033,951 B2 | 5/2015 | Kow et al. |
| 9,050,406 B2 | 6/2015 | Kow et al. |
| 9,101,710 B2 | 8/2015 | Yavorsky et al. |
| 9,101,715 B2 | 8/2015 | Causey, III et al. |
| 9,107,999 B2 | 8/2015 | Moberg et al. |
| 9,114,209 B2 | 8/2015 | Estes et al. |
| 9,114,213 B2 | 8/2015 | Murakami et al. |
| 9,119,917 B2 | 9/2015 | Blomquist |
| 9,132,228 B2 | 9/2015 | Yan |
| 9,173,998 B2 | 11/2015 | Rosinko et al. |
| 9,180,242 B2 | 11/2015 | Metzmaker et al. |
| 9,180,243 B2 | 11/2015 | Michaud |
| 9,180,254 B2 | 11/2015 | Avery et al. |
| 9,184,490 B2 | 11/2015 | Crouther et al. |
| 9,194,388 B2 | 11/2015 | Laermer |
| 9,205,192 B2 | 12/2015 | Estes et al. |
| 9,211,376 B2 | 12/2015 | Kouyoumjian et al. |
| 9,211,377 B2 | 12/2015 | Diperna et al. |
| 9,216,249 B2 | 12/2015 | Smith et al. |
| 9,220,835 B2 | 12/2015 | Cane' |
| 9,250,106 B2 | 2/2016 | Rosinko et al. |
| 9,272,009 B2 | 3/2016 | Spencer |
| 9,283,318 B2 | 3/2016 | Yavorsky et al. |
| 9,295,826 B2 | 3/2016 | Bertrand et al. |
| 9,308,320 B2 | 4/2016 | Smith et al. |
| 9,308,321 B2 | 4/2016 | Alderete et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,335,910 B2 | 5/2016 | Farnan et al. |
| 9,339,639 B2 | 5/2016 | Halili et al. |
| 9,344,024 B2 | 5/2016 | Favreau |
| 9,345,643 B2 | 5/2016 | Okiyama |
| 9,364,608 B2 | 6/2016 | Moberg et al. |
| 9,379,652 B2 | 6/2016 | Favreau |
| 9,379,653 B2 | 6/2016 | Favreau |
| 9,381,297 B2 | 7/2016 | Brown et al. |
| 9,381,300 B2 | 7/2016 | Smith et al. |
| 9,393,399 B2 | 7/2016 | Yavorsky et al. |
| 9,415,157 B2 | 8/2016 | Mann et al. |
| 9,427,519 B2 | 8/2016 | Kraft et al. |
| 9,433,731 B2 | 9/2016 | Track et al. |
| 9,433,732 B2 | 9/2016 | Moberg et al. |
| 9,433,733 B2 | 9/2016 | Moberg et al. |
| 9,452,255 B2 | 9/2016 | Tieck et al. |
| 9,452,256 B2 | 9/2016 | Tieck et al. |
| 9,463,309 B2 | 10/2016 | Yavorsky et al. |
| 9,494,147 B2 | 11/2016 | Chong et al. |
| 9,498,573 B2 | 11/2016 | Smith et al. |
| 9,514,518 B2 | 12/2016 | Gillespie et al. |
| 9,517,299 B2 | 12/2016 | Tieck et al. |
| 9,517,301 B2 | 12/2016 | Estes et al. |
| 9,533,132 B2 | 1/2017 | Halili et al. |
| 9,539,385 B2 | 1/2017 | Mathys |
| 9,539,388 B2 | 1/2017 | Causey et al. |
| 9,554,967 B2 | 1/2017 | Moia et al. |
| 9,579,452 B2 | 2/2017 | Adair et al. |
| 9,592,339 B2 | 3/2017 | Zhou |
| 9,597,462 B2 | 3/2017 | Moore |
| 9,610,431 B2 | 4/2017 | Halili et al. |
| 9,629,992 B2 | 4/2017 | Halili et al. |
| 9,636,453 B2 | 5/2017 | Monirabbasi et al. |
| 9,682,189 B2 | 6/2017 | Good et al. |
| 9,687,612 B2 | 6/2017 | Avery et al. |
| 9,715,327 B2 | 7/2017 | Rosinko et al. |
| 9,717,845 B2 | 8/2017 | Istoc |
| 9,717,848 B2 | 8/2017 | Geismar et al. |
| 9,731,067 B2 | 8/2017 | Pananen |
| 9,744,290 B2 | 8/2017 | Tieck et al. |
| 9,744,291 B2 | 8/2017 | Tieck et al. |
| 9,744,301 B2 | 8/2017 | Mann et al. |
| 9,750,871 B2 | 9/2017 | Metzmaker et al. |
| 9,750,873 B2 | 9/2017 | Brown et al. |
| 9,750,875 B2 | 9/2017 | Smith et al. |
| 9,770,553 B2 | 9/2017 | Bazargan et al. |
| 9,782,543 B2 | 10/2017 | Groeschke et al. |
| 9,789,245 B2 | 10/2017 | Tieck et al. |
| 9,795,732 B2 | 10/2017 | Trock et al. |

(56) References Cited

U.S. PATENT DOCUMENTS

| | | |
|---|---|---|
| 9,801,787 B2 | 10/2017 | Py |
| 9,814,830 B2 | 11/2017 | Mernoe et al. |
| 9,814,872 B2 | 11/2017 | Eggert et al. |
| 9,839,741 B2 | 12/2017 | Yavorsky et al. |
| 9,841,014 B2 | 12/2017 | Yap et al. |
| 9,863,837 B2 | 1/2018 | Rule et al. |
| 9,872,957 B2 | 1/2018 | Causey et al. |
| 9,883,834 B2 | 2/2018 | Amirouche et al. |
| 9,889,256 B2 | 2/2018 | Cabiri et al. |
| 9,895,490 B2 | 2/2018 | Kow et al. |
| 9,925,330 B2 | 3/2018 | Tieck et al. |
| 9,931,459 B2 | 4/2018 | Tieck et al. |
| 9,931,460 B2 | 4/2018 | Tieck et al. |
| 9,943,645 B2 | 4/2018 | Monirabbasi et al. |
| 9,950,113 B2 | 4/2018 | Franke et al. |
| 9,987,420 B2 | 6/2018 | Pananen |
| 9,993,592 B2 | 6/2018 | Amirouche et al. |
| 9,993,594 B2 | 6/2018 | Bazargan et al. |
| 10,010,674 B2 | 7/2018 | Rosinko et al. |
| 10,010,678 B2 | 7/2018 | Schildt et al. |
| 10,016,564 B2 | 7/2018 | Piehl et al. |
| 10,029,045 B2 | 7/2018 | Smith et al. |
| 10,064,993 B2 | 9/2018 | Mernoe et al. |
| 10,071,200 B2 | 9/2018 | Alderete et al. |
| 10,080,839 B2 | 9/2018 | Cole et al. |
| 10,086,133 B2 | 10/2018 | Pananen et al. |
| 10,086,134 B2 | 10/2018 | Pananen et al. |
| 10,092,701 B2 | 10/2018 | Johansen et al. |
| 10,105,483 B2 | 10/2018 | Mernoe |
| 10,105,497 B2 | 10/2018 | Dreier et al. |
| 10,130,759 B2 | 11/2018 | Amirouche et al. |
| 10,130,763 B2 | 11/2018 | Lauchard et al. |
| 10,137,243 B2 | 11/2018 | Wang et al. |
| 10,141,882 B2 | 11/2018 | Favreau |
| 10,146,911 B2 | 12/2018 | Trock |
| 10,166,327 B2 | 1/2019 | Tieck et al. |
| 10,172,998 B2 | 1/2019 | Tieck et al. |
| 10,172,999 B2 | 1/2019 | Tieck et al. |
| 10,207,047 B2 | 2/2019 | Estes |
| 10,213,549 B2 | 2/2019 | Amirouche et al. |
| 10,220,143 B2 | 3/2019 | Moberg et al. |
| 10,228,663 B2 | 3/2019 | Favreau |
| 10,232,109 B2 | 3/2019 | Deak et al. |
| 10,238,030 B2 | 3/2019 | Urbani |
| 10,238,793 B2 | 3/2019 | Deak et al. |
| 10,252,001 B2 | 4/2019 | Geismar et al. |
| 10,258,736 B2 | 4/2019 | Metzmaker et al. |
| 10,272,196 B2 | 4/2019 | Smith et al. |
| 10,279,110 B2 | 5/2019 | Mann et al. |
| 10,300,264 B2 | 5/2019 | Halili et al. |
| 10,307,536 B2 | 6/2019 | Causey et al. |
| 10,322,227 B2 | 6/2019 | Piehl et al. |
| 10,363,365 B2 | 7/2019 | Bazargan |
| 10,376,631 B2 | 8/2019 | Tieck et al. |
| 10,376,632 B2 | 8/2019 | Tieck et al. |
| 10,384,013 B2 | 8/2019 | Krusell et al. |
| 10,391,257 B2 | 8/2019 | Piehl et al. |
| 10,478,554 B2 | 11/2019 | Bazargan et al. |
| 10,517,892 B2 | 12/2019 | Chattaraj et al. |
| 10,532,156 B2 | 1/2020 | Istoc |
| 10,552,580 B2 | 2/2020 | Bazargan |
| 10,603,431 B2 | 3/2020 | Mernoe et al. |
| 10,772,796 B2 | 9/2020 | Kavazov |
| 10,850,032 B2 | 12/2020 | Steck et al. |
| 10,857,287 B2 | 12/2020 | Damiano et al. |
| 10,861,591 B2 | 12/2020 | Grosman et al. |
| 10,960,136 B2 | 3/2021 | Palerm et al. |
| 2002/0019608 A1 | 2/2002 | Mason et al. |
| 2002/0038392 A1 | 3/2002 | De La Huerga |
| 2002/0055711 A1 | 5/2002 | Lavi et al. |
| 2002/0065484 A1 | 5/2002 | Douglas et al. |
| 2002/0161332 A1 | 10/2002 | Ramey |
| 2003/0009133 A1 | 1/2003 | Ramey |
| 2005/0015056 A1 | 1/2005 | Duchon et al. |
| 2005/0020980 A1 | 1/2005 | Inoue |
| 2005/0038387 A1 | 2/2005 | Kriesel |
| 2005/0051580 A1 | 3/2005 | Ramey |
| 2005/0154434 A1 | 7/2005 | Simon et al. |
| 2005/0215979 A1 | 9/2005 | Kornerup et al. |
| 2006/0102174 A1 | 5/2006 | Hochman |
| 2006/0264908 A1 | 11/2006 | Ishii et al. |
| 2007/0088271 A1 | 4/2007 | Richards |
| 2007/0142786 A1 | 6/2007 | Lampropoulos et al. |
| 2007/0161955 A1 | 7/2007 | Bynum et al. |
| 2007/0273671 A1 | 11/2007 | Zadesky et al. |
| 2007/0282294 A1 | 12/2007 | Sidler |
| 2008/0051719 A1 | 2/2008 | Nair et al. |
| 2008/0119792 A1 | 5/2008 | Kornerup et al. |
| 2008/0188813 A1 | 8/2008 | Miller et al. |
| 2008/0243085 A1 | 10/2008 | DeStefano |
| 2008/0262425 A1 | 10/2008 | Mogensen |
| 2008/0319383 A1 | 12/2008 | Byland |
| 2009/0099523 A1 | 4/2009 | Grant et al. |
| 2009/0281505 A1 | 11/2009 | Hansen et al. |
| 2009/0326506 A1 | 12/2009 | Hasegawa et al. |
| 2010/0004603 A1 | 1/2010 | Kristensen et al. |
| 2010/0049144 A1 | 2/2010 | McConnell et al. |
| 2010/0191165 A1 | 7/2010 | Appling et al. |
| 2010/0217241 A1 | 8/2010 | Mann et al. |
| 2011/0021905 A1 | 1/2011 | Patrick et al. |
| 2011/0118659 A1 | 5/2011 | Maaskamp |
| 2011/0230838 A1 | 9/2011 | Adams et al. |
| 2011/0288494 A1 | 11/2011 | Mendels |
| 2012/0078170 A1 | 3/2012 | Smith et al. |
| 2012/0078185 A1 | 3/2012 | Smith et al. |
| 2012/0078197 A1 | 5/2012 | O'Connor et al. |
| 2012/0211946 A1 | 8/2012 | Halili et al. |
| 2012/0211947 A1 | 8/2012 | Halili et al. |
| 2012/0215177 A1 | 8/2012 | Halili et al. |
| 2012/0215178 A1 | 8/2012 | Halili et al. |
| 2012/0215179 A1 | 8/2012 | Halili et al. |
| 2012/0215180 A1 | 8/2012 | Halili et al. |
| 2012/0215183 A1 | 8/2012 | Halili et al. |
| 2012/0226234 A1 | 9/2012 | Bazargan et al. |
| 2012/0323188 A1 | 12/2012 | Yavorsky et al. |
| 2013/0046252 A1 | 2/2013 | Yavorsky et al. |
| 2013/0046253 A1 | 2/2013 | Yavorsky et al. |
| 2013/0066281 A1 | 3/2013 | Yavorsky et al. |
| 2013/0085470 A1 | 4/2013 | O'Connor et al. |
| 2013/0090602 A1 | 4/2013 | Avery et al. |
| 2013/0116632 A1 | 5/2013 | Yavorsky et al. |
| 2013/0183170 A1 | 7/2013 | Laermer |
| 2013/0237947 A1 | 9/2013 | Amirouche et al. |
| 2013/0245604 A1 | 9/2013 | Kouyoumjian et al. |
| 2013/0274576 A1 | 10/2013 | Amirouche et al. |
| 2013/0345641 A1 | 12/2013 | German |
| 2014/0052079 A1 | 2/2014 | Eggert et al. |
| 2014/0194815 A1 | 7/2014 | Kouyoumjian et al. |
| 2014/0276563 A1 | 9/2014 | Cole et al. |
| 2014/0378912 A1 | 12/2014 | Halili et al. |
| 2014/0378913 A1 | 12/2014 | Halili et al. |
| 2015/0045735 A1 | 2/2015 | Halili et al. |
| 2015/0057615 A1 | 2/2015 | Mernoe et al. |
| 2015/0073384 A1 | 3/2015 | Limaye |
| 2015/0202375 A1 | 7/2015 | Schabbach et al. |
| 2015/0265826 A1 | 9/2015 | Dudley |
| 2015/0314063 A1 | 11/2015 | Nagar et al. |
| 2015/0357683 A1 | 12/2015 | Lohr |
| 2016/0015885 A1 | 1/2016 | Pananen et al. |
| 2016/0015886 A1 | 1/2016 | Pananen et al. |
| 2016/0015887 A1 | 1/2016 | Pananen et al. |
| 2016/0015911 A1 | 1/2016 | Bazargan et al. |
| 2016/0051760 A1 | 2/2016 | Krusell et al. |
| 2016/0058668 A1 | 3/2016 | Metzmaker et al. |
| 2016/0074587 A1 | 3/2016 | Searle et al. |
| 2016/0082182 A1 | 3/2016 | Gregory et al. |
| 2016/0089493 A1 | 3/2016 | Crouther et al. |
| 2016/0106919 A1 | 4/2016 | Hayter et al. |
| 2016/0151563 A1 | 6/2016 | Yavorsky et al. |
| 2016/0184519 A1 | 6/2016 | Blundred et al. |
| 2016/0023591 A1 | 8/2016 | Damiano et al. |
| 2016/0220754 A1 | 8/2016 | Shaanan et al. |
| 2016/0263324 A1 | 9/2016 | Shaanan et al. |
| 2016/0271322 A1 | 9/2016 | Ramey |

(56) References Cited

U.S. PATENT DOCUMENTS

| | | |
|---|---|---|
| 2016/0361494 A1 | 12/2016 | Jurg et al. |
| 2017/0056590 A1 | 3/2017 | Diperna et al. |
| 2017/0065768 A1 | 3/2017 | Moore |
| 2017/0182307 A1 | 6/2017 | Halili et al. |
| 2017/0189666 A1 | 7/2017 | Sealfon et al. |
| 2017/0192506 A1 | 7/2017 | Andersen et al. |
| 2017/0216523 A1 | 8/2017 | Neftel et al. |
| 2017/0232203 A1 | 8/2017 | Krusell |
| 2017/0235920 A1 | 8/2017 | Bauss et al. |
| 2017/0239422 A1 | 8/2017 | Kodgule et al. |
| 2017/0286638 A1 | 10/2017 | Searle et al. |
| 2017/0312454 A1 | 11/2017 | Chattaraj et al. |
| 2018/0036475 A1 | 2/2018 | Lin |
| 2018/0043104 A1 | 2/2018 | Mueller-Pathle |
| 2018/0043105 A1 | 2/2018 | Nazzaro et al. |
| 2018/0103897 A1 | 4/2018 | Amirouche |
| 2018/0104417 A1 | 4/2018 | Nessel et al. |
| 2018/0117248 A1 | 6/2018 | Cabiri et al. |
| 2018/0117296 A1 | 6/2018 | Damiano et al. |
| 2018/0207366 A1 | 7/2018 | Marcoz et al. |
| 2018/0228979 A1 | 8/2018 | Schildt et al. |
| 2018/0280624 A1 | 10/2018 | Bitton et al. |
| 2018/0311435 A1 | 11/2018 | Galasso |
| 2018/0318498 A1 | 11/2018 | Grant et al. |
| 2018/0318506 A1 | 11/2018 | Oakes et al. |
| 2018/0326164 A1 | 11/2018 | Bauss et al. |
| 2018/0353699 A1 | 12/2018 | Helmer et al. |
| 2019/0001060 A1 | 1/2019 | Gylleby et al. |
| 2019/0009032 A1 | 1/2019 | Hautaviita et al. |
| 2019/0015582 A1 | 1/2019 | Naftalovitz et al. |
| 2019/0030247 A1 | 1/2019 | Edwards et al. |
| 2019/0054251 A1 | 2/2019 | Pieronek et al. |
| 2019/0091460 A1 | 3/2019 | Yavorsky et al. |
| 2019/0134305 A1 | 5/2019 | Srinivasan et al. |
| 2019/0151559 A1 | 5/2019 | Byerly et al. |
| 2019/0167900 A1 | 6/2019 | Friedli et al. |
| 2019/0192762 A1 | 6/2019 | Metzmaker et al. |
| 2019/0209775 A1 | 7/2019 | Merchant |
| 2019/0217007 A1 | 7/2019 | Sasaki |
| 2019/0344009 A1 | 11/2019 | Damiano et al. |
| 2020/0330719 A1 | 10/2020 | Segal |
| 2021/0030949 A1 | 2/2021 | Damiano et al. |
| 2021/0030957 A1 | 2/2021 | Beckstein et al. |
| 2021/0093777 A1 | 4/2021 | Damiano et al. |

FOREIGN PATENT DOCUMENTS

| | | | |
|---|---|---|---|
| EP | 3060276 A1 | 8/2016 | |
| EP | 3060277 A1 | 8/2016 | |
| EP | 3062841 A1 | 9/2016 | |
| EP | 3150241 B1 | 6/2018 | |
| EP | 3378516 A1 | 9/2018 | |
| EP | 3319662 A1 | 3/2019 | |
| GB | 2059776 A * | 4/1981 | .......... A61M 5/1408 |
| HK | 1230529 | 12/2017 | |
| HK | 1254602 A | 7/2019 | |
| JP | 5930241 | 2/1984 | |
| JP | 2016538098 A | 8/2016 | |
| JP | 2018525060 A | 9/2018 | |
| RU | 2549310 | 4/2015 | |
| WO | WO 99/64103 A1 | 12/1999 | |
| WO | 03017915 | 3/2003 | |
| WO | WO 2004/045704 A2 | 6/2004 | |
| WO | 05000378 | 1/2005 | |
| WO | WO 2005/004973 A1 | 1/2005 | |
| WO | WO 2006/054367 A1 | 5/2006 | |
| WO | WO 2009/069511 A1 | 4/2009 | |
| WO | WO 2007/086186 A1 | 5/2009 | |
| WO | WO 2009/060741 A1 | 5/2009 | |
| WO | 11131778 | 10/2011 | |
| WO | WO 2012/008285 A1 | 1/2012 | |
| WO | WO 2012/072555 A1 | 6/2012 | |
| WO | WO 2012/110474 A1 | 8/2012 | |
| WO | WO 2012/0115911 A2 | 8/2012 | |
| WO | 12146670 | 11/2012 | |
| WO | WO 2012/160104 A2 | 11/2012 | |
| WO | WO 2013/161979 A1 | 10/2013 | |
| WO | WO 2014/104027 A1 | 3/2014 | |
| WO | WO 2015/061690 A1 | 4/2015 | |
| WO | WO 2015/061691 A1 | 4/2015 | |
| WO | WO 2015/061693 A1 | 4/2015 | |
| WO | WO 2015/155229 A1 | 10/2015 | |
| WO | WO 2015/166993 A1 | 11/2015 | |
| WO | WO 2017/007968 A1 | 1/2017 | |
| WO | WO 2017/199012 A1 | 11/2017 | |
| WO | WO 2017/217105 A1 | 12/2017 | |
| WO | WO 2018/129354 A1 | 7/2018 | |
| WO | WO 2019/021985 A1 | 1/2019 | |
| WO | WO 2019/046593 A1 | 3/2019 | |

OTHER PUBLICATIONS

Brown et al., Apr. 1, 2016, Introducing Beta Bionics: bringing the iLet bionic pancreas to market, https://diatribe.org/introducing-beta-bionics-bringing-ilet-bionic-pancreas-marekt, 3 pp.

Hoskins, Oct. 2, 2018, iLet "Bionic Pancreas" making progress with gen 4 device, Healthline, https"//www.healthline.com/diabetesmine/beta-bionics-ilet-update#1, 15 pp.

Idlebrook, Jul. 30, 2019, Beta Bionics secures funding for pivotal iLet bionic pancreas trials, https://t1dexchange.org/welcome-glu-users/articles/beta-bionics-secures-funding-for-pivotal-ilet-bionic-pancreas-trials, 4 pp.

Krugman, Aug. 25, 2018, iLet Bionic Pancreas Interface, sarakrugman.com/ilet-interface, 3 pp.

Sifferlin, Apr. 1, 2016, The bionic pancreas is getting closer to reality, time.com, https://time.com/4278068/bionic-pancreas-company, 5 pp.

International Search Report and Written Opinion in PCT/US18/12636 dated Mar. 12, 2018 (BUNIV.003WO) in 14 pages.

Ping One Touch Owner's Booklet, Dated Oct. 2014, (360 pages).

Kolind et al., "Preservation-free drug for insulin pumps," Novo Nordisk Pharmaceutical company, Pump partner meeting ATTD 2020, WOP Technology Presentation, 26 pages.

Renesas Synergy™ Platform, "Capacitive Touch Hardware Design and Layout Guidelines for Synergy, RX200, and RX100." R01AN3825EU0101 Rev.1.01, Jun. 14, 2017, pp. 1-18.

* cited by examiner

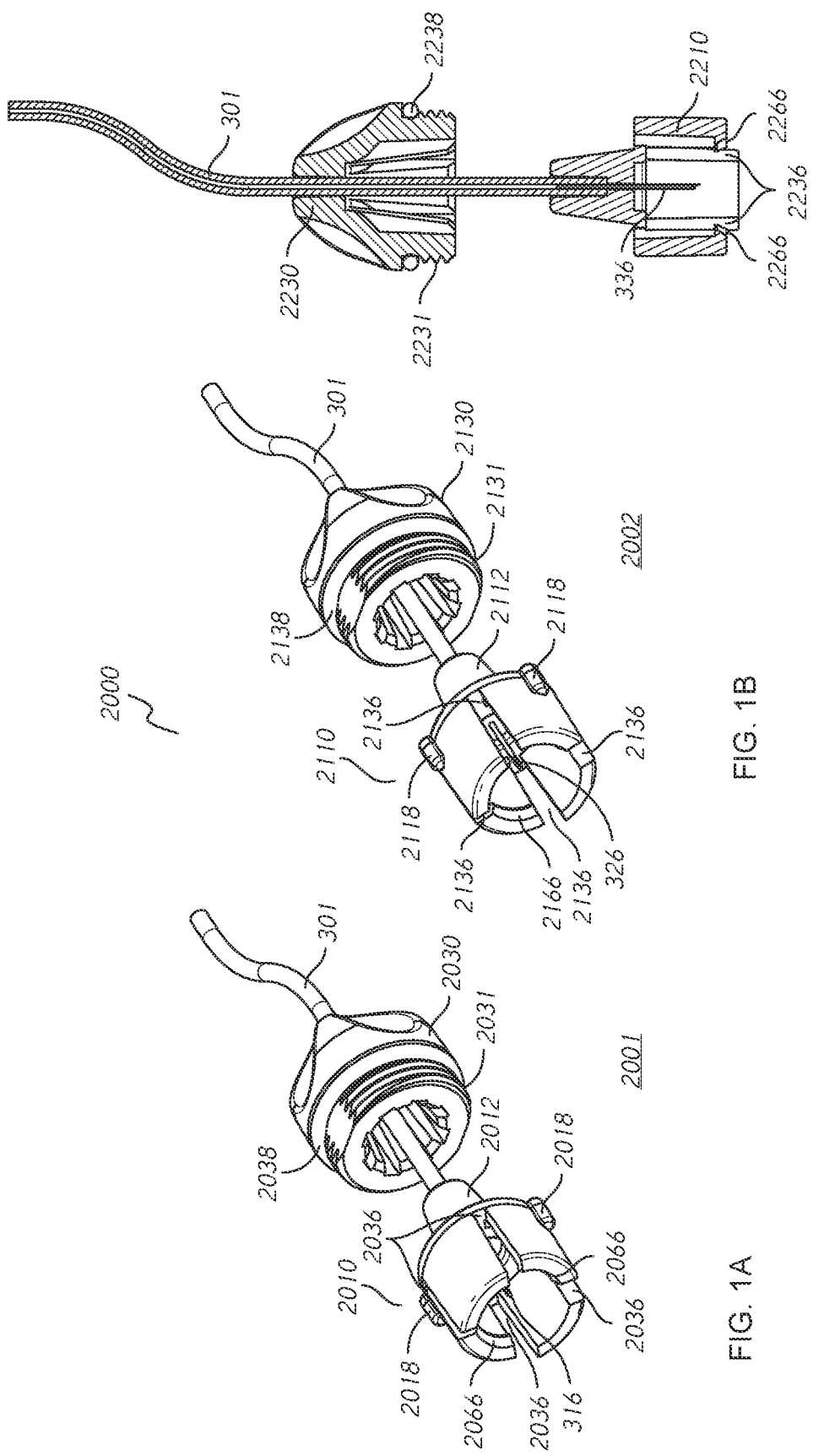

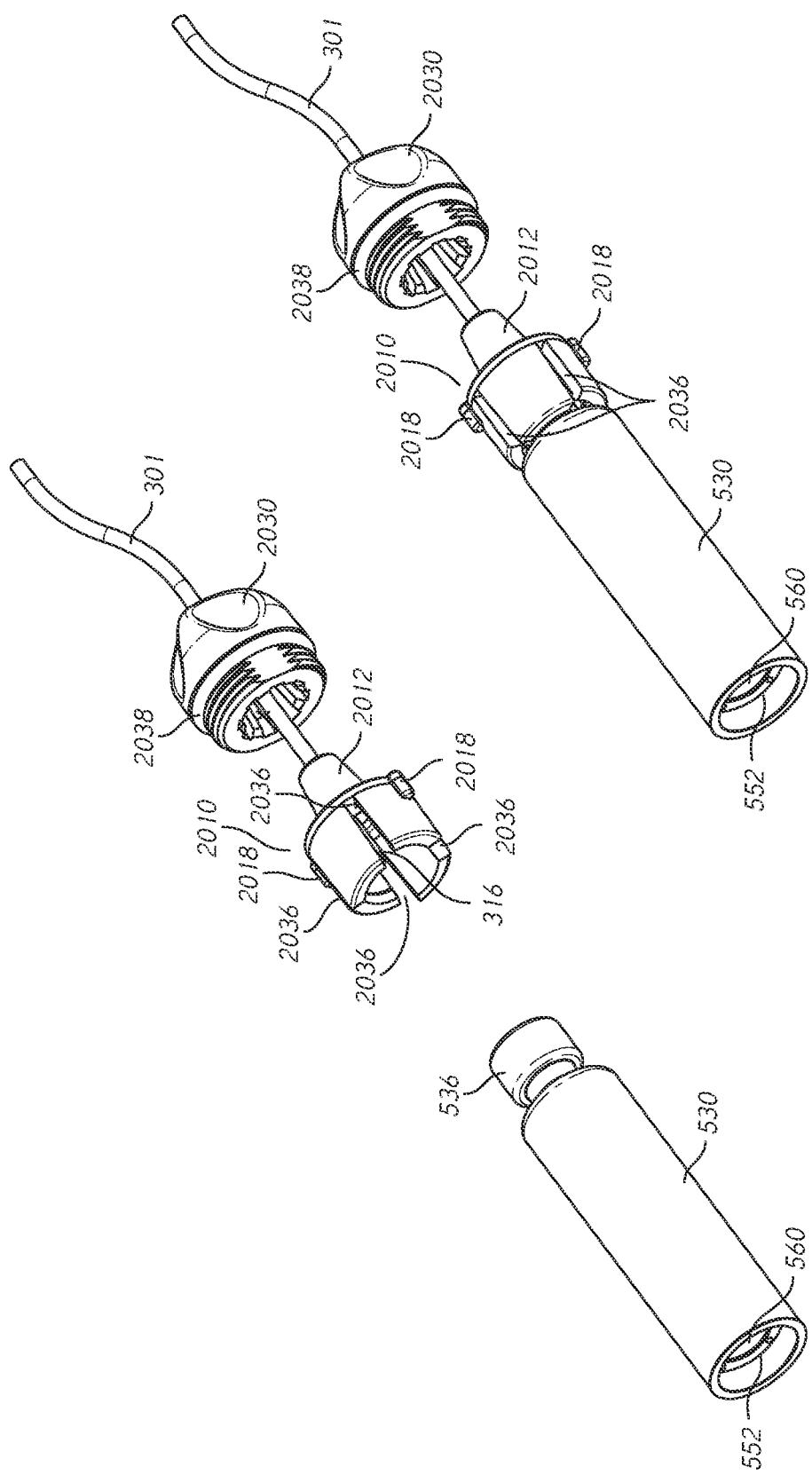

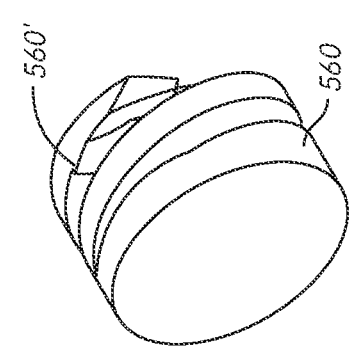
FIG. 6C
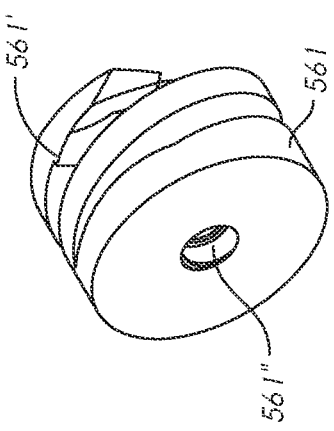
FIG. 6B
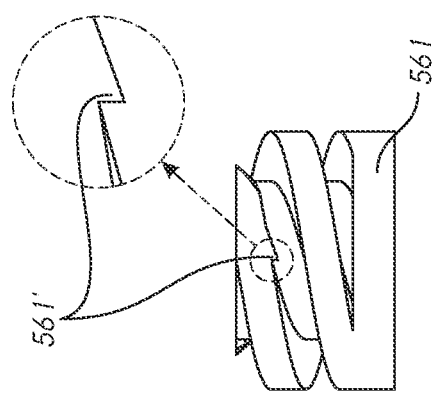
FIG. 6A
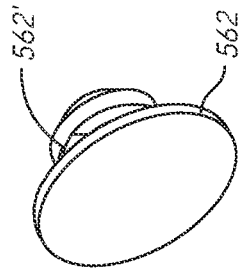
FIG. 6F
FIG. 6E
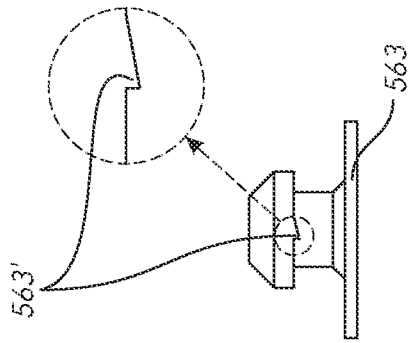
FIG. 6D

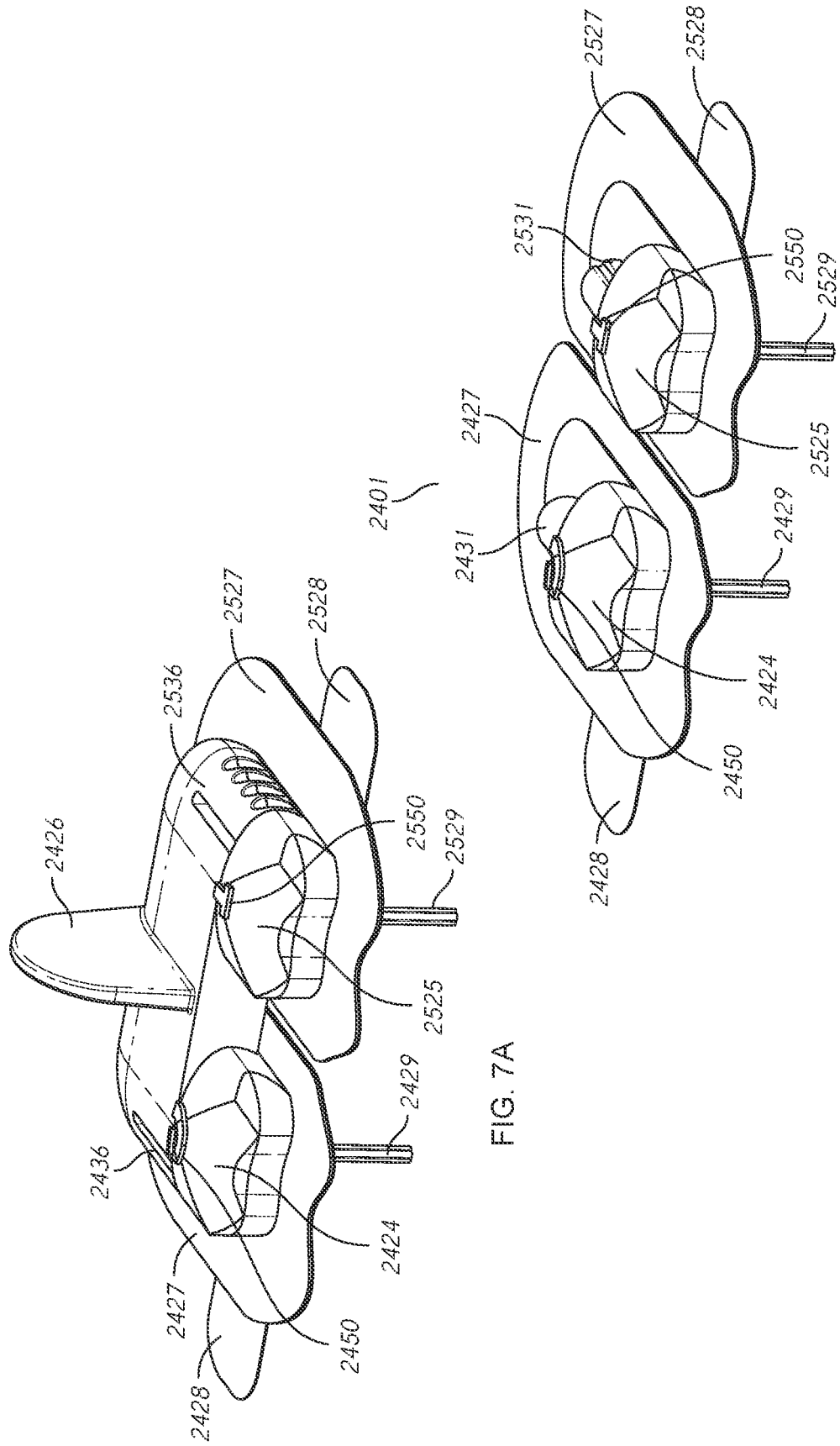

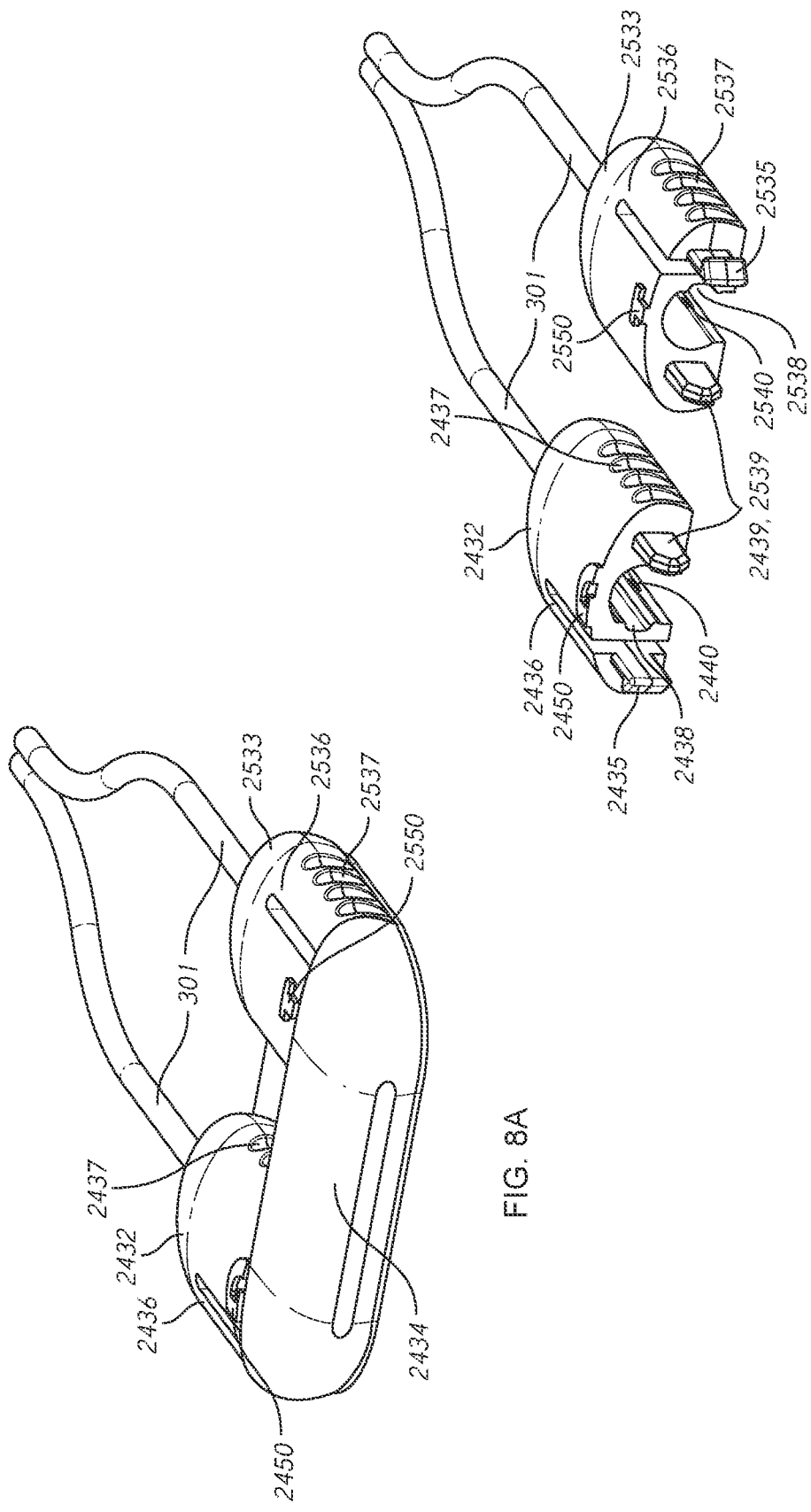

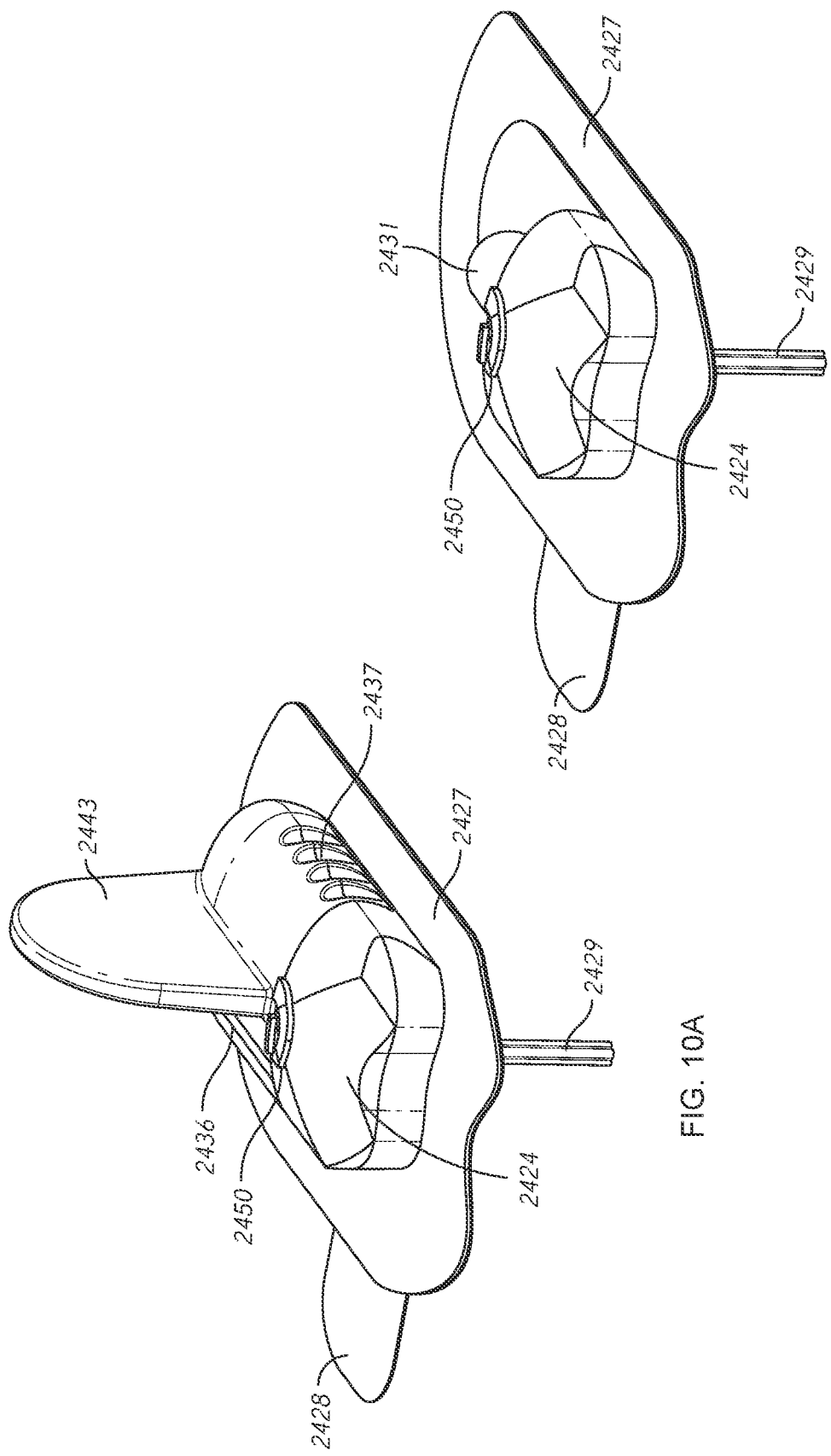

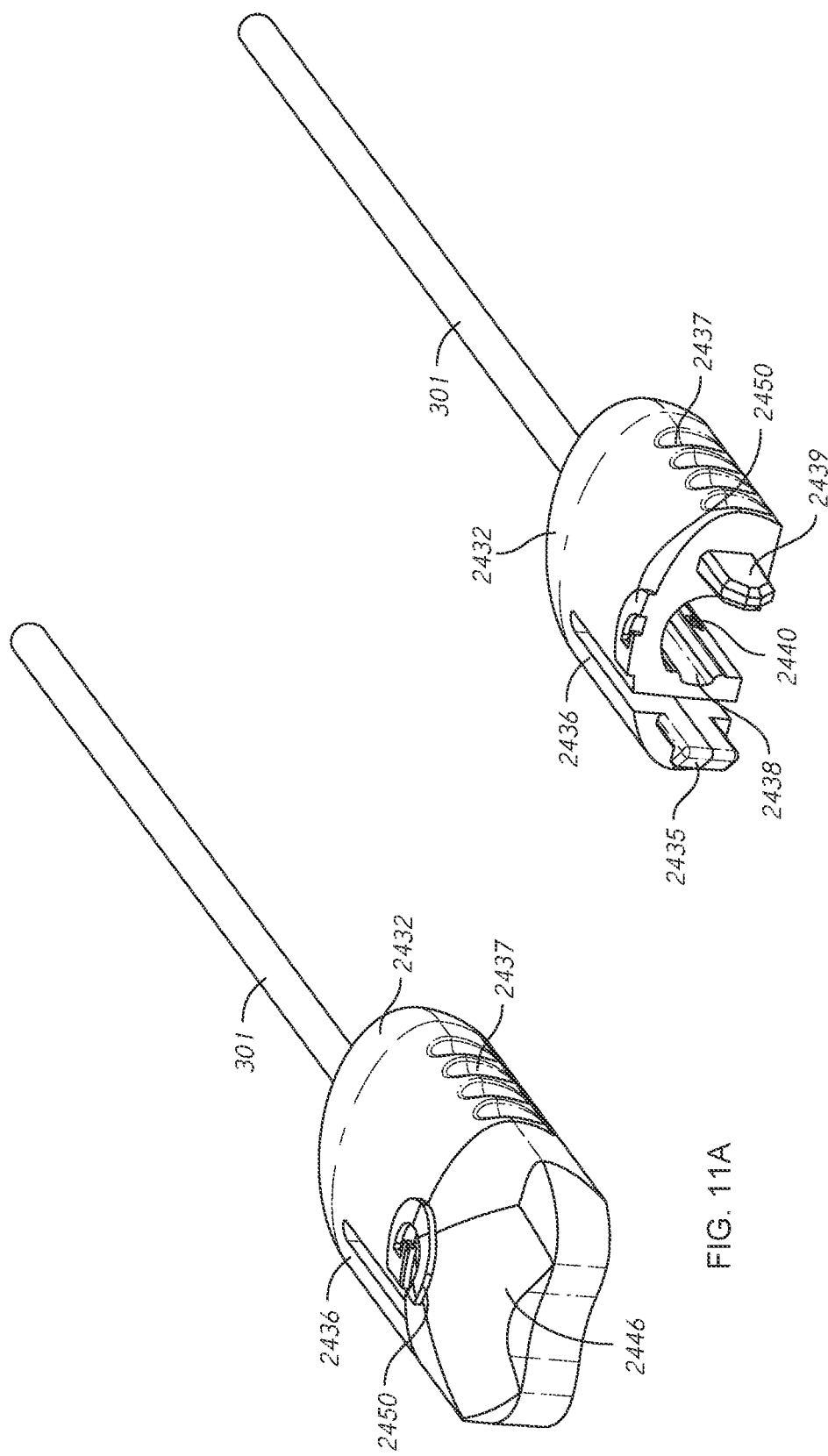

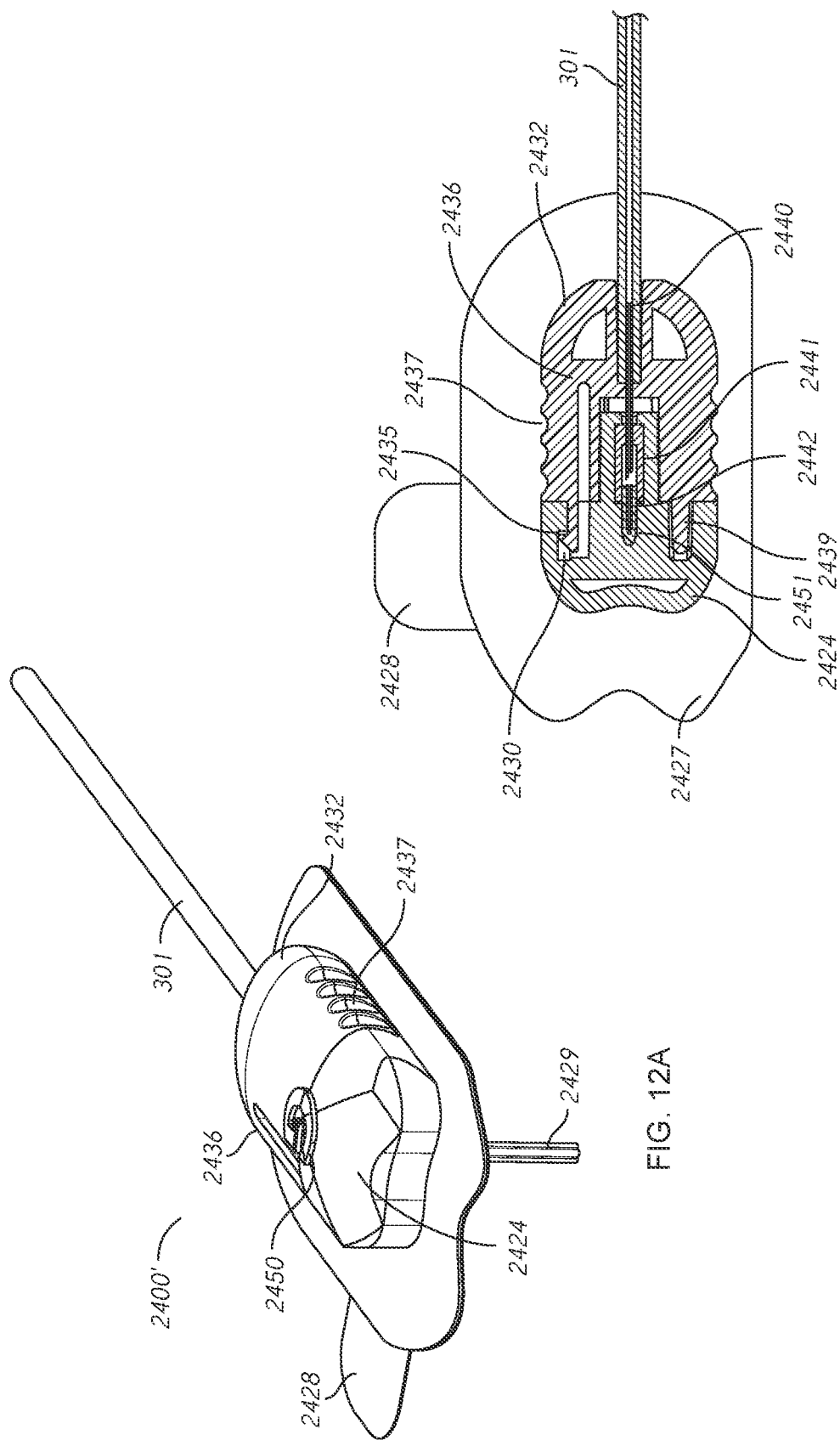

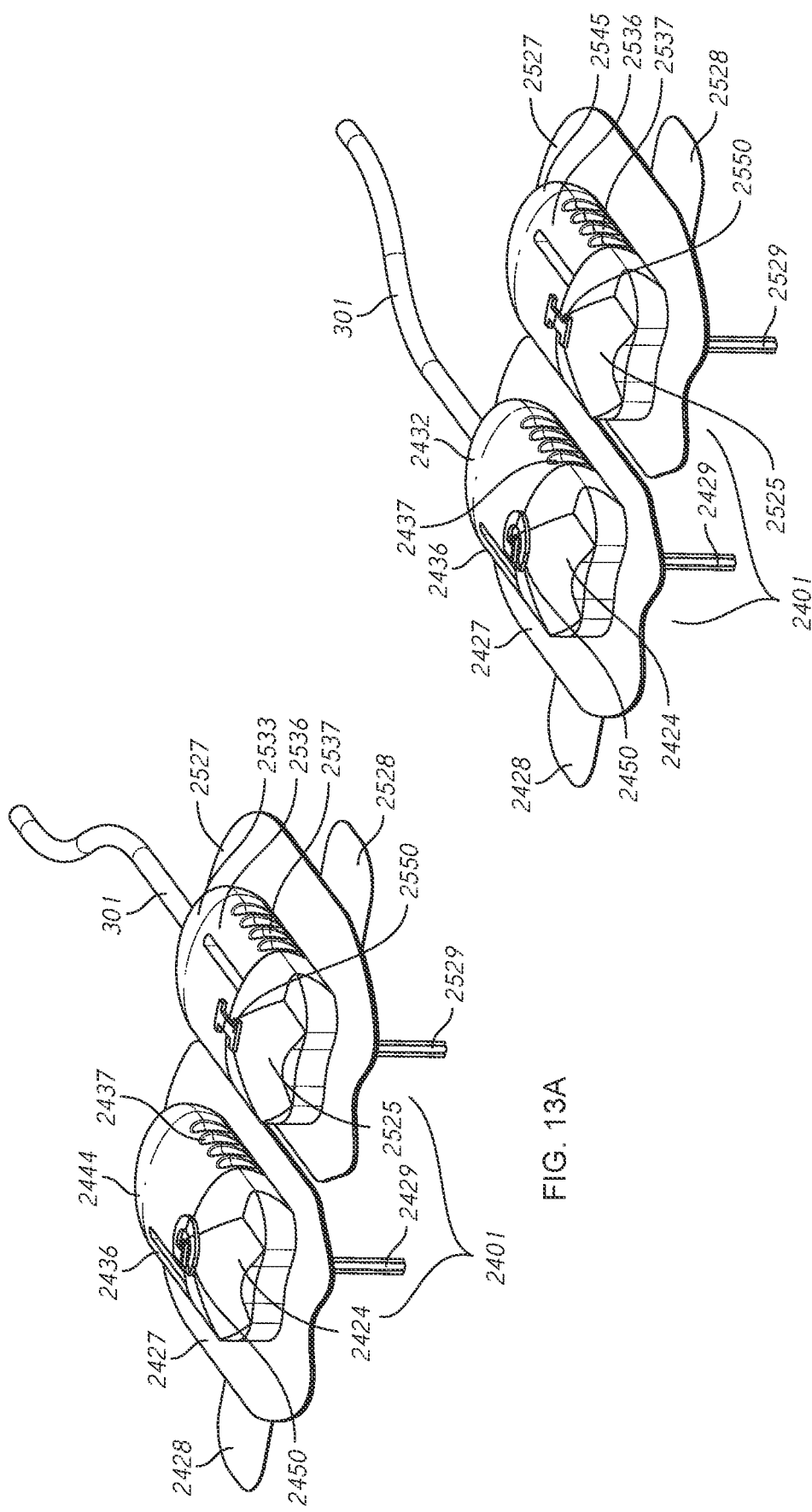

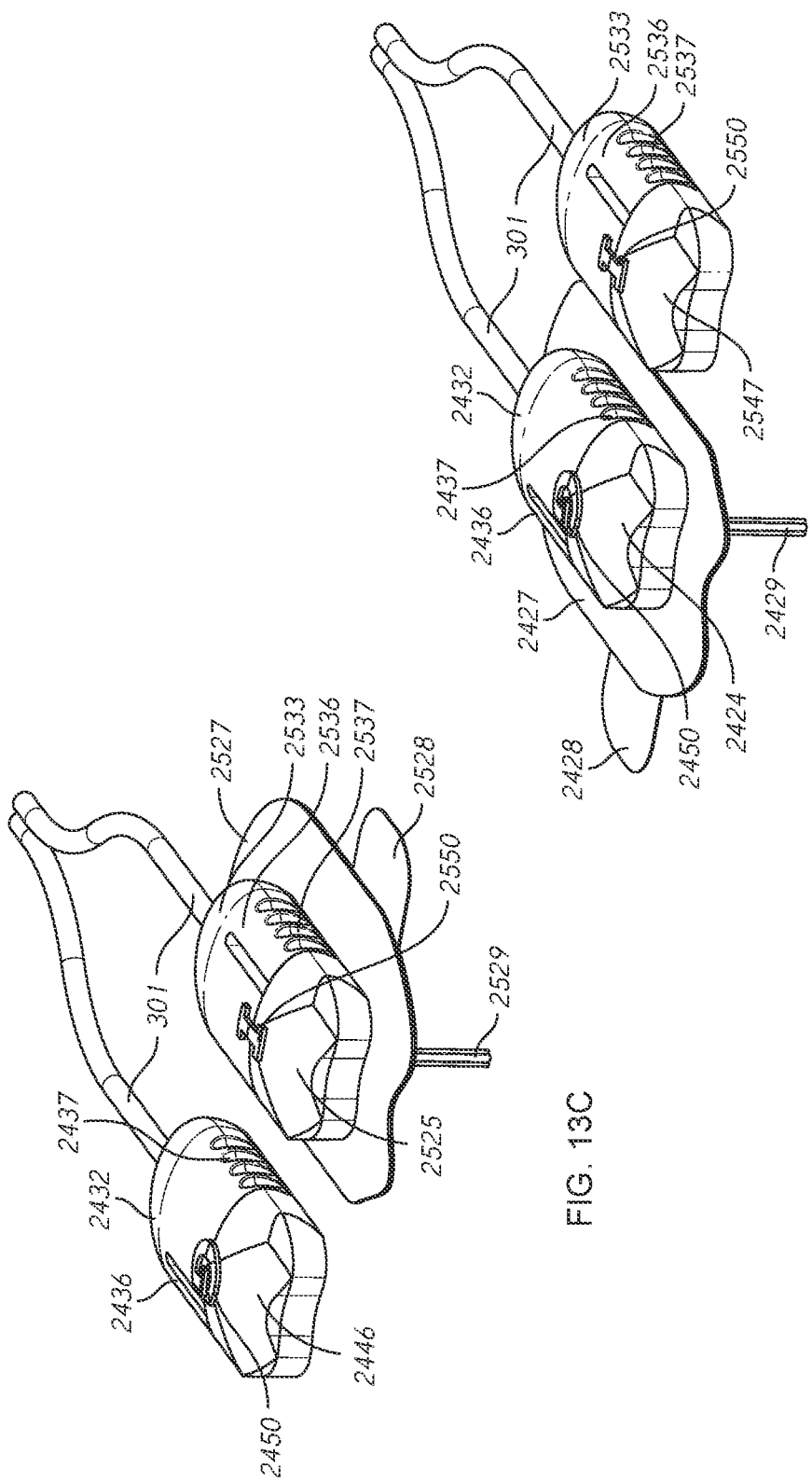

INFUSION SYSTEM AND COMPONENTS THEREOF

CROSS REFERENCE TO RELATED APPLICATIONS

This application is a continuation of U.S. application Ser. No. 16/503,269, filed Jul. 3, 2019, which is a continuation of PCT Application Serial No. PCT/US2018/012636, filed Jan. 5, 2018, which claims priority to U.S. Provisional Patent Application No. 62/444,244, filed Jan. 9, 2017 and U.S. Provisional Patent Application No. 62/443,616, filed Jan. 6, 2017. All of the foregoing applications are hereby incorporated herein by reference in their entireties. Any and all applications for which a priority claim is identified in the Application Data Sheet as filed with the present application are hereby incorporated by reference under 37 C.F.R. § 1.57.

STATEMENT REGARDING FEDERALLY SPONSORED R&D

This invention was made with Government Support under Contract Nos. DK097657 and DK108612 awarded by the National Institutes of Health. The Government has certain rights in the invention.

BACKGROUND

The disclosure relates generally to the field of infusion systems for medicaments and components thereof.

Sustained delivery, pump driven medicament injection devices generally include a delivery cannula mounted in a subcutaneous manner through the skin of the patient at an infusion site. The pump draws medicine from a reservoir and delivers it to the patient via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a patient while others are configured to deliver multiple medicaments to patient.

SUMMARY

Some embodiments disclosed herein pertain to medicament infusion systems, components thereof, and methods of using and/or making infusion systems.

In some embodiments, a medicament infusion set for delivering a single or multiple medicaments to a patient is disclosed. In some embodiments, the medicament infusion set comprises a first reservoir set. In some embodiments, the first reservoir set comprises a first reservoir comprising a first reservoir port that contains a first medicament. In some embodiments, the first reservoir set comprises a first inlet connector that fits over at least a portion of the first reservoir and at least a portion of the first reservoir port. In some embodiments, the first inlet connector comprises a first needle configured to allow access to the first medicament. In some embodiments, the first inlet connector comprises a first engaging member that engages a portion of the first reservoir attaching the first inlet connector to the first reservoir.

Any of the embodiments described above, or described elsewhere herein, can include one or more of the following features.

In some embodiments, the first inlet connector comprises a first check valve. In some embodiments, the check valve is configured to allow fluid to flow from the first reservoir in response to a first threshold fluid pressure.

In some embodiments, the first inlet connector comprises a cover configured to engage the first inlet connector.

In some embodiments, the medicament infusion set further comprises a second reservoir set. In some embodiments, the second reservoir set comprises a second reservoir comprising a second reservoir port that allows access to a second medicament.

In some embodiments, the second reservoir set comprises a second inlet connector that fits over at least a portion of the second reservoir and at least a portion of the second port. In some embodiments, the second inlet connector comprises a second needle configured to allow access a second medicament. In some embodiments, the second inlet connector comprises a second engaging member that engages a portion of the second reservoir attaching the second inlet connector to the second reservoir.

In some embodiments, the second reservoir set comprises a second inlet connector cover configured to engage the second inlet connector.

In some embodiments, the first check valve is configured to substantially prevent unintended leaking of the first medicament from the first reservoir.

In some embodiments, the second inlet connector comprises a second check valve configured to allow fluid flow from the second reservoir in response to a second threshold pressure being reached.

Some embodiments pertain to a medicament infusion set for delivering a single or multiple medicaments to a patient. In some embodiments, the medicament infusion set comprises a first reservoir set.

In some embodiments, the first reservoir set comprises a first reservoir comprising a first reservoir port and a first plunger. In some embodiments, the first reservoir contains a first medicament. In some embodiments, the first plunger comprises a first insert. In some embodiments, the insert comprises a magnetic material distributed throughout the first insert. In some embodiments, the first insert is configured to magnetically couple to a drive nut in a pump that is configured to deliver the first medicament.

In some embodiments, the first reservoir set comprises a first inlet connector. In some embodiments, the first inlet connector fits over at least a portion of the first reservoir and at least a portion of the first reservoir port. In some embodiments, the first inlet connector comprises a first needle configured to allow access to the first medicament. In some embodiments, the first inlet connector comprises a first engaging member that engages a portion of the first reservoir attaching the first inlet connector to the first reservoir.

In some embodiments, the first reservoir set comprises a first inlet connector cover configured to engage the first inlet connector.

In some embodiments, the first insert is rubber, plastic, polymeric, elastomeric, or combinations thereof.

In some embodiments, the medicament infusion set further comprises a second reservoir set comprising a second reservoir comprising a second reservoir port configured to allow access to a second medicament.

In some embodiments, the second reservoir set comprises a second inlet connector that fits over at least a portion of the second reservoir and at least a portion of the second port. In some embodiments, the second inlet connector comprises a second needle configured to allow access a second medicament. In some embodiments, the second inlet connector comprises a second engaging member that engages a portion of the second reservoir attaching the second inlet connector to the second reservoir.

In some embodiments, the medicament infusion set comprises a second inlet connector cover configured to engage the second inlet connector.

In some embodiments, the magnetic material is a material selected from the group consisting of ferrous material, metal shavings, metal beads, and/or metal powder.

In some embodiments, the magnetic material is configured to magnetically couple the first plunger and a magnet at a terminal end of a drive nut of a pump in a way that prevents inadvertent lift-off of the plunger from the drive nut.

In some embodiments, the second reservoir comprises a second plunger comprising a second insert, the second insert comprising a second magnetic material distributed throughout the second insert, wherein the second insert is configured to magnetically repel the first drive nut and to attract a second drive nut of the pump.

In some embodiments, the infusion set comprises the pump.

Some embodiments pertain to a medicament infusion system comprising a pump and a first medicament reservoir. In some embodiments, the pump comprises one or more of a first reservoir receptacle, a motor, and a drive nut located within the first reservoir receptacle and configured to move a plunger to deliver medicament in response to a first electrical current applied to the motor. In some embodiments, the pump comprises a controller. In some embodiment the controller is configured to urge the drive nut forward with the first electrical current. In some embodiments, the first electrical current is insufficient to advance the drive nut forward when in contact with the first plunger. In some embodiments, the controller (and/or a detector of the pump) is configured to detect whether the plunger corresponds to the first plunger. In some embodiments, in response to the detection that the plunger corresponds to the first plunger, the controller is configured to increase an electrical current applied to the motor to a delivery mode current that is sufficient to urge the drive nut forward against the plunger and to move the plunger to deliver the first medicament. In some embodiments, in response to the detection that the plunger does not correspond to the first plunger, the controller is configured to reduce the electrical current applied to the motor or apply a second electrical current that retracts the drive nut.

Some embodiments pertain to a medicament infusion system comprising a pump and a controller. In some embodiments, the medicament infusion system further comprises a first medicament reservoir with a first plunger and a first medicament. In some embodiments, the first medicament reservoir comprises a first plunger and a first medicament. In some embodiments, the pump comprises a first medicament reservoir receptacle configured to hold a medicament reservoir. In some embodiments, the pump comprises a motor. In some embodiments, the pump comprises a drive nut located within the first reservoir receptacle and configured to move in response to a first electrical current applied to the motor. In some embodiments, the pump comprises the controller.

In some embodiments, the controller is configured to apply the first electrical current to the drive nut. In some embodiments, the controller urges the drive nut forward with the first electrical current. In some embodiments, the first electrical current is insufficient to advance the drive nut forward when in contact with a plunger of a medicament reservoir. In some embodiments, in response to the detection of the first plunger, the controller increases an electrical current applied to the motor to a delivery mode current that is sufficient to urge the drive nut forward against the first plunger and to move the first plunger to deliver the first medicament.

In some embodiments, the controller is configured to detect whether the plunger corresponds to the first plunger and, in response to the detection that the plunger does not correspond to the first plunger, the controller reduces the electrical current applied to the motor and/or applies a second electrical current that retracts the drive nut when a plunger that is not the first plunger is detected. In some embodiments, the controller is configured to probe whether the plunger corresponds to the first plunger by tapping against the plunger with successively increased force by increasing the electrical current incrementally from the first electrical current until the force is sufficient to cause the plunger moves thereby indicating the presence of the first plunger (e.g., because the force required to move the plunger corresponds to that required to move the first plunger).

Some embodiments pertain to a controller for controlling operations of a medicament infusion system. In some embodiments, the controller is configured to apply a first electrical current that is configured to advance a drive nut forward. In some embodiments, the first electrical current is less than a threshold current needed to advance the drive nut forward when the drive nut is in contact with a plunger. In some embodiments, in response to the detection that the plunger corresponds to the first type of plunger, the controller increases the first electrical current to a delivery mode current that is sufficient to advance the drive nut forward against the plunger and to move the plunger to deliver a first medicament. In some embodiments, the controller is further configured to interact with a detector. In some embodiments, the detector detects whether the plunger corresponds to a first type of plunger. In some embodiments, in response to the detection that the plunger does not correspond to the first type of plunger, the controller applies a second electrical current to the drive nut that retracts the drive nut or decreases the current to stop the drive nut completely. In some embodiments, the controller is configured to probe whether the plunger corresponds to the first plunger by tapping against the plunger with successively increased force by increasing the electrical current incrementally from the first electrical current until the force is sufficient to cause the plunger moves thereby indicating the presence of the first plunger.

Some embodiments pertain to a medicament infusion set for delivering a single or multiple medicaments to a patient, comprising a first reservoir set. In some embodiments, the first reservoir set comprises a first reservoir comprising a first reservoir port and a first plunger. In some embodiments, the first reservoir comprises a first medicament.

In some embodiments, the first plunger comprises an electrically conducting element configured to interact with an infusion pump such that when the first reservoir is properly positioned in the infusion pump the first plunger is in electronic communication with the infusion pump.

In some embodiments, the first inlet connector that fits over at least a portion of the first reservoir and at least a portion of the first reservoir port.

In some embodiments, the first inlet connector comprises a first needle configured to allow access to the first medicament.

In some embodiments, the first inlet connector comprises a first engaging member that engages a portion of the first reservoir attaching the first inlet connector to the first reservoir.

In some embodiments, the first reservoir set comprises a first inlet connector cover configured to engage the first inlet connector.

In some embodiments, the medicament infusion set further comprises a second reservoir set comprising a second reservoir comprising a second reservoir port configured to allow access to a second medicament within the reservoir.

In some embodiments, the second reservoir set comprises a second inlet connector that fits over at least a portion of the second reservoir and at least a portion of the second port.

In some embodiments, the second inlet connector comprises a second needle configured to allow access a second medicament.

In some embodiments, the second inlet connector comprises a second engaging member that engages a portion of the second reservoir attaching the second inlet connector to the second reservoir.

In some embodiments, the second reservoir set comprises a second inlet connector cover configured to engage the second inlet connector.

In some embodiments, the second reservoir comprises a second plunger wherein the second plunger comprises an electrically conducting element configured to interact with the infusion pump such that when the second reservoir is properly positioned in the infusion pump the second plunger is in electronic communication with the infusion pump.

In some embodiments, the first plunger comprises a first insert comprising a magnetic material distributed throughout the first insert, wherein the first insert is configured to magnetically couple to the first drive nut in the pump.

In some embodiments, the first inlet connector comprises a first check valve that allows fluid flow from the first reservoir after a first threshold pressure is reached.

In some embodiments, the first plunger has a first concentration of the electrically conducting element and wherein the second plunger comprises a second concentration of the electrically conducting element.

In some embodiments, the first plunger has a first electrical impedance and the second plunger has a second electrical impedance.

In some embodiments, the first electrical impedance is indicative of a first drug and wherein the second electrical impedance is indicative of a second drug, the second drug different from the first drug.

Some embodiments pertain to an infusion set for delivering a single or multiple medicaments to a patient comprising a base set. In some embodiments, the base set comprises one or more of a first base unit having a first port and a first adhesive portion. In some embodiments, the first base unit comprises a first piercing element configured to deliver a first medicament to the patient. In some embodiments, the first adhesive portion is configured to adhere the first base unit to the patient.

In some embodiments, the infusion set comprises a second base unit having a second port. In some embodiments, the second base unit comprises a second adhesive portion configured to adhere the second base unit to the patient.

In some embodiments, the infusion set comprises a connector set. In some embodiments, the connector set comprises a first connector configured to reversibly couple to the first base unit via the first port and to provide a first fluid path from a first medicament infusion to the first port of the first base. In some embodiments, the connector set comprises a second connector configured to reversibly couple to the second base unit.

In some embodiments, the first base unit comprises a first guide member that prevents engagement of the second connector to the first base unit In some embodiments, the second base unit comprises a second guide member that prevents engagement of the first connector to the second base unit. In some embodiments, the first base unit and the second base unit are able to move independently with respect to each other and are configured to fit contours of the patient's body during movements made by the patient.

BRIEF DESCRIPTION OF THE DRAWINGS

Various embodiments are depicted in the accompanying drawings for illustrative purposes, and should in no way be interpreted as limiting the scope of the embodiments. Any features, structures, components, materials, and/or steps of any of the embodiments can be combined or replaced with any features, structures, components, materials, and/or steps of any other of the embodiments to form additional embodiments, which are part of this disclosure.

FIGS. 1A-1C illustrate embodiments of inlet connectors, inlet connector covers, and components thereof.

FIGS. 2A-2C illustrate exploded and partially assembled views of an embodiment of a reservoir, an inlet connector, an inlet connecting cover, and components thereof.

FIGS. 6A-6F illustrate various inserts for engaging medicament reservoir pistons, plungers, drive nuts, and/or pushrods.

FIGS. 6O-6P are schematic depictions showing configurations of the medicament delivery system.

FIGS. 6U-6Z are schematic depictions showing configurations of the medicament delivery system with a resisting feature.

FIGS. 7A-7B illustrate perspective views of a dual infusion set base where 7A also illustrates an insertion implement.

FIGS. 8A-8B illustrate perspective views of dual medicament distribution connectors where 8A also illustrates a cover for the distribution connectors.

FIGS. 10A-10B illustrate a single medicament infusion housing set base where an insertion implement is attached (10A) or detached (10B).

FIGS. 11A-11B illustrate perspective views of a single medicament distribution connector where 11A also illustrates a cover for the distribution connector.

FIGS. 12A-12B illustrate views of a single medicament infusion base set where 12B is a cross-sectional view from the top.

FIGS. 13A-13E illustrate various configurations of dual medicament infusion set bases, connectors, and covers.

DETAILED DESCRIPTION

Figure 2A:
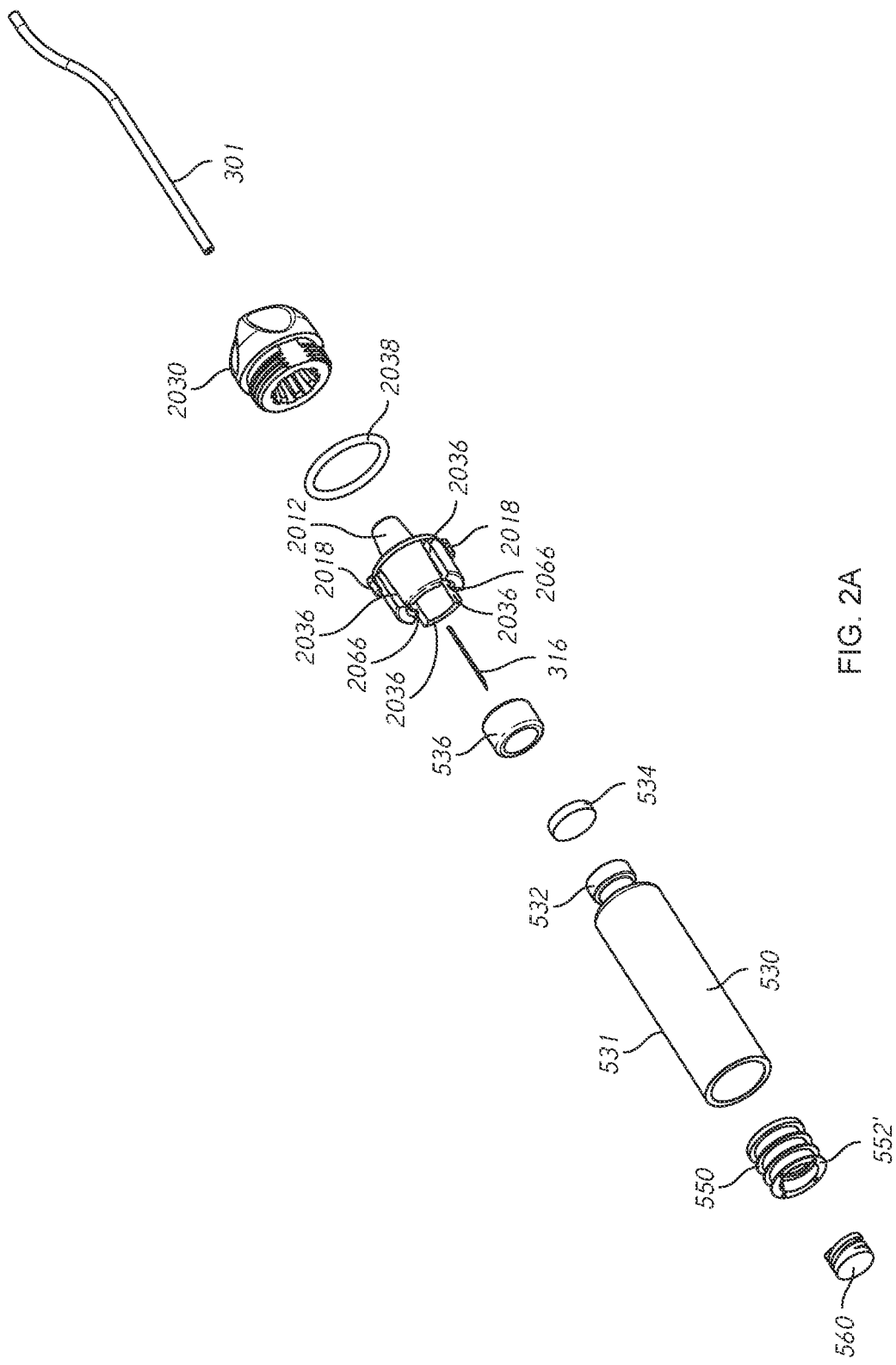

Some embodiments described herein pertain to infusion systems, medicament loading systems, and methods for introducing or infusing medicaments and to provide proper channeling medicaments to patients.

A drawback of multi-medicament (e.g., pharmaceutical, hormone, etc.) and certain single medicament regimens is that the patient or physician may accidentally load, transfer, and/or administer the incorrect medicament. For instance, a user may mistakenly believe that he or she is providing one medicament when they are accidentally supplying a different one. The accidental administration of the incorrect medicament to the patient can have serious and potentially fatal consequences. For example, standard-of-care insulin therapies for regulating blood glucose in diabetic patients may involve subcutaneous infusion of insulin via an insulin pump. If the amount of dosed insulin is excessive, it can lead to hypoglycemia or a situation of impending hypoglycemia. To combat and/or reverse such adverse situations, individuals typically consume additional carbohydrates (e.g. sweet juice or glucose tablets). In some situations, individuals can alternatively and/or additionally administer a so-called "rescue dose" of a counter-regulatory agent, such as glucagon. A counter-regulatory agent combats the effect of the excess medicinal dose (e.g., excess insulin) alleviating or substantially preventing adverse effects related to the excess dose. Glucagon can be reconstituted into solution from an emergency kit and manually administered intramuscularly. If a patient is given additional insulin instead of a rescue dose of glucagon, the results could be catastrophic, potentially leading to death. Similarly, during a diabetic episode, if a patient requires insulin but is given glucagon instead accidentally, that administration could exacerbate the episode and could lead to devastating effects and potentially death.

As illustrated above, the proper channeling in medicament dosing is critical where one medicament is used to achieve one effect while the other is used to achieve a different and/or the opposite effect (e.g., in the case of insulin and glucagon). In a multi-medicament automated system, if the medicaments are accidentally loaded in the incorrect reservoirs or incorrect chambers of a pump, the automated system could deliver an ineffective (and potentially harmful) medicament to the patient. This phenomenon of incorrect medicament administration in automated systems is called cross-channeling. Cross-channeling is dangerous because the wrong medicament could have the opposite of the intended effect or a side effect that is unanticipated. This improper channeling could not only fail to alleviate the patient's condition, but could make the patient's condition worse, or cause a new problem-state for the patient. For instance, this improper channeling could cause a negative feedback loop, wherein the control system attempts to adjust the patient's disease state in one direction, but the delivery of the incorrect medicament exacerbates or causes no effect on the disease state. Sensing this, the control system can trigger further doses of the wrong medicament in an attempt to control the patient's condition, while actually causing the patient's condition to further deteriorate (or causing overdosing of the incorrect medicament).

While diabetic drugs are used as an example above and elsewhere herein, improper channeling can have deleterious effects in many multi-medicament regimens (e.g., in drugs that regulate pancreatic enzymes, etc.) because a medicament is not administered to the patient at the necessary time or an incorrect medicament is administered at a dangerous level. Thus, the embodiments and considerations provided herein can be applied to any drug individually and/or any drug combination. Additionally, while cross-channeling can refer to systems where two medicaments are inserted into the incorrect chambers of a distribution system, the term cross-channeling as used herein can also refer to systems were more than two medicaments are used and/or where a single medicament is used (for example, when a single medicament is improperly placed in a distribution system).

Described herein are infusion systems for multiple medicaments (or single medicaments) and various connectors, tubes, and cartridges that ensure, help ensure, and/or substantially aid in providing proper channeling of each medicament to the patient. While certain embodiments, of infusion systems and components are described below to illustrate various examples that may be employed to achieve one or more desired improvements, these examples are only illustrative and not intended in any way to restrict the general inventions presented and the various aspects and features of these inventions. The phraseology and terminology used herein is for the purpose of description and should not be regarded as limiting. No features, structure, or step disclosed herein is essential or indispensable.

Certain embodiments of the infusion systems and components described herein are configured to minimize, lessen, and/or otherwise help avoid the occurrence of cross-channeling of medicaments. In other words, where multiple medicaments are supplied by the infusion systems disclosed herein, the features and/or components described herein are configured to prevent, minimize the occurrence of, or otherwise inhibit the opportunity for a user to inadvertently place a medicament in the incorrect reservoirs. In some embodiments, one or more benefits of the infusion systems and components disclosed herein can be realized when a single medicament is used in the system. Additionally, the strategies described herein are also applicable to systems with single medicaments. In other words, in some embodiments, as noted elsewhere herein, reference to systems that prevent "cross-channeling" also can include systems employing a single medicament. In some embodiments, for example, the infusion systems disclosed herein provide a single medicament infusion system that, using the strategies and/or design features disclosed herein, ensure that only that single, appropriate medicament can be used and that inappropriate and/or incorrect medicaments cannot be used. Thus, in some embodiments, the systems disclosed herein that avoid cross-channeling are intended to include single medicament systems that ensure proper placement (and/or channeling) of single medicaments.

Some embodiments described herein pertain to an infusion system for dosing multiple medicaments (or a single medicament) without cross-channeling. In some embodiments, cross-channeling is avoided by providing design features and/or mating connectors or adapters on certain components of the infusion system. For instance, in some embodiments, the infusion system comprises an infusion pump with one, two, or more infusion chambers (or pump chambers), drive shafts. In some embodiments, the system further comprises cartridges filled with different medicaments, and connectors and tubing that connect to the cartridge to the infusion pump in such a way as to prevent mischanneling or cross-channeling of medicaments. In certain variants, each type of cartridge for each type of medicament has one or more unique differentiating features (either as an integral part of the cartridge or as a component attached or affixed to the cartridge), for example geometric or shape-based features, that allow for unique coupling with a type of connector that itself has unique differentiating features that engage corresponding features in the pump housing and allow for insertion of the proper cartridge into the proper infusion chamber, drive shaft, or pump chamber within the infusion pump.

In certain variants, the system comprises an infusion set. In some embodiments, the infusion set comprises a base with a housing having one or more implements (e.g., delivery members, needles, etc.) that allow delivery medicaments to the patient from the system. In some variants, the housing is connected to a distribution set comprising one or more distribution connectors that are configured to receive a medicament from one or more medicament reservoirs (e.g., via a conduit etc.). In some embodiments of the system, one or more fluid conduits provide fluidic communication between the reservoirs and a distribution connector set. In various implementations, the connector set comprises one or more cartridge connectors that couple the fluid conduits to the medicament reservoirs. In some variants of the system, the reservoirs (or reservoir) are located in (and/or can be placed in) a pumping device configured to distribute the medicament from the reservoirs (or reservoir) to the conduit, thereby supplying the system with medicaments. In some embodiments, the fluid conduits provide separate pathways that terminate at designated delivery members (e.g., needles, cannulas, etc.) within the base, thereby enabling independent delivery (e.g., subcutaneous or otherwise) of medicaments separately.

In some embodiments, unique mating connectors and design elements ensure that each portion of the system can only be connected within the system in a unique way or configuration, thus preventing the cross-channeling. In certain embodiments, the design features give rise to the following advantages: (1) the infusion system allows the user to easily connect and disconnect the channels independently from both medicament sources as well as from the infusion ports or sites; (2) the infusion system mitigates the possibility of mischanneling by accidentally connecting the wrong tubing to the wrong medicament source or infusion site (e.g., by having a connector that is disposed between one tube and one pump reservoir of one medicament system differ from the connector of the other tube and reservoir); and (3) the infusion system allows for a single or multistep insertion of the dual-cannula infusion site or port. In some embodiments, the components described herein (connectors, bases, ports, channels, etc.) can further comprise visual or brail call-outs in addition to or instead of various paired physical features disclosed herein. For instance, in some implementations, the components can comprise call-outs with wording indicating a proper medicament. In some variants, different colors (red, blue, yellow, green, orange, violet, etc.) or lengths (or other variables) to provide visual feedback regarding appropriate medicaments for appropriate components.

In some embodiments, as stated above, the infusion system can be used to provide separate fluid pathways for a variety of medicaments (e.g., drugs, hormones, proteins, pharmaceuticals, biologics, etc.) dissolved in a variety of liquid carriers (and/or liquid drugs). In certain embodiments, different liquid vehicles may be preferred based on the solubility, stability, or sensitivity of the medicament in a particular carrier. In some embodiments, aqueous solutions (buffers, etc.) are used as a delivery vehicle for the medicament. In certain variations, solvents such as DMSO are used to dissolve medicaments. In some embodiments, solvent/aqueous mixtures are used.

Some embodiments disclosed herein pertain to an infusion system for preventing mischanneling of medicaments and/or inadvertent administration of a medicament. In some embodiments, the infusion system can be used for multiple medicaments or a single medicament. In some embodiments, the infusion system comprises various needle sites, connectors, tubes, and/or cartridges. In some embodiments, the infusion system and/or components thereof ensure proper channeling of each medicament to the patient. In some embodiments, the infusion system comprises an infusion pump. In some embodiments, the infusion pump comprises one, two, or more pump chambers. In some embodiments, the infusion pump is configured to be used with pump cartridges. In some embodiments, the cartridges can be filled at the point of care with different medicaments (or may be pre-filled with different medicaments, for example, at a pharmaceutical company). In some embodiments, different connectors and/or tubing can connect the cartridges to the infusion pump in such a way as to prevent mischanneling and/or cross-channeling of medicaments. In some embodiments, each type of cartridge for each type of medicament has unique differentiating sizes, shapes, and/or geometrical features (either as an integral part of the cartridge or as a component attached or affixed to the cartridge) that allow for unique coupling with a type of connector. In some embodiments, each connector itself has unique differentiating features that engage corresponding features in the pump housing. In some embodiments, each connector only allows for insertion of the proper cartridge into the proper pump chamber within the infusion pump.

In some embodiments, the medicament infusion system comprises an inlet system. In some embodiments, the inlet system comprises a connector set. In some embodiments, the connector set is configured (e.g., has pairing features) that prevent mischanneling of medicaments. FIGS. 1A-B show isometric views of a connector set 2000 comprising a first inlet connector 2010 (a needle connector) and a second inlet connector 2110 (a second needle connector) adapted to prevent mischanneling. FIGS. 1A-B show two embodiments in which different needle connectors 2010, 2110 (e.g., the inlet connector), have unique differentiating guiding elements 2018, 2118 (e.g., tabs, features, or protrusions), separated by 180 degrees (FIG. 1A) and 120 degrees (FIG. 1B). In some embodiments, adjacent guiding elements are separated by values independently selected from equal to or greater than: about 180°, about 160°, about 140°, about 120°, about 100°, about 90°, about 80°, about 70°, about 60°, about 50°, about 40°, about 30°, about 20°, about 10°, values between the aforementioned values or otherwise.

Figure 3B:
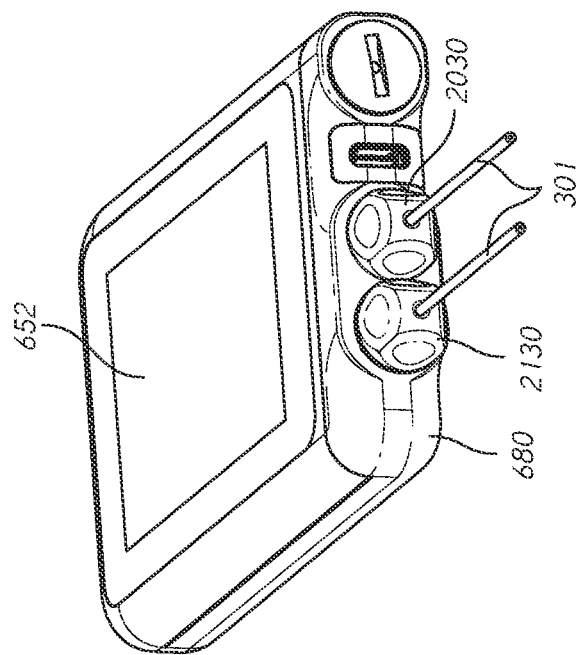
FIGS. 3A-3B illustrate a pump assembly engaging with medicament reservoirs fitted with the inlet connectors and covers of FIGS. 1A-B.
Figure 3A:
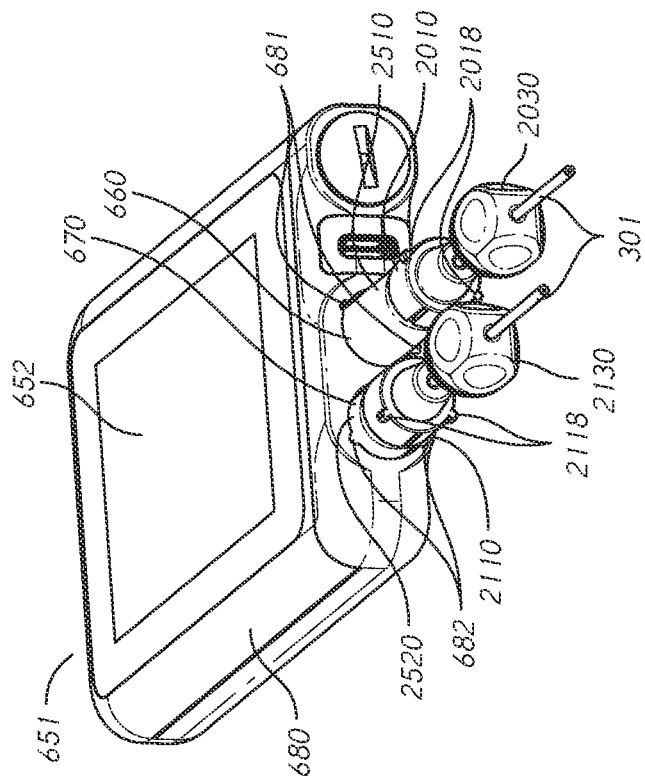

In some embodiments, these unique differentiating guiding elements 2018, 2118 (e.g., tabs, features, or protrusions) mate uniquely with corresponding guiding element apertures 681, 682 (e.g., cavities, grooves, keyways, or slots) in the pump housing 680 of a pump 651 (as shown in FIGS. 3A-B) such that insertion of an inlet connector 2010, into the wrong pump receptacle 670 (e.g., chamber) is prevented. As shown in FIG. 1C, a cross-sectional view of the needle connector assembly, in some embodiments, the inlet connector 2210 lacks unique differentiating tabs, features, or protrusions.

In some embodiments, as shown in FIGS. 1A-B, the inlet connectors 2010, 2110 can have inlet connector spacers 2036, 2136 (e.g., relief slits). In some embodiments, the connector spacers allow the inlet connector to expand (e.g., over a vial to snap tight around the vial or vial cap—e.g. an aluminum crimp) and/or to contract (e.g., to snap into a pump receptacle). In some embodiments the inlet connectors 2010, 2110 comprise projection mates 2066, 2166 (e.g., capture-and-locking features) to facilitate interaction with a medicament cartridge (shown in FIGS. 2A-C). In some embodiments, the capture-and-locking features snap into place by engaging the underside of, for example, an aluminum crimp seal and simultaneously interlocking and securely fastening the needle connector with the aluminum crimp seal around the head (or crown) of the cartridge (e.g., vial). In some embodiments, once fastened, the cartridge and needle connector subassembly can then be inserted and fastened into a pump housing.

In some variants, where multiple relief slits are present, the relief slits can be spaced unevenly about the collar so that some projections are closer and some are farther. In some embodiments, adjacent relief slits are separated by values independently selected from greater than or equal to: about 180°, about 160°, about 140°, about 120°, about 100°, about 90°, about 80°, about 70°, about 60°, about 50°, about 40°, about 30°, about 20°, about 10°, values between the aforementioned values or otherwise. In some embodiments, this inlet connector spacer allows the inlet connector to be compressed as it inserts into a pump housing or expanded as it is slid over a collar/reservoir assembly. This can allow snap tight fitting into a pump housing or with a collar/reservoir assembly that comprises mated features. For instance, in some embodiments, once inserted all the way into the housing, the inlet connector spacers can re-expand, allowing the geometric features of the inlet connector to interact with mated apertures or features of the pump housing. This feature, among others described herein, can allow the reservoir to be held in an appropriate position, with little movement and/or substantially without movement, within the pump housing. In some embodiments, the relief slits allow the inlet connector to be pressed over the head (or crown) of the cartridge. In some embodiments, a locking mechanism snaps the inlet connector in place as it engages with the underside of the head (or crown) of the cartridge.

In some embodiments, the needle connector has any number of unique differentiating tabs, features, protrusions, and/or combinations thereof, as in FIGS. 1-4, which would allow insertion into the pump chamber of a pump housing that contains corresponding cavities, grooves, keyways, or slots to match with the unique differentiating tabs, features, or protrusions on the needle connector. In this way, only one type of needle connector can be inserted uniquely into one particular pump chamber. Alternatively, the needle connector might contain any number of cavities, grooves, keyways, or slots (not shown) that uniquely mate with tabs, features, or protrusions in the pump chamber of a pump housing.

In some embodiments, as shown in FIGS. 1A-C, tubing 301 is individually affixed (e.g., overmolded, bonded, press-fitted, glued, solvent bonded, insert molded, or otherwise attached) to individual inlet connectors 2010, 2110, 2210 (e.g., the needle connector). In some embodiments, tubing 301 (e.g., channels, or other fluid conduits) connects to separate piercing elements 316, 326, 336 (e.g., a straight, beveled, hollow, and/or stainless steel needles and/or catheters, etc.) in such a way as to allow a closed, independent, patent, and continuous fluid path from a medicament vial through piercing elements 316, 326, 336, inlet connectors 2010, 2110, 2210 and/or tubes 301 and on to an infusion set. In some embodiments, the piercing elements 316, 326, 336 can be recessed within the inlet connectors 2010, 2110, 2210 so as to be touch-proof (e.g., preventing the piercing element from pricking a user as the inlet connector is manipulated). In some embodiments, as shown in FIGS. 1A-C, the inlet systems comprise inlet connector covers 2030, 2130, 2230. In some embodiments, the inlet connector covers 2030, 2130, 2230 engage the inlet connectors 2010, 2110, 2210 via a pairing projection 2012, 2112, 2212. In some embodiments, the pairing projections comprise one or more features (e.g., tabs, slits, projections, etc.) and/or are sized enable covers to engage only with paired inlet connectors (not shown). In some embodiments, as shown in FIGS. 1A-C, the inlet connector covers 2030, 2130, 2230 (e.g., caps) can comprise a tightening feature 2031, 2131, 2231 (e.g., threads, friction pairings, etc.) that allows them to be affixed into a pump receptacle. In some embodiments, the connector cap/cover 2030, 2130, 2230 is freely rotatable around the tubing 301. In some embodiments, the tubing passes through a threaded coaxial cap (e.g., the connector cover) such that the cap is free to slide up and down the tubing and to thread into a pump housing, as in FIGS. 3A and 3B. In some embodiments, the cap 2030, 2130, 2230 can slide up and down the tubing 301 and can be used to secure the cartridge (e.g., vial, medicament reservoir) and needle connector (e.g., inlet connector) sub-assembly to a pump housing (shown in FIGS. 3A and 3B). In some embodiments, the covers engage the pairing projection (by features or by friction). In some embodiments, while engaged, the covers are still freely rotatable about the inlet connector. For example the pairing projection can comprise a circumferential track and the cover can comprise a circumferential protrusion that fits into the tract. In some embodiments, the track holds the cover to the pairing projection, but allows free movement (e.g., allowing the cover to be screwed into the pump receptacle).

In some embodiments, an inlet connector, such as the ones shown in FIGS. 1A-5C, has relief slits on the sides, which allow it to expand slightly as it is pressed over the aluminum crimp seal around the head (or crown) of a medicament-filled cartridge, and a capture-and-locking feature, which snaps into place by engaging the underside of the aluminum crimp seal and simultaneously interlocking and securely fastening the needle connector with the aluminum crimp seal around the head (or crown) of the cartridge. In some embodiments, once fastened, the cartridge and needle connector subassembly can then be inserted and fastened into a pump housing 680 (as in FIGS. 3A-B).

In some embodiments, as shown in FIGS. 1A-B, the inlet connector system 2001, 2002 can comprise a gasket feature 2038, 2138 (e.g., an o-ring, or compressible feature) located around (e.g., around the periphery, external circumference, etc.) of an inlet connector cover 2030, 2130 or other inlet connector system feature. In some embodiments, the o-ring allows the connector cap 2030, 2130 to be securely fastened to the pump 651 such that the medicament vials have little or no movement when inserted into the pump 651 via the receptacles 660, 670 and tightened there using the tightening features 2131, 2231. Even though the medicament receptacles can be isolated from the rest of the pump housing, the o-ring also reduces (e.g., minimizes, lowers, etc.) fluid ingress into the medicament receptacle such that consequent pump damage is minimized.

FIGS. 2A-C show various components and isometric views of (A) individual components that could be used in a cartridge and needle connector assembly, (B) the sub-assemblies that would be used in such an embodiment, and (C) the fully connected cartridge and needle connector assembly. To form the cartridge sub-assembly, a seal 536 (e.g., an aluminum crimp seal, etc.), wraps around the cartridge septum 534 and the head 532 (or crown) of the cartridge body 531. In some embodiments, the seal 536 and septum 534 can be used to create a sterile barrier and fluid seal on one end of the medicament reservoir 530.

In some embodiments, an elastomeric plunger 550 creates a sterile barrier and fluid seal on the other end of the cartridge 530. In some embodiments, the elastomeric plunger 550 has a receptacle 552' that captures (e.g., through threading, friction, etc.) an insert 560 (e.g., a magnetic insert). In some embodiments, as shown, the insert 560 (e.g., the ferrous insert) is threaded to correspond and engage paired threads on the plunger 550. In some embodiments, the insert 560 could be used with a coupled piston (e.g., magnetically coupled) to prevent accidental medicament delivery caused by inadvertent separation of the piston from the elastomeric plunger 550. In some embodiments, this insert which can comprise a magnetic material (e.g., a ferrous material and/or metal shavings, metal beads, metal powder, etc.) can facilitate magnetic coupling between a magnet at the end of the drive nut in a pump chamber and the elastomeric plunger such that it would prevent inadvertent departure or lift-off of the elastomeric plunger from the drive nut as in the case of unintentional medicament delivery caused by gravitationally induced changes in hydrostatic pressure between the patient and the infusion system, or any other changes in hydrostatic pressure that might arise between the patient and the infusion system. In some embodiments, the ferrous insert could be connected to the elastomeric plunger by means of a snug-fit or snap-fit. In some embodiments, the ferrous material comprises and/or is iron in the form of shavings, bead, powder, etc.

In some embodiments, the inlet connector 2010 (i.e., needle connector) by virtue of its relief slits 2136 can expand around the head 532 (or crown) of the cartridge fitted with the crimp seal 536 allowing its capture-and-locking features/ projection mate 2066 to snap into place by engaging the underside of the aluminum crimp seal 536 and simultaneously interlocking and securely fastening the inlet connector 2010 with the aluminum crimp seal 536. The cartridge and needle connector sub-assembly can be inserted into a pump housing and the threaded coaxial cap 2030 which is free to slide along the tubing 301, shown in FIG. 2C, is used to fasten the sub-assembly to the pump housing, with the o-ring 2038 protecting the pump chamber from external fluid (shown in FIGS. 3A-B).

As discussed above, FIGS. 3A-B are an illustration of one type of pump housing 680 that could be used with medicament cartridges and the needle connector assemblies (shown in FIGS. 1A-2C) showing the reservoir and inlet connector sub-assemblies (in FIG. 3A) partially loaded into the pump housing 680 and fully loaded into the pump housing 580 with the threaded coaxial caps 2030, 2130 completely screwed into the pump housing 580. In some embodiments, the pump 651 has a display 652 that can provide digital feedback to the user regarding, for example, blood glucose levels, remaining medicament amounts, battery life, etc.

In some embodiments, the fully assembled cartridge, needle connector, and tubing system (comprising a straight, beveled, hollow, stainless steel needle, a cartridge fastened to the needle connector with a capture-and-locking feature, tubing, and a threaded coaxial cap), inserts into a pump chamber of a pump housing that contains corresponding cavities, grooves, keyways, or slots to match the unique differentiating tabs, features, or protrusions on the needle connector (as shown in FIGS. 3A-3B). In some embodiments, the threaded coaxial cap then screws into threads in the pump housing, as shown in FIGS. 3A and 3B.

In some embodiments, the reservoirs can comprise a sticker, engraving, or label that comprises a readable code (e.g., a quick response code, matrix barcode, sku, barcode, image, other computer readable code, etc.). In some embodiments, the pump 651 comprises a reader (e.g., an optical reader, scanner, etc., not shown) that reads the readable code when the reservoir is inserted into a pump chamber (e.g., a pump receptacle 660, 670). In some embodiments, where the code is recognized as being incorrect for a particular chamber or setting of the pump, the pump does not activate or stops operation (e.g., if the wrong code is present). In other embodiments, where the code is recognized as being incorrect for the current pump parameters (e.g., or amount of infusion per unit time, etc.), the pump is configured to automatically reconfigure to change the pump parameters to accommodate the actual medicament (e.g., cartridge) that is inserted. In some embodiments, the pump provides an indication (e.g., audible, visual, haptic, vibrational, etc.) that alerts the user that the incorrect medicament is inserted. In some embodiments, the user is then prompted to and/or is able to select a new setting for the pump to accommodate the new medicament (e.g., from a drop-down display on an LCD screen of the pump, etc.). In some embodiments, software and/or a computer application activates adjust the pump parameters to accommodate the medicament that has been inserted. For illustration, in some embodiments, where the pump is configured to inject U100 insulin, but reads that U200 cartridge is inserted, the pump can change the delivery parameters to accommodate proper delivery of the U200 insulin from its reservoir. As another illustration, in some embodiments, where the pump is configured to inject a rapid-acting insulin, but reads that ultrarapid-acting insulin cartridge is inserted, the pump can change the delivery parameters to accommodate proper delivery of the ultrarapid-acting insulin from its reservoir.

Figures 4A, 4B:
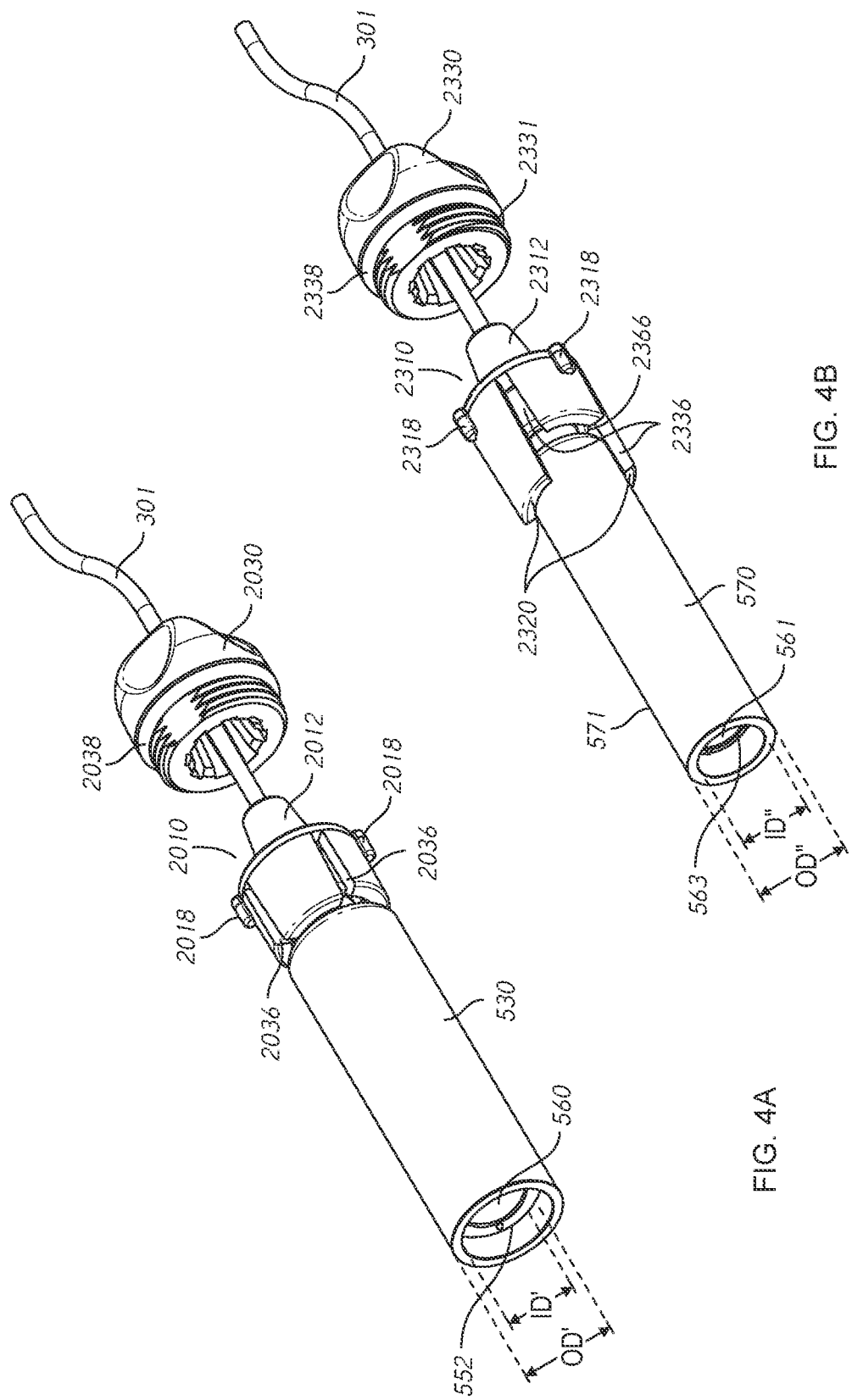
FIGS. 4A-4B illustrate embodiments of inlet connectors, inlet connector covers, medicament reservoirs, and components thereof.

FIGS. 4A-B provide isometric views showing an embodiment with two cartridges and needle connector assemblies. In some embodiments, as shown in FIGS. 4A-B, the first medicament reservoir 530 has a larger outer diameter (OD') and a larger inner diameter (ID') than the second medicament reservoir 570 outer diameter (OD") and inner diameter (ID"), respectively. In some embodiments, the inlet connector 2310 has skirt features. When used with the smaller diameter cartridge 570, the inlet connector 2310 has skirt features 2320 that extend past the shoulder of the cartridge and hug the smaller diameter cartridge wall/body 571 closely. In some embodiments, accidental attempts to connect such an inlet connector 2310 with skirt features 2320 to a cartridge whose outer diameter is larger than that of the intended cartridge would be halted by the skirt features 2320 such that the capture-and-locking features (e.g., projection mate 2366) of the inlet connector 2310 would not be able to snap into place or engage the underside of the aluminum crimp seal 536 of the first medicament reservoir 530 (shown in FIGS. 2A-B) and the straight, beveled, hollow, stainless steel needle of the inlet connector 2310 (not shown) would not penetrate the cartridge septum 534 (shown in FIG. 2A) of the larger diameter cartridge 530. In this way, misconnection of a needle connector 2310 to a cartridge with a larger diameter than the intended cartridge is prevented (not shown). Furthermore, the pump housing can be designed such that the cartridge 530 with a larger diameter is unable to fit into the pump chamber/receptacle intended for the smaller diameter cartridge. In some embodiments, the drive nut on the lead screw inside the pump chamber intended for the larger diameter cartridge cannot fit into the lumen of the smaller diameter cartridge 570 (not shown) because the internal diameter ID" is smaller than the drive nut. In this way, delivery of fluid when a cartridge is loaded into the wrong pump chamber is prevented.

In some embodiments involving two medicaments, the cartridge (e.g., cartridge A) containing one medicament (e.g., medicament A) has larger internal and external diameters than the corresponding diameters of the other cartridge (e.g., cartridge B) containing the other medicament (e.g., medicament B) (as shown in FIGS. 4A-B), such that cartridge A containing medicament A will not fit into the pump chamber intended for cartridge B containing medicament B, and the drive nut 2700 at the end of the lead screw 2701 (shown in FIGS. 6F-6G) in the pump chamber intended for medicament A is too large to fit into cartridge B containing medicament B.

In some embodiments involving two medicaments, the needle connector intended for cartridge B contains a skirt feature 2320 (as shown in FIG. 4B) that prevents the needle connector intended for cartridge B from penetrating and/or capturing cartridge A if the needle connector intended for cartridge B is accidentally placed on cartridge A.

In some embodiments involving two medicaments, the diameter of the aluminum crimp seal around the crown of one cartridge is identical to that of the other cartridge, but the height of the aluminum crimp seal around the crown of cartridge B is greater than that of cartridge A, such that the capture-and-locking feature 2366 within the needle connector 2310 intended for cartridge A will not be engaged if the needle connector intended for cartridge A is accidentally placed on cartridge B (not shown).

In some embodiments, as shown in FIGS. 1A-4B, the needle connector 2010, 2110, 2210, 2310 has any number of unique differentiating tabs, features, or protrusions, as shown in embodiments, which would allow insertion into the pump chamber of a pump housing that contains corresponding cavities, grooves, keyways, or slots to match with the unique differentiating tabs, features, or protrusions on the needle connector. In this way, only one type of needle connector can be inserted uniquely into one particular pump chamber. Alternatively, the needle connector might contain any number of cavities, grooves, keyways, or slots (not shown) that uniquely mate with tabs, features, or protrusions in the pump chamber of a pump housing.

Throughout this disclosure, similar features for separate embodiments of a device component (e.g., inlet connectors, inlet connector covers, etc.) can comprise one or more coinciding features offset numerically by a factors of 100 but having the same tens numerical value. For example, features of inlet connector 2030 that coincide to similar features of another connector 2130 will be offset by a 100, respectively (e.g., feature 2012 corresponds to 2112, etc.).

In some embodiments (as shown in FIGS. 1A-4B), a straight, beveled, hollow, stainless steel needle is overmolded, bonded, press-fitted, glued, solvent bonded, insert molded, or otherwise attached to the inside of the needle connector 2010, 2110, 2210, 2310 and tubing 301 is overmolded, bonded, press-fitted, glued, solvent bonded, insert molded, or otherwise attached to the needle connector 2010, 2110, 2210, 2310 and to the straight, beveled, hollow, stainless steel needle in such a way as to allow a closed, independent, patent, and continuous fluid path through the straight, beveled, hollow, stainless steel needle, the needle connector, and the tubing. In some embodiments, the straight, beveled, hollow, stainless steel needle is recessed within the needle connector 2010, 2110, 2210, 2310 so as to be touch-proof.

In some embodiments, the tubing 301 passes through a threaded coaxial cap 2030, 2130, 2230, 2330, which is free to slide up and down the threaded coaxial cap and thread into a pump housing.

In some embodiments, the fully assembled cartridge assembly, comprising a cartridge, needle connector, and tubing system (consisting of a straight, beveled, hollow, stainless steel needle, a cartridge fastened to the needle connector with a capture-and-locking feature, tubing, and a threaded coaxial cap, as shown in FIGS. 2A-4B), inserts into a pump chamber of a pump housing that contains corresponding cavities, grooves, keyways, or slots to match the unique differentiating tabs, features, or protrusions on the needle connector. The threaded coaxial cap then screws into threads in the pump housing, as shown in FIGS. 3A-B.

Figure 5C:
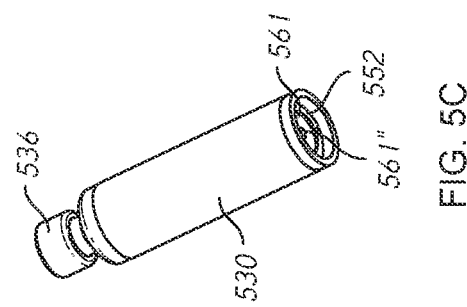
FIGS. 5A-5C illustrate a system for filling a medicament reservoir.
Figure 5B:
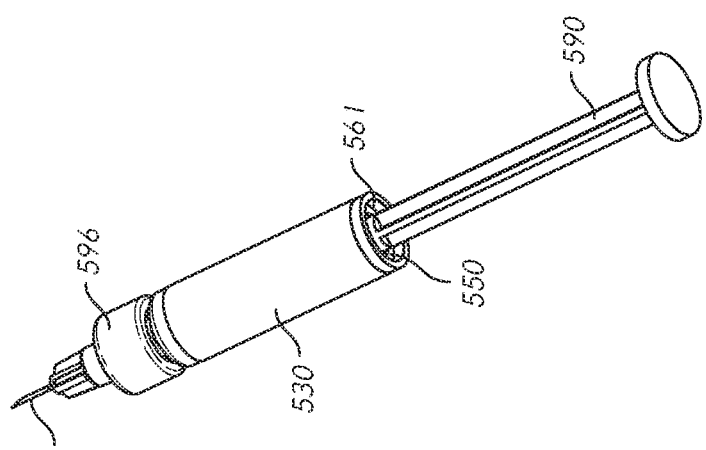
Figure 5A:
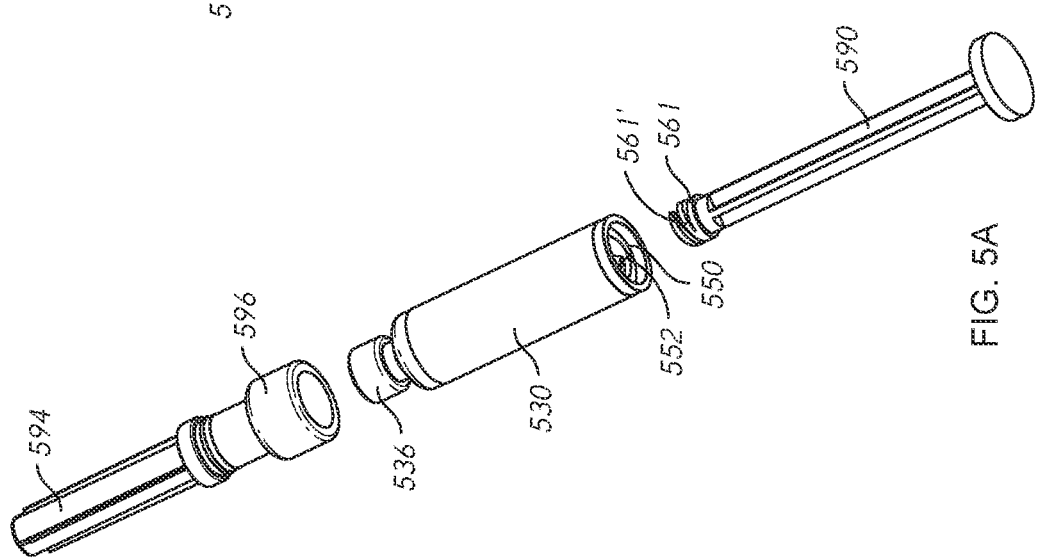

In some embodiments, a medicament reservoir filling system and method of using the same is provided, as shown in FIGS. 5A-B. FIG. 5A shows a rotated isometric view of a cartridge filling apparatus sub-assembly used to fill a medicament cartridge at the point of care. FIG. 5B shows a fillable cartridge assembly after the filling apparatus has been connected. FIG. 5C shows a fillable cartridge after the filling apparatus has been removed. In some embodiments, as shown, a fillable cartridge body 530, would be supplied and pre-assembled with the cartridge septum 534 (shown in FIG. 2A), the aluminum crimp seal 536 and the elastomeric plunger 550 with its threaded receptacle for a ferrous insert 552 exposed. In some embodiments, a needle transfer hub 596 containing a single needle 595 (with two beveled tips or two needles, each with a single beveled tip) would be attached to its needle guard 594 and provided along with the fillable cartridge 530. In some embodiments, a pushrod 590 would be attached to a threaded ferrous insert 561 by way of a breakable joint or threads and provided along with the fillable cartridge 530. In some embodiments, at the point of care (or at a site where filling is appropriate), the pushrod 590 would be used to thread (via an attaching feature 561') the threaded ferrous insert 561 into the threaded receptacle for a ferrous insert 552 present within the elastomeric plunger 550. In some embodiments, the needle transfer hub 596 would be then connected to the cartridge 530 such that the touch-proof needle or needle tip (not shown) within the needle transfer hub 596 would pierce the cartridge septum (shown in FIG. 2A), after which the needle guard 594 would be removed to reveal the needle or needle tip 595 designed to pierce the septum of the vial. The needle or needle tip designed to pierce the septum of the vial would then be inserted into a medicament vial (not shown), and the pushrod 590 would be used to fill the cartridge body 530 with the medicament (e.g., by inserting the needle 595 into a bulk medicament and depressing the plunger 550 into and back out of the medicament reservoir 530). After filling the cartridge 530, the needle transfer hub 596 and the pushrod 590 would be removed, revealing the threaded receptacle for a pushrod, or breakable joint remnant, and leaving the threaded ferrous insert 561 embedded within the elastomeric plunger 550 by virtue of its thread-locking barb 561'. Such a cartridge that is filled at the point of care could then be attached to a needle connector assembly (as in FIGS. 2A-C) and loaded into a pump housing (as in FIGS. 3A-B).

In some embodiments that utilize a needle transfer hub to transfer medicament from a vial to the cartridge, as in FIG. 5, a straight, beveled, hollow, stainless steel needle is overmolded, bonded, press-fitted, glued, solvent bonded, insert molded, or otherwise attached to the needle transfer hub in such a way as to allow a closed, independent, patent, and continuous fluid path through the straight, beveled, hollow, stainless steel needle. In some embodiments, the straight, beveled, hollow, stainless steel needle is beveled at both tips, where one tip would be designed to pierce the septum of the cartridge and the other tip would be designed to pierce the septum of the vial. In some embodiments, the tip that is designed to pierce the septum of the cartridge is recessed within the needle transfer hub so as to be touch-proof and the tip that is designed to pierce the septum of the vial can be concealed and protected by a needle guard which would be removed at the point of care before piercing the septum of the vial.

In some embodiments that utilize a needle transfer hub to transfer medicament from a vial to the cartridge, two separate, straight, beveled, hollow, stainless steel needles are overmolded, bonded, press-fitted, glued, solvent bonded, insert molded, or otherwise attached to the needle transfer hub in such a way as to allow a closed, independent, patent, and continuous fluid path through the straight, beveled, hollow, stainless steel needles. In some embodiments, each straight, beveled, hollow, stainless steel needle would be beveled only on one tip, where the beveled tip of one needle would be designed to pierce the septum of the cartridge and the beveled tip of the other needle would be designed to pierce the septum of the vial. In some embodiments, the tip that is designed to pierce the septum of the cartridge is recessed within the needle transfer hub so as to be touch-proof and the tip that is designed to pierce the septum of the vial can be concealed and protected by a needle guard which is to be removed at the point of care before piercing the septum of the vial. Alternatively, in some embodiments, the tip that is designed to pierce the septum of the vial can also be recessed so as to be touch-proof and a needle guard may not be supplied.

In some embodiments, involving two medicaments, mis-channeling of medicaments can still be avoided if cartridge B is pre-filled with one medicament and cartridge A is filled at the point of care with a different medicament (using the embodiment described in FIGS. 5A-C). In some embodiments, as long as only one cartridge needs to be filled with one medicament at the point of care, and the other cartridge is pre-filled with another medicament, the designs described here can prevent medicament mischanneling. In some embodiments involving two medicaments, both cartridge A and cartridge B are pre-filled with medicament A and medicament B, respectively. In some embodiments involving two medicaments, cartridge A is filled at the point of care with medicament A and cartridge B is pre-filled with medicament B.

In some embodiments, the same dual-medicament infusion system could use identical needle sites, connectors, tubes, and cartridges in the configuration where both cartridge A is pre-filled with medicament A and cartridge B is pre-filled with medicament B, as in the configuration where cartridge A is filled at the point of care with medicament A and cartridge B is pre-filled with medicament B (or vice versa).

In some embodiments (as in FIGS. 5A-C) that require one cartridge to be filled at the point of care, medicament is transferred from a vial containing the medicament into the cartridge by way of a needle transfer hub and a pushrod that is connected to the elastomeric plunger residing in the cartridge by way of a breakable joint or threads such that the pushrod can be disconnected and discarded (or reused) upon completion of the filling procedure.

In some embodiments (as in FIGS. 5A-C) involving a cartridge containing a ferrous insert, the pushrod can be connected directly to the ferrous insert by means of a breakable joint or threads. Upon completion of the filling procedure, the pushrod can be disconnected and discarded (or reused), leaving the ferrous insert embedded within the elastomeric plunger. In some embodiments, in the case of a threaded connection between the ferrous insert and the pushrod, the threads on the ferrous insert could have a uni-directional burred surface (as in FIGS. 6A-F) that would allow it to easily thread into the elastomeric plunger, but would resist being threaded out of the elastomeric plunger. Whereas the threads on the pushrod would be smooth, and would not contain such a uni-directional burred surface (or other traction or frictional element), it would thread into and out of the ferrous insert easily, and without the ferrous insert threading out of the elastomeric plunger once the ferrous insert is fully threaded into the elastomeric plunger.

In some embodiments, as shown in FIG. 6A, a front view of the threaded ferrous insert 561, the insert 561 (e.g., ferrous insert) has a thread-locking barb 561'. An isometric view of the threaded ferrous insert 561 is shown in FIG. 6B with a threaded receptacle for a pushrod 561" and FIG. 6C shows an embodiment 560 without a threaded receptacle for a pushrod. FIG. 6D is a front view of the snug-fit metal insert 563 showing a thread-locking barb 563'. FIG. 6E is an isometric view of the snug-fit metal insert 563. FIG. 6E shows a threaded receptacle 563" for a pushrod. FIG. 6F shows an embodiment of a snug-fit insert 562 without a threaded receptacle for a pushrod. In some embodiments, the ferrous insert that is used to facilitate magnetic coupling between a magnet at the end of the drive nut in a pump chamber and the elastomeric plunger could be attached to the elastomeric plunger by way of threads (as in A, B, and C) or by way of snug-fit or snap-fit (as in D, E, and F). Regardless of the method of attachment to the elastomeric plunger, the ferrous insert could have a threaded receptacle for a pushrod (as in B and E). In some embodiments, in cases where a threaded receptacle for a pushrod is present, a pushrod could be pre-assembled with the ferrous insert. This sub-assembly could then be attached to the elastomeric plunger, either by way of threads, snug-fit, or snap-fit, and the pushrod could be used to fill an empty medicament cartridge. Upon filling the medicament cartridge, the pushrod could be detached from the ferrous insert while leaving the ferrous insert embedded within the elastomeric plunger (as in FIG. 5C). The metal insert may have thread-locking barbs to prevent the metal insert from backing out or rotating with the pushrod as the latter is being removed.

In some embodiments, as discussed elsewhere herein, a magnetic coupling between a magnet (or magnetic portion) at the end of the drive nut 2700 (located in a pump chamber of a pump) and the elastomeric plunger 550 occur to prevent inadvertent departure (or lift-off) of the elastomeric plunger 550 from the drive nut 2700. This coupling advantageously prevents the plunger from moving and distributing medicament in an uncontrolled and/or undesired way. For instance, medicament vials having plungers are typically designed to have little or no resistance and/or friction between the plunger and the wall of the reservoir. Thus, the plunger can move and distribute medicament with very little force applied to the plunger (e.g., even by moving the cartridge). In some embodiments, configurations described herein avoid issues with low friction plungers by coupling (e.g., magnetically) the plunger to the drive nut. In some embodiments, as discussed elsewhere herein, a ferrous insert 565 can be screwed into the plunger 565 of the cartridge 530. In some embodiments, a perceivable click (by touch, sound, etc., or other indication as described elsewhere herein) occurs when the magnetic tip of the drive nut and the magnetic insert come into contact. This click and/or mating can indicate to a user that the vial is properly placed in the pump.

Figure 6G:
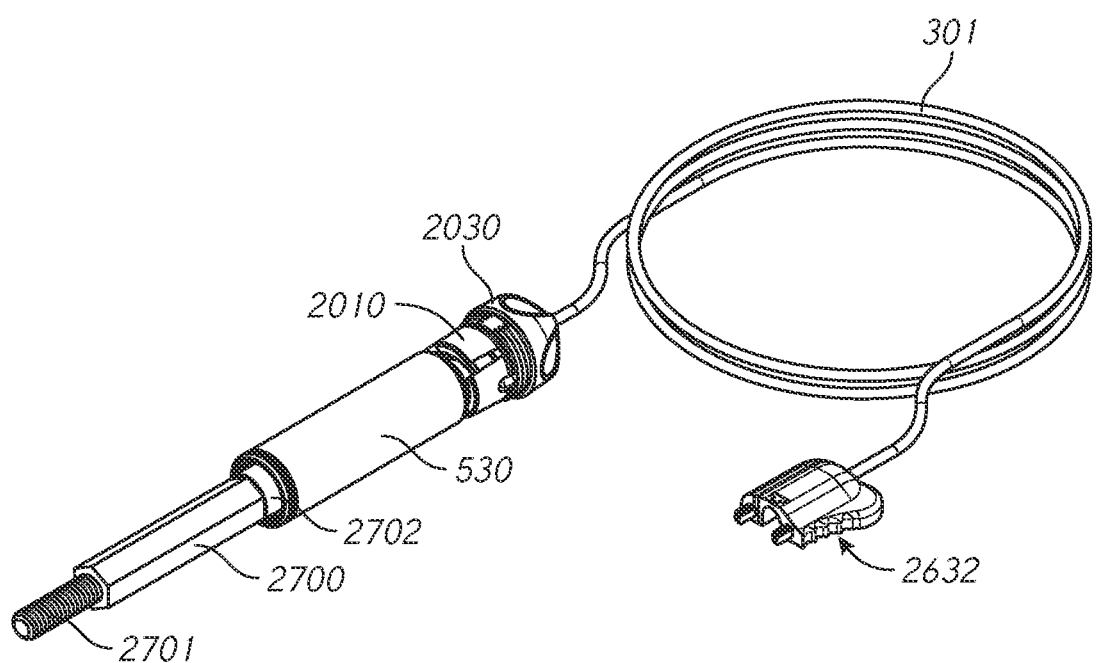
FIG. 6G illustrates an embodiment of drive nut interacting with a medicament reservoir coupled to a connector set, a fluid conduit, and an infusion site connector.
Figure 6H:
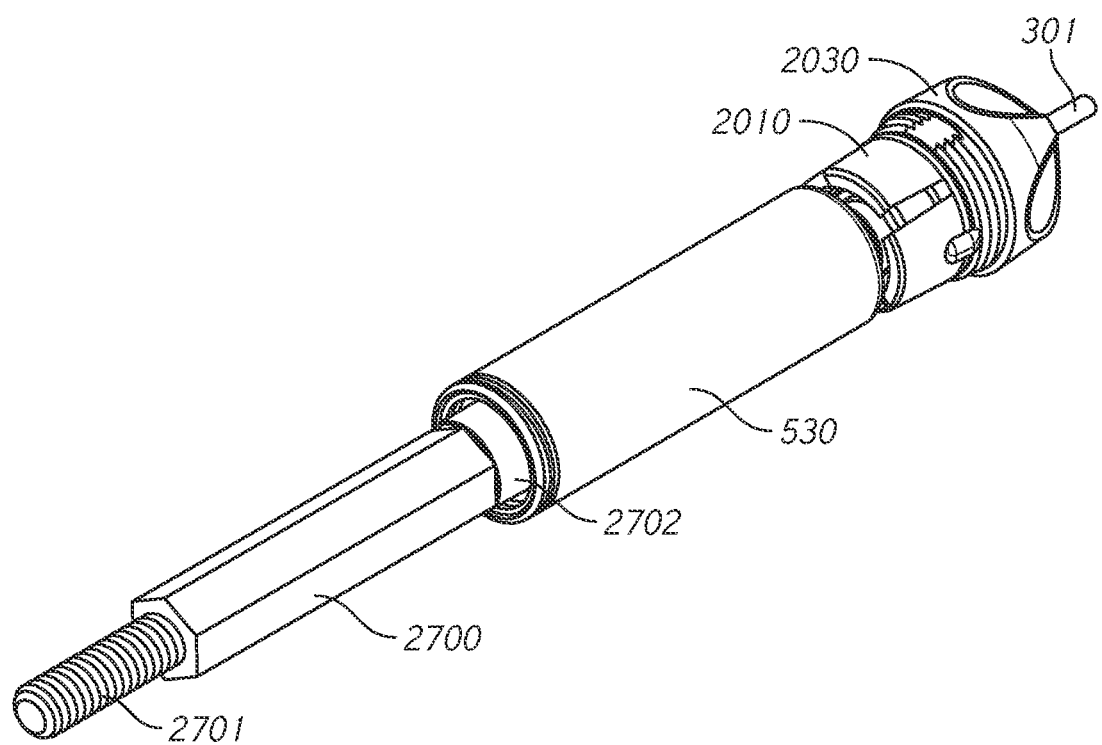
FIG. 6H is an expanded view of the drive nut, medicament reservoir, and connector set depicted in FIG. 6G.
Figure 6I:
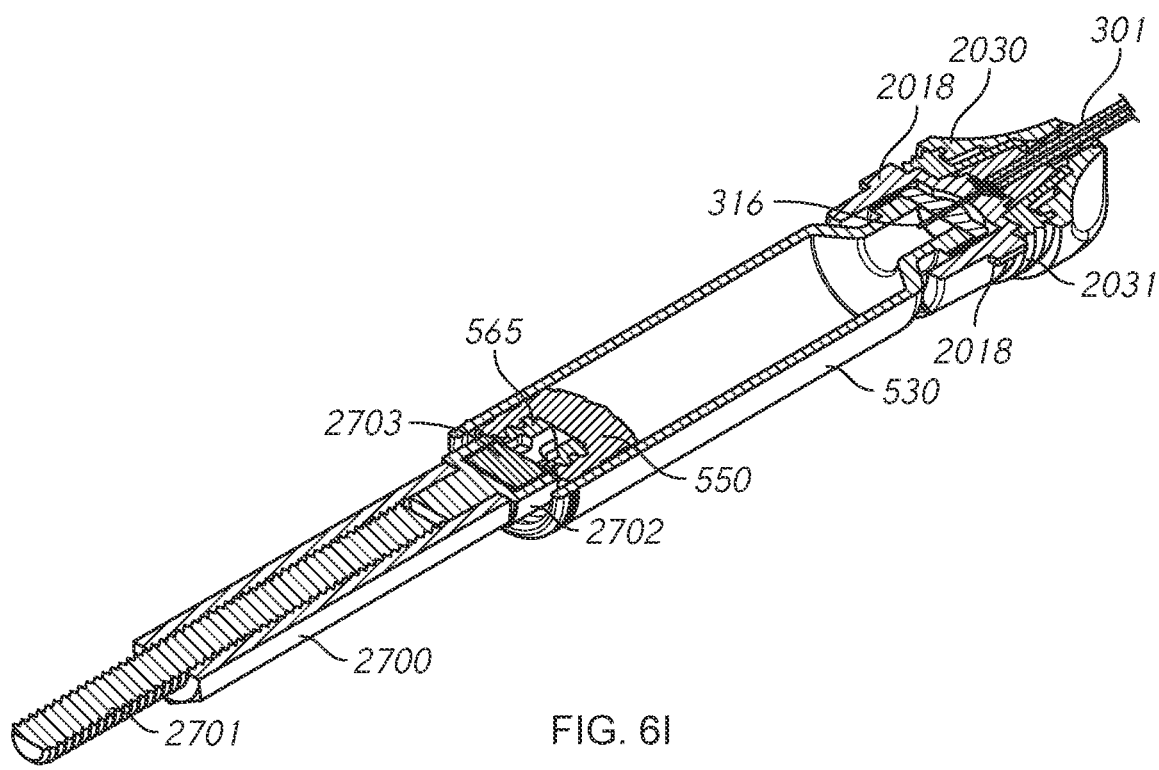
FIGS. 6I and 6J illustrate bisected views of the assembly of FIG. 6H.

FIGS. 6G-6H show a drive nut 2700 engaging with a medicament reservoir 530 via a magnetic tip 2702 of the drive nut. The drive nut 2700 comprises a lead screw 2701 that interacts with a driver in a pump (not pictured) to advance the drive nut forward, urging a plunger into the reservoir 530. In some embodiments, as discussed elsewhere herein, a magnetic insert can be placed in the plunger of the reservoir (e.g. screwed-in). In some embodiments, a frictional element (e.g., by a barb, etc.) can affix the insert in the plunger (so that the insert will not back-thread out of the plunger, for example). In some embodiments, as described above, the magnetic insert 565 could be connected to the elastomeric plunger 550 by means of a snug-fit, snap-fit, and/or with a barb. In some embodiments, the tip of the drive nut comprises a magnetic material (e.g., a ferrous metal) and the insert comprises a magnet. A configuration of a magnetic insert 565 inserted into a plunger 550 that is in magnetic communication with a magnetic tip 2702 of a drive bolt 2700 is shown in FIGS. 6H-6I.

In some embodiments, the magnetic insert 565 (e.g., ferrous insert) can be injection-molded and/or can comprise, in part, a curable material that is cured during fabrication. In some embodiments, during fabrication of the magnetic insert 565, a curable material (e.g. uncured plastic, rubber, elastomer, polymer, epoxy, composite, etc.) is mixed with a magnetic material (e.g., a ferrous material, metal shavings, metal beads, metal powder, etc.). During mixing, the magnetic material can be distributed homogeneously and/or as a gradient throughout the curable material. In some embodiments, the curable material can then be cured to provide a magnetic insert 565 with magnetic material distributed within the cured material.

In some embodiments, by using a polymeric insert (e.g., plastic, rubber, elastomer, composite, etc.) that is loaded with magnetic material (e.g., a ferrous material, metal shavings, metal beads, metal powder, etc.), a desired strength of association between the magnetic tip 2702 and the magnetic insert 565 can be achieved. In some embodiments, a tailored magnetic coupling between the insert 565 and the magnet 2703 at the magnetic tip 2702 of the drive nut 2700 (as shown in FIGS. 6G-6K) can be achieved by adjusting the concentration of magnetic material in the insert 565 and/or by adjusting the size and/or strength of the magnet 2703. In some embodiments, the magnetic interaction can be of sufficient strength such that the magnetic coupling would avoid inadvertent departure, separation, or lift-off of the plunger 550 from the drive nut 2700 thereby decreasing the threat of unintentional medicament delivery. In some embodiments, the magnetic properties of the tip and the magnetic material of the plunger (or insert) can be tailored so that they are strong enough to associate with one another, but not so strong that the magnetic material interacts with objects outside the pump (e.g., objects other than the magnetic tip 2702 and the drive nut 2700).

In some embodiments, the magnetic material can be directly dispersed within the plunger 550 during fabrication of the plunger. For example, during fabrication of the plunger, magnetic properties can be added to the plunger material prior to and/or during molding. In some embodiments, this obviates the need for insert 565 having magnetic properties. In some embodiments, this advantageously simplifies the system and avoids additional steps needed for coupling an insert to a plunger.

In some embodiments, using an insert with magnetic properties that is placed within plunger advantageously prevents contact between the medicament in the reservoir and the magnetic material. In some embodiments, using an insert 565 with magnetic properties in the plunger 550 (instead of a magnetic material distributed in the plunger) advantageously prevents leaching of the magnetic material into the medicament by preventing contact between the magnetic material and the medicament. In some embodiments, using an insert configuration also improves the integrity of the reservoir. In some embodiments, for example, when the reservoir is filled by a patient or at the point of care, the plunger is depressed and retracted multiple times. In some embodiments, when distributed directly in the plunger, the magnetic material abrades the inner chamber of the vial after multiple uses. This abrasion can lead to premature failure of the vial and/or leaking of the reservoir assembly. In some embodiments, using the insert with magnetic properties in the plunger avoids this abrasion. In some embodiments, an insert having magnetic properties can be an integral, but separate, component embedded within the elastomer plunger such that there would be no need to manually insert it into the plunger at the point of care (i.e. the plunger would come with the insert already installed by the manufacturer during the fabrication of the plunger/insert assembly).

Figure 6J:
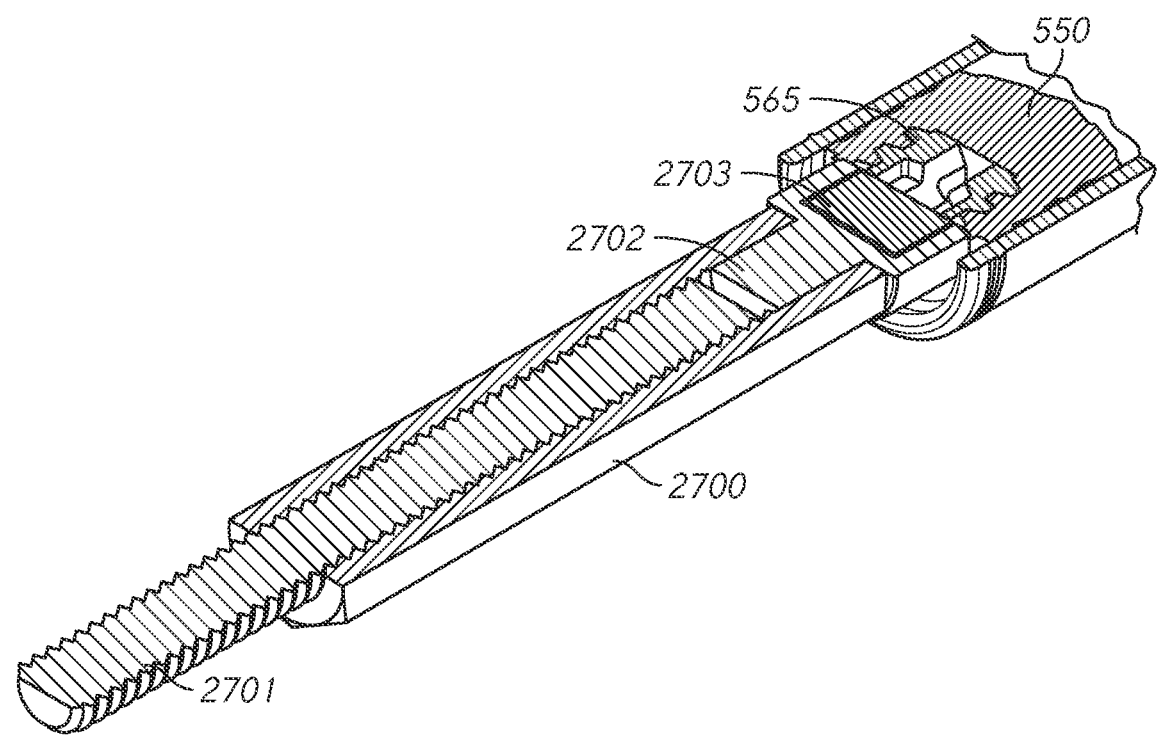
Figure 6K:
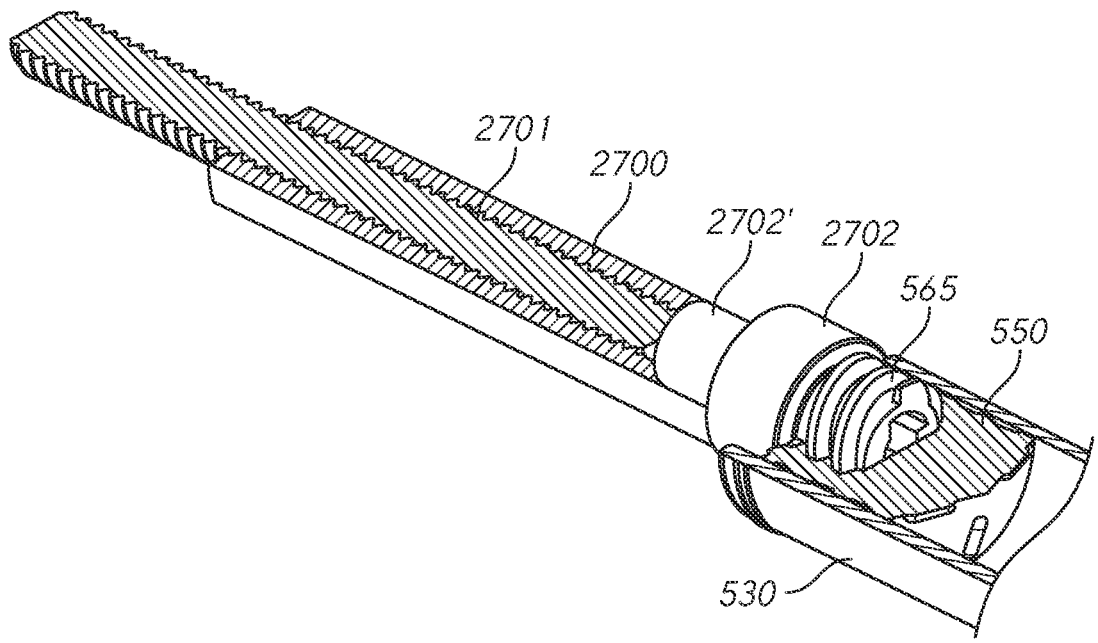
FIG. 6K illustrates a bisected view of the assembly of FIG. 6H where the tip of the drive nut and the insert of the reservoir are not bisected.
Figure 6L:
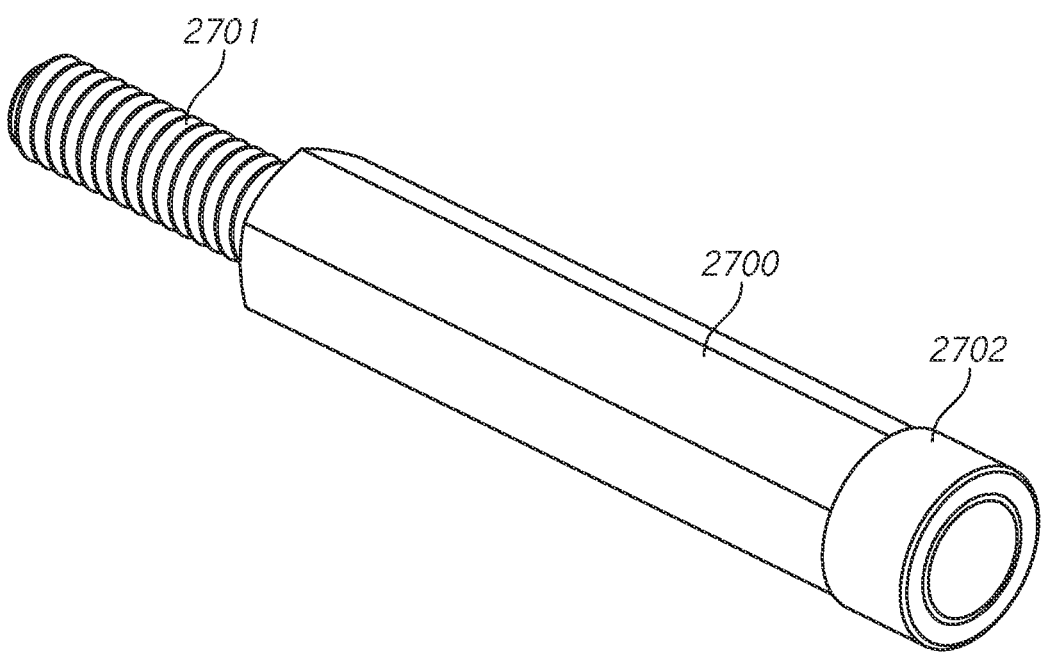
FIG. 6L illustrates an expanded view of a drive nut and its tip.

FIGS. 6I-6J show a bisected view of the drive nut 2700 engaging an insert having magnetic properties 565 via the tip 2702 of the drive nut 2700. As shown, the tip 2702 can comprise a magnet 2703 that interacts and/or connects to the insert having magnetic properties 565 of the plunger 550 within the reservoir 530. FIG. 6K shows a partially bisected view of the drive nut 2700 engaging an insert having magnetic properties 565 via the tip 2702 of the drive nut 2700. In FIG. 6K, the tip 2702 is not bisected, nor is the insert having magnetic properties 565. As shown the tip 2702 can include a protrusion 2702' (e.g., a handle, spike, projection, etc.) that inserts into the drive nut 2700 to hold the tip 2702 in place. FIG. 6L shows the drive nut assembly, including the drive nut 2700 and the lead screw 2701 and the tip 2702 removed from the pump housing.

Figure 6M:
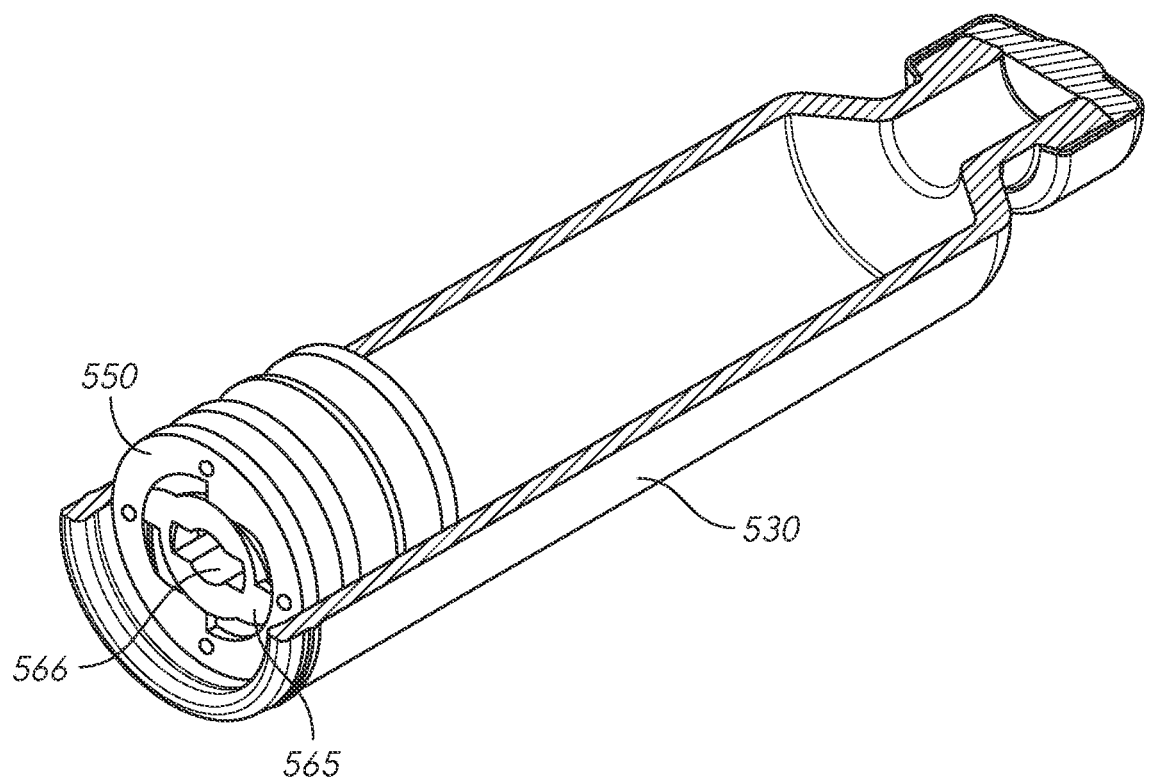
FIG. 6M illustrates a bisected view of an embodiment of a medicament reservoir where the plunger and insert of the reservoir are not bisected.
Figure 6N:
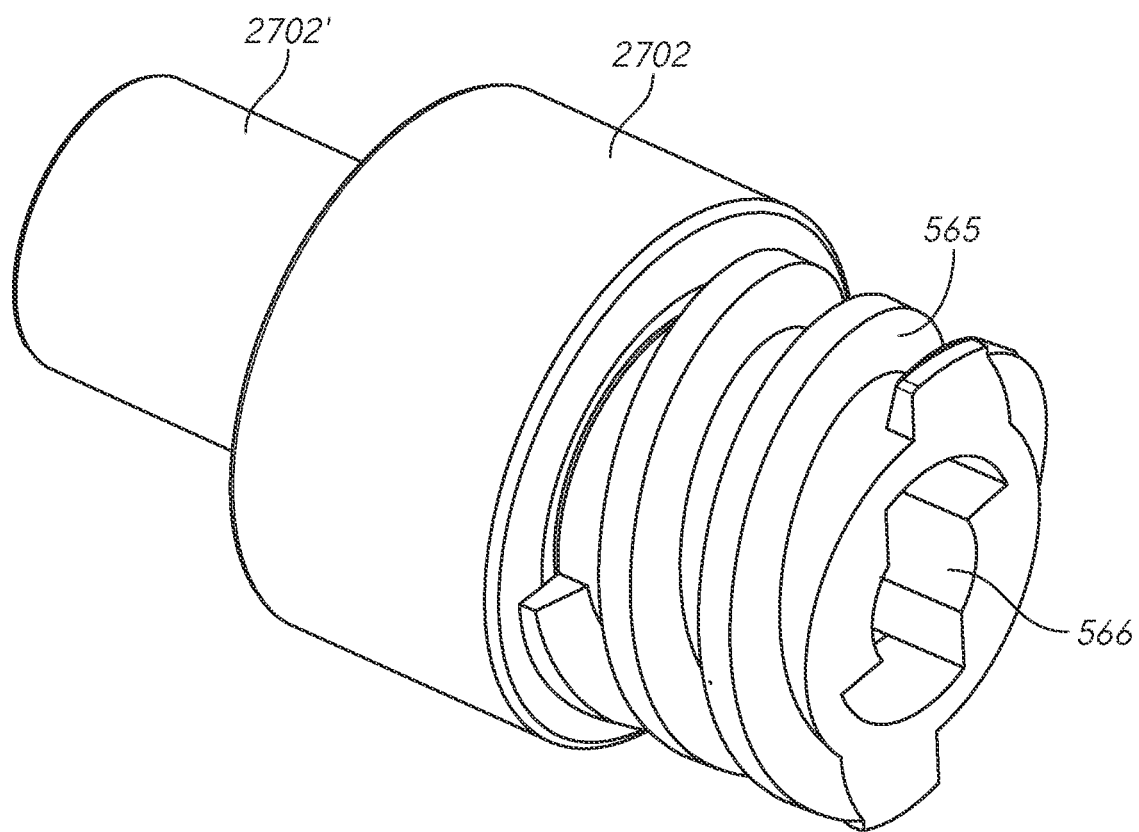
FIG. 6N illustrates a view of an embodiment of a drive nut tip and an insert.
Figure 60:
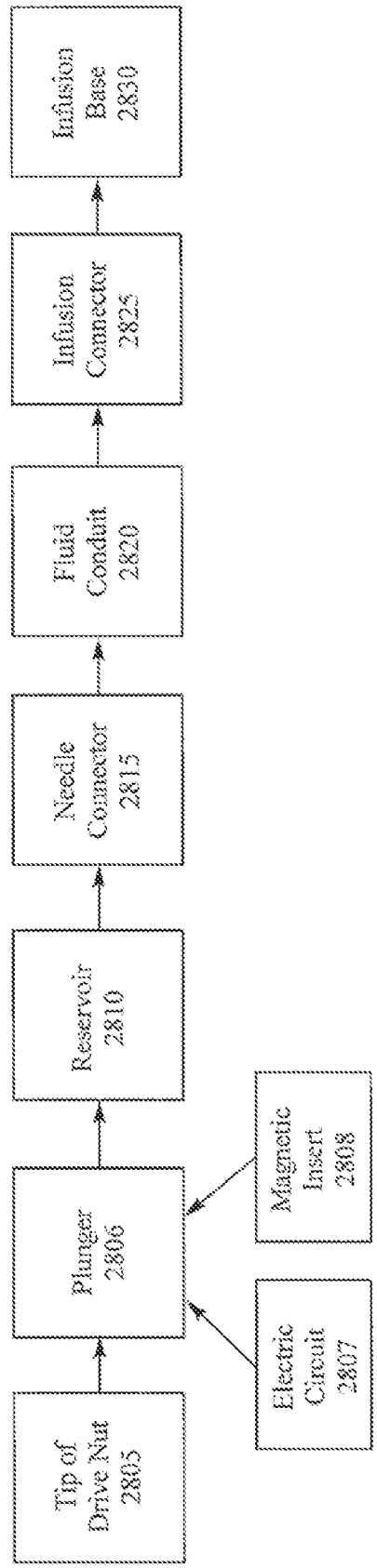

FIG. 6M shows another partially bisected view. In FIG. 6M, the insert having magnetic properties 565 in the plunger 550 is shown in the reservoir 530. As shown, similar to the insert shown in FIG. 6B, in some embodiments, the insert 565 can comprise an aperture 566 (e.g., a connector, a hole, a fixing point, locking mechanism, etc.) that allows engagement of a push rod (not shown). As described elsewhere herein, in some embodiments, at the point of care (or at a site where filling is appropriate), the pushrod 590 would be used to thread (via a receptacle for a pushrod 566) the threaded insert having magnetic properties 565 into the threaded receptacle for an insert present within the elastomeric plunger 550. FIG. 6N is a view of the magnetic tip 2702 in magnetic contact with the insert having magnetic properties 565. The aperture 566 is also shown. In some embodiments, the pushrod 566 can be used to install the insert 565 into the plunger 550.

In some embodiments, a method of detecting and continuously monitoring contact between the elastomeric plunger or insert 565 and the drive nut 2700 in each pump chamber is provided. In some embodiments, for instance, the insert 565 (or plunger) is made of electrically conductive plastic (e.g., a plastic containing carbon fibers, metal strands, shavings, copper filings, etc.) and it serves as a conducting element that can complete a passive electrical circuit. In some embodiments, mating components of the passive circuit could be installed on the tip 2702 of the drive nut 2700 in each pump chamber. In some embodiments, the passive electrical circuit on the tip 2702 of the drive nut 2700 could be powered remotely by an active circuit installed somewhere within the pump housing (e.g. using some form of radiofrequency identification or "RFID" such as a near-field communication protocol). In some embodiments, in the absence of the electrically conductive insert 565 (or plunger), current would not flow through the passive electrical circuit on the tip 2702 of the drive nut 2700. In some embodiments, contact between the electrically conductive insert 565 (or plunger) and the passive electrical circuit on the tip 2702 of the drive nut 2700 would close the passive circuit and allow current to flow through the passive circuit and through the electrically conductive insert 565 (or plunger).

In some embodiments, the change in status from a no-current-flow state to a current-flow state would correspond to a change in status from a no-contact to a contact configuration between the electrically conductive insert 565 (or plunger) and the tip 2702 of the drive nut 2700. In some embodiments, if a drug cartridge is placed into the pump chamber and the insert 565 is not present, this detection mechanism could place the pump into a fault state. In some embodiments, the fault state could prevent the pump from operating (preventing medicament flow). In some embodiments, the fault state triggers an alarm feature that could alert the user of the error (e.g., a vibration, audible alarm, visual alarm, etc.). In some embodiments, if the elastomeric plunger 565 lifts off of the drive nut 2700 during operation, this detection mechanism could also place the pump into a fault state, and an alarm could alert the user of the error.

In some configurations, the elastomeric plunger insert 550 (shown in FIGS. 6I-6J) could be made of an electrically conductive material having magnetic properties (such as an electrically conductive plastic loaded with ferrous material). In some embodiments, if a passive electrical circuit were installed on top of a magnet 2702 located at the tip of the drive nut 2700, then an active circuit (installed somewhere within the pump housing) could communicate (e.g., through RFID) to remotely power the passive circuit and detect whether or not there is contact between the elastomeric plunger 550 (and/or the insert 565) and the tip 2702 of the drive nut 2700. In some embodiments, at the same time, the magnet could be used to capture the insert and elastomeric plunger assembly (as described previously). In this way, the same insert could simultaneously serve as an integral component of the elastomeric plunger capture mechanism and the elastomeric plunger detection mechanism described previously. This embodiment is shown schematically in FIG. 6O. The infusion system can comprise one or more of a pump with a drive nut having a tip 2805 that interacts with a plunger 2806 of a reservoir 2810. In some embodiments, as the tip of the drive nut 2805 engages and pushes the plunger 2806, it advances the plunger 2806 into the reservoir 2810 which distributes a medicament via a needle connector 2815 into a fluid conduit 2820 to an infusion connector 2825 that connects to an infusion base 2830. The infusion base 2830, as discussed elsewhere herein, can distribute the medicament into a patient (e.g., through a needle or catheter). As shown in the schematic of FIG. 6O, in some embodiments, the components of the electric circuit 2807 can be separate from the magnetic insert 2808 in the plunger 2806.

Figure 6P:
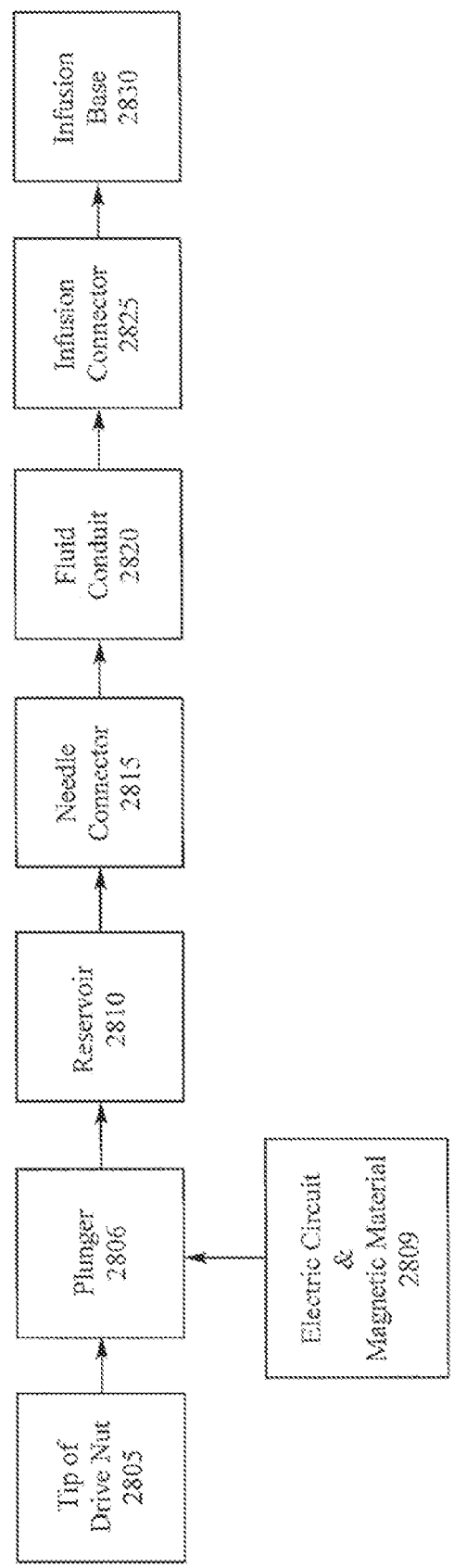
Figure 6Q:
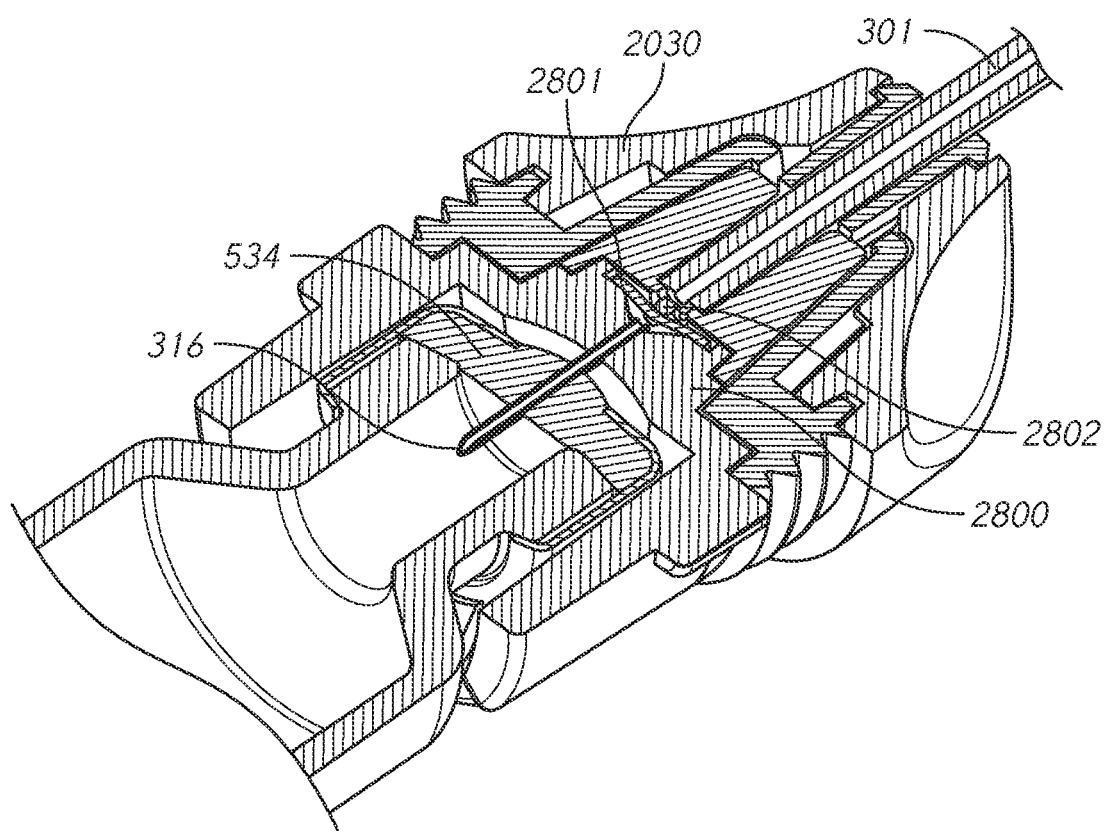
FIGS. 6Q-6T illustrate a resisting feature installed within a needle connector.
Figure 6R:
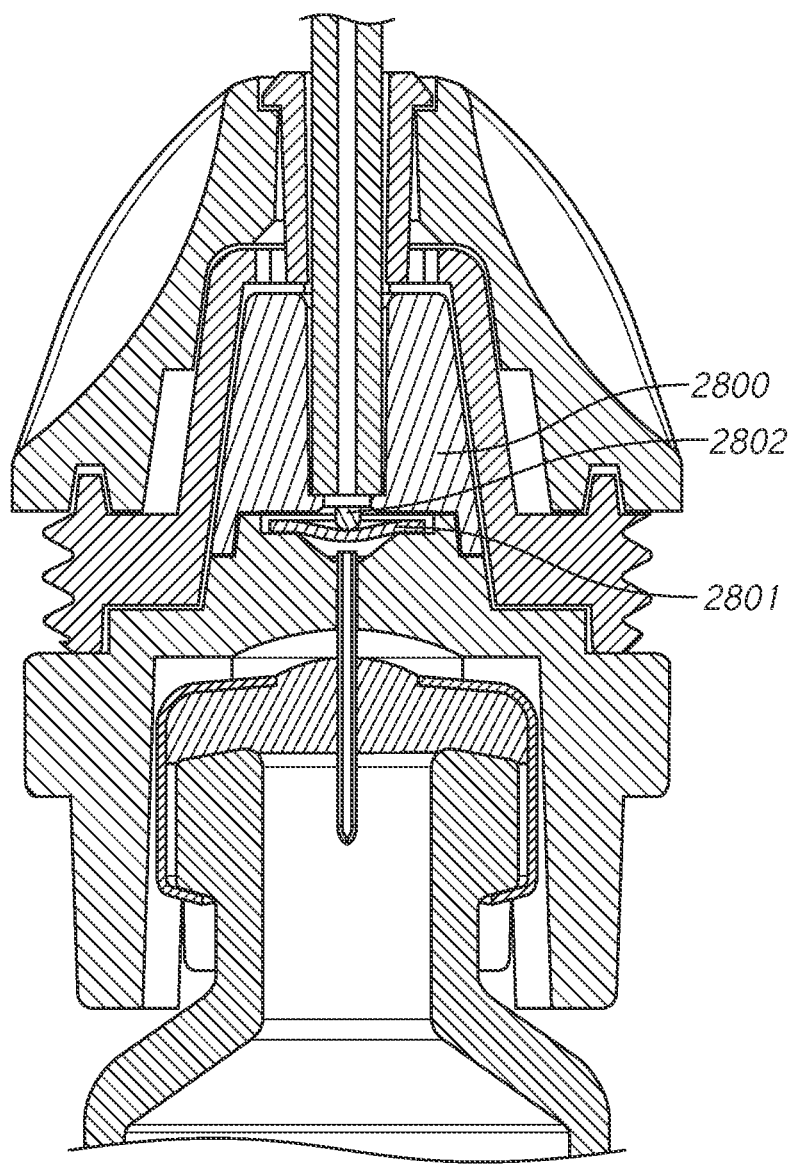
Figure 6S:
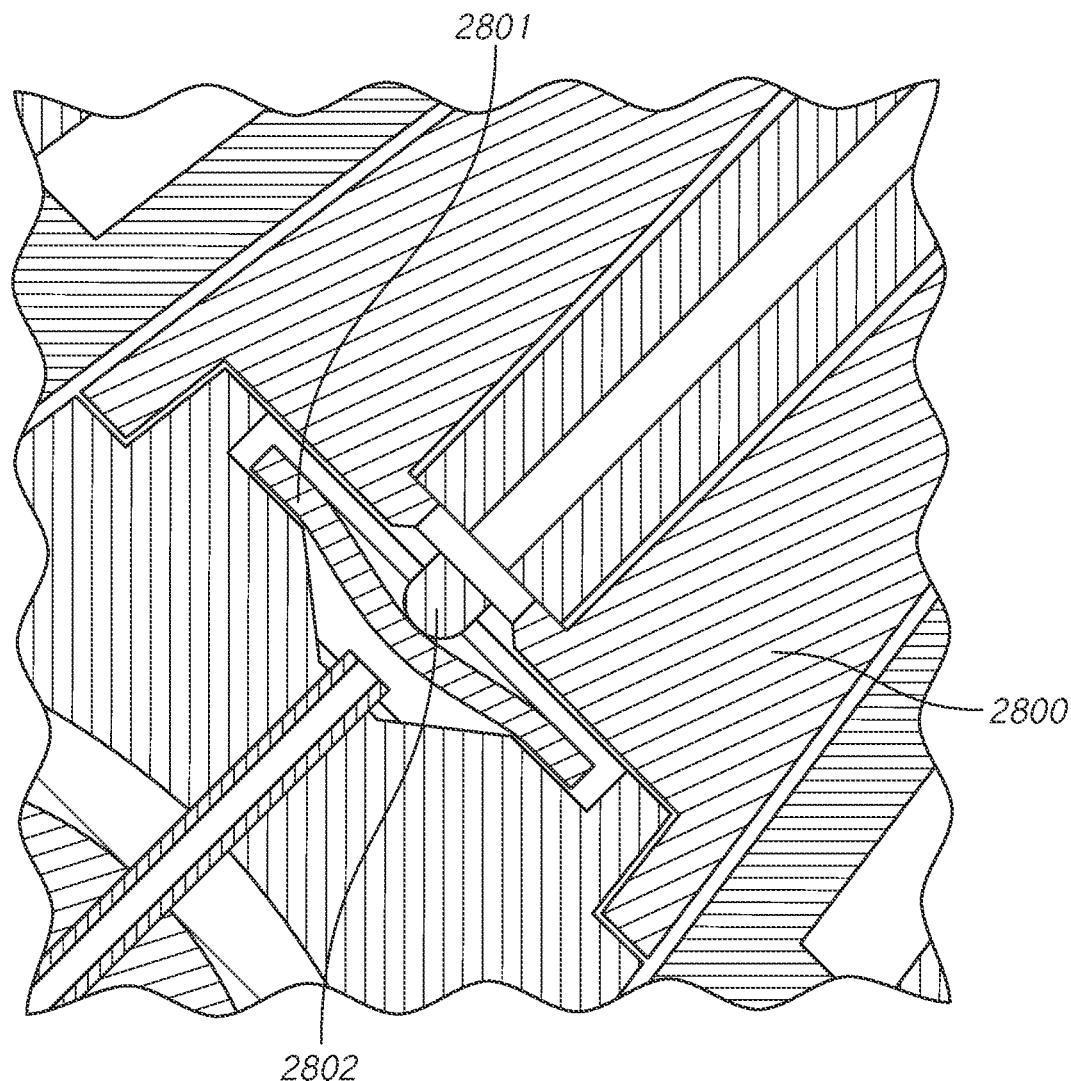

In some embodiments, as an alternative configuration and as shown in FIG. 6P, a passive electrical circuit could be embedded in the insert (rather than on the tip of the drive nut 2700). In some embodiments, the passive electrical circuit also has magnetic properties and the magnet on tip 2702 of the drive nut 2700 could be electrically conductive. In this way, contact between the passive electrical circuit embedded in the insert and the electrically conductive magnet on the tip 2702 of the drive nut 2700 would close the passive circuit and allow current to flow through the passive circuit and through the electrically conductive magnet, thereby changing the status from a no-contact to a contact configuration between the passive electrical circuit embedded in the insert and the head of the electrically conductive magnet located at the tip 2702 of the drive nut 2700.

Additionally, the electric circuit configuration can allow users to avoid inserting incorrect cartridges (e.g., medicament vials) into the pump and using them with the infusion system. For example, if a user attempts to insert a vial having medicament reservoir with the incorrect plunger into the pump (e.g., a reservoir lacking a magnetic and/or conductive insert), the pump remains in the no-contact mode and does not distribute the medicament. In some embodiments, this feature can also act as a safe guard to ensure that only proper vials are used in appropriate ports of the pump (avoiding mischanneling, etc.). This feature can help avoid distribution of the incorrect medicament to a patient.

In some embodiments, an alternative and/or additional method for detecting the presence of the plunger of a cartridge (and/or the presence of a cartridge itself), is to initiate a detection sequence before attempting to administer a dose. For example, in some embodiments, the detection sequence can involve applying a limited driving electrical current. In some embodiments, the limited driving electrical current could be one that is just sufficient to advance the drive nut when not in contact with a cartridge plunger. In other words, the limited driving electrical current could be one that is insufficient to advance the drive nut when in contact with the cartridge plunger. In some embodiments, for example, where the plunger is present, it has sufficient static friction and/or flow resistance downstream (whether due to friction within the cartridge body, neck, connector, or connected tubing, and/or from added features within these components, such as a check valve, etc.) and resists and/or substantially prevents the advancement of the drive nut. In some embodiments, once the plunger is detected, the electrical current can detectably ramp up and/or enter a delivery mode (where the pump is configured to distribute medicament into the patient). In some embodiments, this detection process could be repeated just in advance of each medicament dosing attempt to ascertain whether or not the plunger (and/or an appropriate plunger) and/or insert is present and/or in contact with the drive nut. Then, depending on whether the plunger and/or insert is detected or not, the pump could respond accordingly (e.g. by dosing if plunger is detected, or by aborting the dose and/or annunciating an alarm if plunger is not detected to be present). In some embodiments, the detection sequence and the control of the electrical current described above can be implemented using a controller. The controller is described more in detail elsewhere herein.

In some embodiments, the detection sequence involves a probing sequence. In some embodiments, the probing sequence involves the advancement of the drive nut, as described elsewhere herein, to first detect the plunger. In some embodiments, once the plunger is detected, the type of plunger can be determined by retracting and advancing the drive nut incrementally until a force and/or current sufficient to just move the plunger is reached. For example, in some embodiments, plungers for varying reservoirs for different medicaments can have different resistance (e.g. frictional and/or due to resistance offered by other reservoir and/or connector components that correspond to that specific reservoir and medicament) to movement by the drive nut. Based on the level of resistance, through the amount of electrical current required to advance the plunger, the type of medicament can be detected. For illustration, in some embodiments, the drive nut is advanced until it detects the plunger. Once the plunger is detected, the drive nut can either be retracted and/or advanced short distances (e.g., tapping of the plunger) until a sufficient force and/or current is generated and/or applied to move the plunger or its pushing against the plunger can be gradually increased (i.e. driving current escalated, without first retracting the plunger) until a sufficient force and/or current is generated and/or applied to move the plunger. Based on the force (in turn the corresponding required electrical current draw) required to move the plunger, the type of medicament in the pump receptacle can be detected. As an exemplary demonstration, four different medicaments can be provided in four different reservoirs with plungers that move in response to four different levels of force applied to the plungers (and/or current applied to the drive nut). The first medicament reservoir plunger can move in response to a lowest applied force and/or current, the second medicament reservoir plunger can move in response to a second slightly higher applied force and/or current, the third medicament reservoir plunger can move in response to a third slightly higher applied force and/or current, and the fourth medicament reservoir plunger can move in response to a fourth and highest applied force and/or current. If the third medicament reservoir is placed in the pump, the drive nut can probe the amount of force and/or current required to move the plunger with tapping (e.g., successive advancement and retraction of the drive nut) or by gradual escalation of the force and/or current as the drive nut remains in contact with the plunger (without retraction). The first, second, and fourth medicaments can be eliminated as potential medicaments in the pump by virtue of the plunger moving in response to a force/current corresponding to that required to move the plunger of the third medicament reservoir. In other words, the controller and drive nut can be configured to tap/push with the lowest force, escalate to a different force/current, and move to the next force/current until the proper amount of applied force/current is determined.

In other embodiments, one or more of the medicament reservoir detection methods described elsewhere herein can be used in combination with the detection sequences and/or probing sequences described here to determine the type of medicament in the reservoir receptacle of the pump (e.g., an optical code reader, RFID, etc.). In other embodiments, one or more of the medicament reservoir differentiation methods described elsewhere herein (e.g., an optical code reader, RFID, etc.) can be used in combination with the detection method described here to determine the type of medicament in the reservoir receptacle of the pump.

In some embodiments, in addition to or instead of one or more features of the plunger inserts described elsewhere herein, a plunger insert may also include features that give them identifiable electrical impedances (or electronic properties). In some embodiments, an insert's electrical impedance (controlled by the amount of conducting material placed into the insert, for example, during the manufacturing process) can be set and used as a unique identifier of the specific drug and/or of a specific drug property of a specific drug contained in a cartridge that includes that plunger insert. For example, in some embodiments, a variety of plunger inserts could be fabricated with different impedance levels and each impedance level could be matched with a different drug or drug property (or set of properties) of the same drug (e.g. at a different concentration, pH, excipient content, or other properties, etc.). To illustrate, a first drug could be provided in a first cartridge having a plunger with a first electrical impedance. A second drug, alternatively could be provided in a second cartridge having a second plunger with a second electrical impedance (the second electrical impedance being different from the first). Additionally, a third medicament cartridge could be provided containing the second drug at a different concentration than in the second cartridge. The third cartridge would have a third electrical impedance that is different from the first and second impedances, making each cartridge distinguishable from the next. In some embodiments, for a given voltage applied to the insert, a unique electrical current would arise for a particular plunger insert's impedance. A particular electrical current can then be linked to a specific drug and/or specific drug property (or set of properties) contained in the cartridge. These particular impedances could be mixed and matched with other features disclosed herein to give various different receptacles that avoid cross-channeling.

In some embodiments, where electrical impedance is used as an identifier for a particular drug or drug property, the matching keyset that associates each plunger insert's resultant electrical current with its corresponding drug could then be loaded into the infusion pump's software, such that the infusion pump is able to automatically identify the specific drug that is resident in the cartridge once it is loaded into the infusion pump. In some embodiments, with this method, the pump can autonomously distinguish among the drugs and/or their properties and/or could self-initialize its dosing settings accordingly, without requiring or being vulnerable to user input. Independently from this electrical impedance feature, the various plunger inserts could additionally or alternatively have different distinguishing features (as described elsewhere herein) so that each uniquely mates with matching features in the cavity of its corresponding plunger, so as to match different inserts that have different impedance levels with different plungers.

In some embodiments, a magnetic insert can be installed in the plunger. In some embodiments, the polarities of the magnetic insert and the magnet in the drive nut can be oriented to attract one another (e.g., north and south) or to repel one another (e.g., so their polarities are repulsive; e.g., south/south or north/north). In some embodiments, the magnetic insert of a medicament vial is oriented to only attract and couple to the magnet of a drive nut in the correct medicament pump aperture. Alternatively, when inserted into the incorrect medicament pump chamber, the magnetic insert repels the magnet of the drive nut. Thus, the incorrect medicament vial cannot be placed in the wrong chamber. Additionally, the electric circuit (where present) cannot be completed, thereby preventing infusion of the medicament. In some embodiments, these configurations prevent medicament misplacement and prevent infusion of the incorrect medicament.

In some embodiments, where two medicaments are to be provided using the infusion system, mischanneling can be avoided by orienting the magnetic inserts to repel incorrect medicament reservoirs and to attract only the correct medicament reservoirs. For example, a magnetic insert of the first medicament reservoir can be oriented such that it repels a magnetic tip of the drive nut in the second medicament pump cartridge aperture (e.g., chamber). Additionally, in some embodiments, a magnetic insert of the second medicament reservoir can be oriented such that it repels a magnetic tip of the drive nut in the first medicament pump cartridge aperture (e.g., chamber). In some embodiments, by avoiding insertion into the wrong chamber of the pump, the patient reduces the risk of infusing the incorrect medicament In some embodiments, as described elsewhere herein, during fabrication of a magnetic insert 565, a curable material (e.g. uncured plastic, rubber, elastomer, polymer, epoxy, composite, etc.) is mixed with magnetic filings. During mixing, the magnetic filings can be magnetically aligned using an external magnetic dipole so that a magnetic pole is formed in the curable material. In some embodiments, the curable material can then be cured to provide a magnetic insert 565 having a magnetic north and a south pole distributed within the cured material. In some embodiments, this cured insert repels the magnetic drive nut in the incorrect pump chamber and attracts the drive nut in the correct pump chamber.

In some embodiments, the magnetic insert can be configured (e.g., shaped, etc.) to only interact with an appropriate, pre-selected cartridge plunger (e.g., having coinciding, pairing features). For example, when two cartridges (A and B) are both filled at a point of care, the magnets of the magnetic insert for A and the magnetic insert for B can be configured to only insert into a plunger cartridge for medicament A and a plunger cartridge for medicament B, respectively. In some embodiments, the plunger of cartridge A and the plunger of cartridge B can have one or more differentiating features that prevent engaging the incorrect magnet insert. For illustration, magnetic insert A can have features (e.g., threads, clips, clamps, etc.) that coincide to mating features on plunger A and not plunger B. Magnetic insert B can have features (e.g., threads, clips, clamps, etc.) that coincide to mating features on plunger B and not plunger A. In some embodiments, one pair (the plunger and insert) can be threaded in the forward direction and the other pair in the reverse direction. In some embodiments, these differentiated magnetic inserts ensure that magnets are inserted correctly to attract a correct magnetic tip of a drive nut (in a correct pump chamber) and to repel an incorrect magnetic tip of a drive nut (in an incorrect pump chamber).

In some embodiments, as another measure to prevent inadvertent separation or lift-off of the elastomeric plunger 550 from the drive nut 2700 (as an additional or alternative measure), a check valve 2800 can be added to the fluid path within the cartridge or downstream of the cartridge. In some embodiments, the check valve 2800 allows fluid flow passed the check valve 2800 only if a sufficiently high pressure gradient were to exist (e.g., pressure supplied by the pump turning the lead screw and urging the plunger forward). In some embodiments, as shown in FIGS. 6Q-6T, the check valve 2800 comprises a membrane 2801 (e.g., a septum, a diaphragm, etc.) that deforms under pressure to allow fluid passed it. In some embodiments, other check valve types can be used (e.g., ball check valves, swing check valves, tilting check valves, clapper valves, stop-check valves, lift-check valves, duckbill valves, etc.).

In some embodiments, the membrane 2801 is flexible. In some embodiments, the membrane 2801 is also resilient. In some embodiments, the membrane 2801 is rubber, plastic, polymeric, elastomeric, combinations thereof, or the like. In some embodiments, when the plunger is not urged forward, the membrane 2801 rebounds to its original shape and prevents fluid from traveling through the needle 316 and into the tubing 301.

Figure 6T:
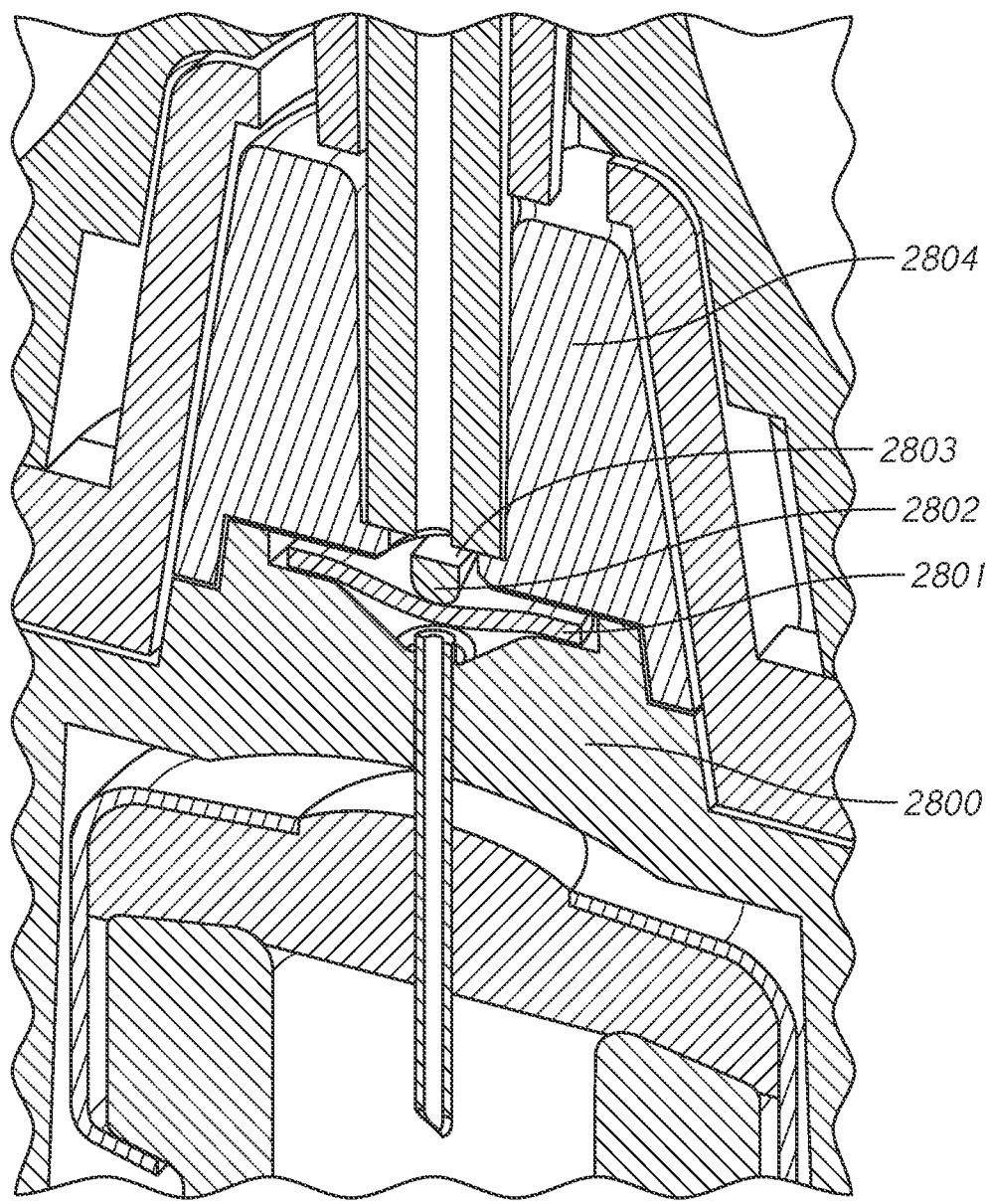

In some embodiments, the check valve comprises an opener feature 2802 against which the diaphragm 2801 presses when pressure mounts on the diaphragm 2801 from fluid being urged from the reservoir 530. In some embodiments, when the pressure is sufficient, the diaphragm 2801 deforms against the opener feature 2802 (e.g., a peg, spike, conical member, triangular member, etc.) to allow fluid (e.g., a medicament) to pass the diaphragm and escape via the tubing 301. In some embodiments, as shown in FIG. 6T, the opener feature 2802 is part of the pairing projection 2804 of the inlet connector. In some embodiments, the opening feature 2802 is connected to the pairing projection 2804 via a stem 2803 (e.g., an arm, etc.). In some embodiments, the inlet connector, opening feature, and stem are one continuous piece (e.g., injection molded together). In some embodiments, one or more of the inlet connector, opening feature, and stem can be different pieces that are connected or bonded together after fabrication of the individual parts.

In some embodiments, the check valve allows fluid to pass only after reaching a threshold pressure (e.g., a crack pressure). In some embodiments, the threshold pressure needed to allow fluid flow passed the check valve is greater than any gravitationally induced hydrostatic pressure differential that might develop between the patient and the infusion system. For instance, hydrostatic pressure can develop when the infusion system is connected to a patient via the infusion base and the patient (or user) lifts the loaded pump (containing one or more medicament vial(s)) to an elevation over the infusion base. By force of gravity, the elevation of the vial pushes fluid from the vial through the conduit and into the patient via the infusion base set. The amount of hydrostatic force applied is determined by the elevation of the medicament vial over the infusion set. The amount of hydrostatic force, therefore, is usually limited by the length of the fluid conduit (which ultimately connects the medicament vial to the infusion set). In some embodiments, a standard length of the fluid conduit is about 110 cm or about 60 cm. In some embodiments, the check valve is sufficiently resilient to remain closed when a vial of medicament in the infusion system is elevated over the infusion set by a distance of at least: about 220 cm, about 110 cm, about 60 cm, values between the aforementioned values, or ranges spanning those values. In some embodiments, the check valve is designed such that the threshold pressure gradient needed to allow fluid flow passed the check valve is greater than any hydrostatic pressure differential that might arise due to any other changes in the hydrostatic pressure between the patient and the infusion system (e.g., force caused by an airplane changing elevation, a carnival ride, bungee jumping, physical activity, etc.).

Figure 6U:
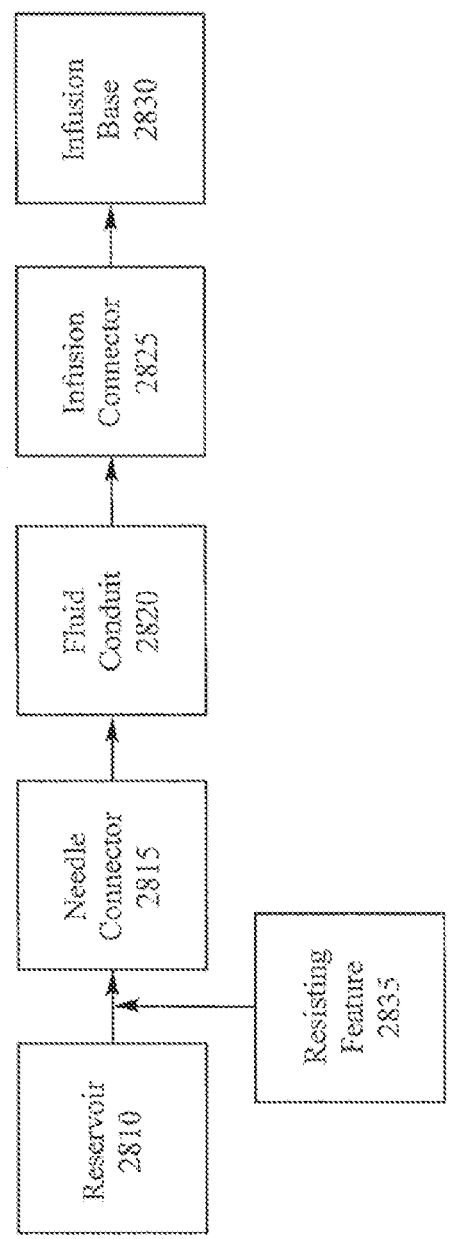
Figure 6V:
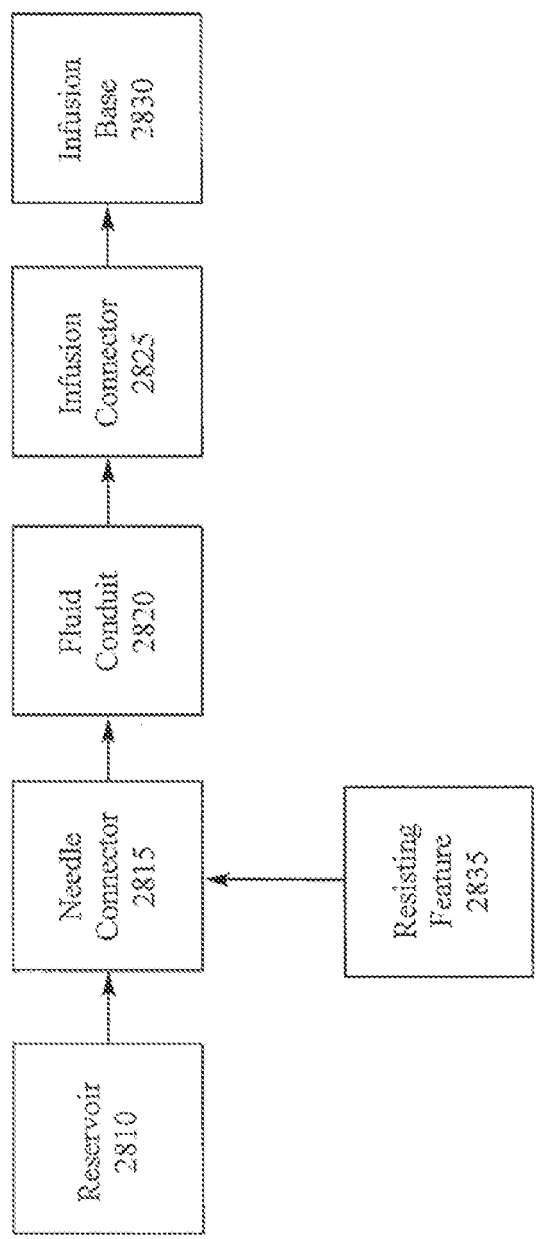
Figure 6W:
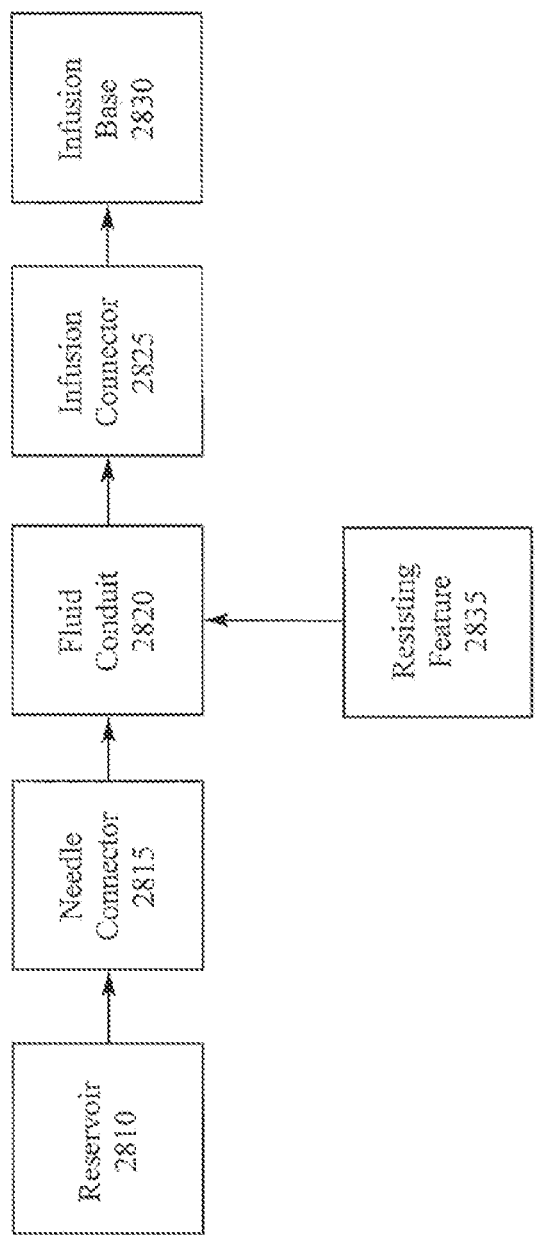
Figure 6X:
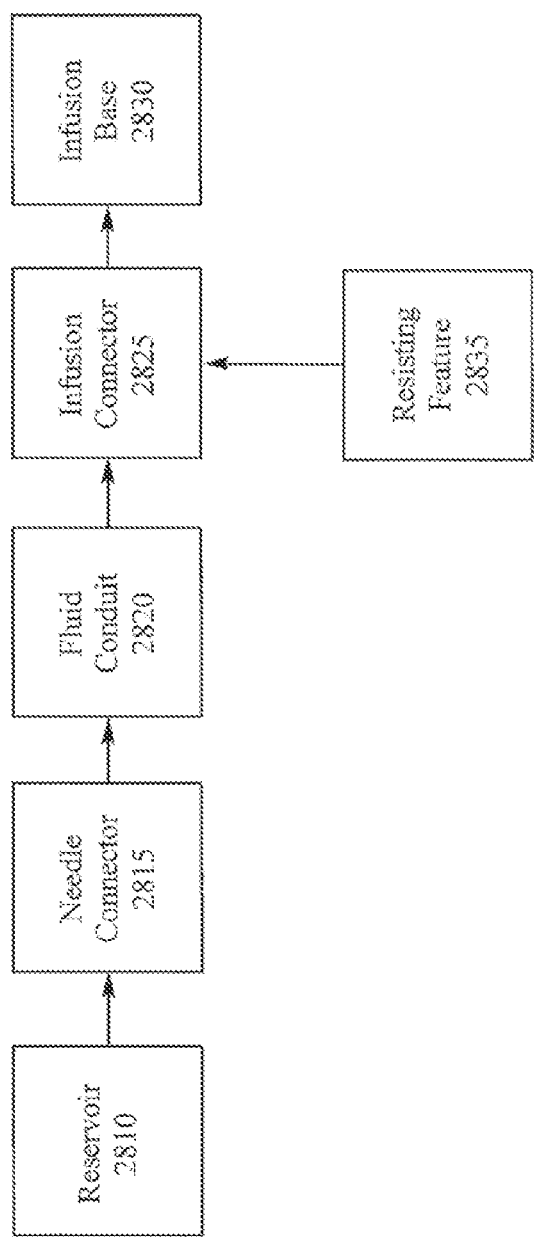
Figure 6Y:
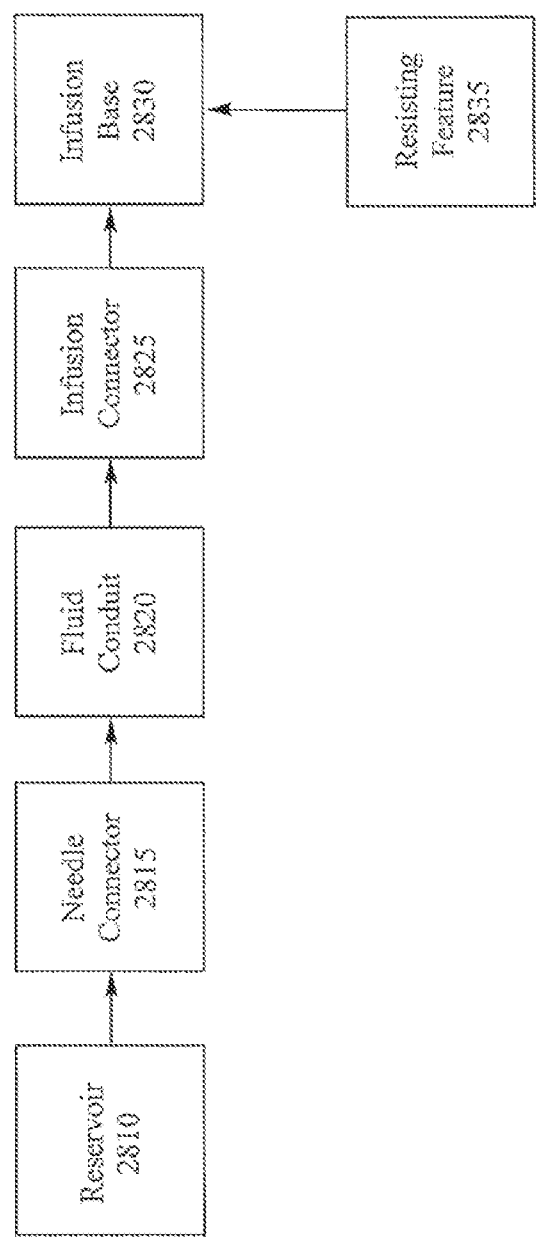

In some embodiments, as shown in FIGS. 6Q-6T, the check valve is integrated into the needle connector (e.g., inlet connector) that couple to and capture the cartridges containing the medicaments. Alternatively, the check valve could be integrated anywhere along the length of the tubing 301, into the infusion site base, the infusion site connectors, or elsewhere in the infusion system. For instance, as shown in FIG. 6U, the resisting feature 2835 (e.g., the check valve or a similar back flow stopper), can be positioned between the reservoir 2810 and the needle connector 2815 (e.g., in the needle). As shown in FIG. 6V, the resisting feature 2835 can be located in the needle connector 2815. As shown in FIG. 6W, the resisting feature 2835 can be located in the along the fluid conduit 2820. As shown in FIG. 6X, the resisting feature 2835 can be located in the infusion connector 2825. As shown in FIG. 6Y, the resisting feature 2835 can be located in the infusion base 2835. As shown in FIG. 6Z, the resisting feature 2835 can be located anywhere in the infusion system between the patient 2840 and the reservoir 2810.

In some embodiments, a transient connection between the plunger and drive nut is provided. In some embodiments, the connection between the plunger and drive nut does not require and/or does not comprise a magnet and/or a ferrous insert. In some embodiments, the connection between the plunger and drive nut uses one or more features on the tip of the drive nut that connects to (e.g., couples with, fits inside, envelopes, engages, fixes to, etc.) the plunger and/or retains the plunger. In some embodiments, the connection between the plunger and drive nut is a physical connection (e.g, accomplished with threading, a snug-fit connection, a snap-fit connection, and/or a barbed connection) and is not magnetic.

In some embodiments, an optical sensor detects the presence of a medicament reservoir. In some embodiments, the optical sensor detects, for example, the proximity of the plunger to the drive nut. In some embodiments, the optical sensor detects a feature of the plunger (e.g., shape, color, etc. of the insert or plunger). In some embodiments, the optical sensor is in electronic communication with a software module that determines when/if there is contact with the plunger and/or that the correct plunger is being used (e.g., the correct plunger within the reservoir). In some embodiments, once receiving input from the optical sensor and determining if the proper reservoir is inserted, the pump activates (when the proper medicament is inserted) or deactivates (when the improper medicament is inserted). In some embodiments, as disclosed elsewhere herein, once an improper medicament is detected, the pump can automatically reconfigure to provide the correct dosing regimen of the inserted medication. In some embodiments, once an improper medicament is detected, the pump or a display on the pump can indicate to the user that the improper medicament has been placed in the pump. In some embodiments, the user can manually reconfigure the pump to provide the correct dosing regimen of the inserted medication.

In some embodiments, the drive nut comprises a mechanical switch (e.g., on the tip of the drive nut) that can be activated (e.g., depressed, displaced, moved, etc.) when it contacts a plunger. In some embodiments, the mechanical switch is configured to only be activated by appropriate medicament reservoirs (e.g., because incorrect reservoirs are not shaped appropriately to depress the switch). For example, in some embodiments, switch is located at the center of the drive nut and a non-matching (e.g., incorrect) medicament reservoir comprises a hood or sash that elevates the plunger of the medicament reservoir over the switch such that the switch is not depressed as the drive nut contacts the reservoir. In some embodiments, the switch can be located on the plunger and can be activated by the drive nut. In some embodiments, the pump (e.g., an optical sensor in the pump, receiver, etc.) is configured to detect when the switch of the plunger is actuated.

In some embodiments, the drive nut comprises a capacitive proximity sensor. In some embodiments, the capacitive proximity sensor is positioned on the tip of the drive nut. In some embodiments, the capacitive proximity sensor detects when the plunger is in proximity with and/or is contacted by the drive nut. In some embodiments, the capacitive proximity sensor indicates and/or detects when the drive nut and plunger are in close proximity and/or are substantially in contact with each other. In some embodiments, the capacitive proximity sensor detects when the plunger and the drive nut are separated by a distance of less than or equal to about: 2 mm, 1 mm, 0.5 mm, 0.1 mm, or ranges including and/or spanning the aforementioned values. In some embodiments, when a cartridge is inserted and the proximity sensor does not detect the plunger (e.g., because one or more features on the cartridge, the plunger, and/or drive nut prevent the proximity sensor from coming into close enough proximity to the plunger to detect it), an indication is provided to the user (e.g., an alarm that is audible, visual, haptic, vibrational, etc.). In some embodiments, when a cartridge is inserted and the proximity sensor does not detect the plunger (e.g., because one or more features on the cartridge, the plunger, and/or drive nut prevent the proximity sensor from coming into close enough proximity to the plunger to detect it), the pump automatically retracts the drive nut away from the cartridge. In some embodiments, once the drive nut is retracted, the pump will not allow the drive nut to traverse forward until a new cartridge is placed in the pump chamber. In some embodiments, when the proximity sensor detects the plunger, an indication is provided to the user (e.g., an alarm that is audible, visual, haptic, vibrational, etc.).

In some embodiments, the reservoir or connector set comprises a microfluidic valve, an electronically activated valve, a solenoid valve, a hydro-mechanical operated valve, and/or pneumatic valve. In some embodiments, the microfluidic valve (or other valve) is actuated by the pump and allows flow when the drive motor is active. In some embodiments, the microfluidic valve (or other valve) is closed when the drive motor is inactive. In some embodiments, the active closing and opening of the actuating valve prevents inadvertent dosing when the drive motor is not active.

In another embodiment, redundant mechanisms could be put in place to prevent inadvertent separation or lift-off of the elastomeric plunger from the drive nut. In such an embodiment, the elastomeric plunger insert could be made of an electrically conductive material having magnetic properties (such as an electrically conductive plastic loaded with ferrous material), and a check valve could be integrated into the needle connector. Coupled with a magnet located at the tip 2702 of the drive nut 2700 in each pump chamber, and a passive electrical circuit installed on top of that magnet, which would be powered remotely via RFID from an active circuit installed somewhere within the pump housing, these systems could simultaneously serve to prevent inadvertent separation or lift-off of the elastomeric plunger from the drive nut, to capture the elastomeric plunger by the drive nut, and to detect (and continuously monitor) that the elastomeric plunger has been captured by the drive nut.

In some embodiments that utilize a needle transfer hub to transfer medicament from a vial to the cartridge, the body of the needle transfer hub could be manufactured from the same mold as the needle connector, except without the capture-and-locking feature as the needle transfer hub would need to be removed from the cartridge upon completing the filling procedure, whereas the needle connector would permanently capture the cartridge and would be disposed of along with the cartridge once the cartridge was emptied of its deliverable contents.

In some embodiments involving a single medicament or multiple medicaments, the inlet end of each tubing is overmolded, bonded, press-fitted, glued, solvent bonded, insert molded, or otherwise attached to a needle connector (e.g., the inlet connector) and the outlet end of each tubing is overmolded, bonded, press-fitted, glued, solvent bonded, insert molded, or otherwise attached together with an infusion site and a cannula that delivers the medicament or medicaments to the delivery area (e.g., delivery transdermally, intradermally, subcutaneously, intramuscularly, intravenously, etc.).

In some embodiments involving a single medicament or multiple medicaments, the inlet end of each tubing is overmolded, bonded, press-fitted, glued, solvent bonded, insert molded, or otherwise attached to a needle connector (as in FIGS. 1A-4B) and the outlet end of each tubing is overmolded, bonded, press-fitted, glued, solvent bonded, insert molded, or otherwise attached to a straight, beveled, hollow, stainless steel needle and a component designed to connect to a subcutaneous or intradermal infusion site base (as in the dual-medicament infusion site connectors in FIGS. 8, 9, and 13, and the single-medicament infusion site connectors in FIGS. 11 and 12). For each medicament, this arrangement creates a closed, independent, patent, and continuous fluid path from the medicament reservoir to the end of the straight, beveled, hollow, stainless steel needle in the site connector. In some embodiments, each site connector can be physically independent and can connect to or disconnect from an infusion site base repeatedly.

FIGS. 7A-B are isometric views showing a portion of a dual-medicament infusion set. FIG. 7A shows an embodiment of a dual-medicament site base inserter 2426 attached. In FIG. 7B the dual-medicament site base inserter 2426 has been removed. In some embodiments involving two medicaments, the dual-medicament site base inserter 2426 couples two disjoint halves: the right site base 2424 (e.g., the first base, the glucagon base, etc.), and the left site base 2525 (e.g., the second base, the insulin base, etc.). In some embodiments, the inserter 2426 provides a handle for the application of the dual-medicament infusion site base 2401. In some embodiments, the base 2401 includes one or more needle guards 2429, 2529. In some embodiments, the infusion set base 2401 comprises one or more release liners 2428, 2528. In some embodiments, the infusion set base 2401 comprises an adhesive 2427, 2527 (e.g., a tape, gel, rubber adhesive, etc.). In some embodiments, once the two needle guards 2429, 2529 and the two release liners 2428, 2528 have been removed and discarded, the dual-medicament site base inserter 2426, can be used to apply the dual-medicament infusion set base 2401. In some embodiments, the adhesive tape 2427, 2527 can be used to adhere the dual-medicament infusion set 2401 to the surface of the skin. In some embodiments, after insertion, the dual-medicament site base inserter 2426 is disposable and is removed by activating the two living hinges 2436, 2536 and sliding the dual-medicament site base inserter 2426 out of the retention slots 2430, 2530 (shown in FIG. 9B) to reveal the two posts 2431, 2531 that are now ready to accept site connectors (see FIGS. 8A-B). In some embodiments, as shown in FIG. 7B, the posts 2431, 2531 are asymmetric. In some embodiments, the infusion set inserter 2426 is reusable and can be reattached to the site bases 2424, 2525.

In some embodiments, the infusion set includes a connector cover 2434. FIG. 8A is an isometric view showing the dual-medicament infusion site connectors 2432, 2533 with a dual-medicament site connector cover 2434 attached.

FIG. 8B shows the dual-medicament infusion site connectors after the dual-medicament site connector cover 2434 has been removed. In some embodiments, the dual-medicament site connector cover 2434 couples the two disjoint halves: the first site connector 2432, and the second site connector 2533. In some embodiments, the site connector cover 2434 protects the site connectors 2432, 2533 from exposure (e.g., to dust, dirt, abrasion, physical damage, etc.) when they are not connected to the dual-medicament infusion site base 2401 (shown in FIG. 7A). In some embodiments, the second site connector 2533 can be disconnected from the dual-medicament site connector cover 2434 by activating the living hinge 2536 to release the retention clip 2535 and then sliding the second site connector 2533 out of the retention slot 2530 (shown in FIG. 9B). Disconnection of the second site connector 2533 from the dual-medicament site connector cover 2434 reveals the alignment posts 2539 and the asymmetric post receptacle 2538 which mate with corresponding features on the left site base 2525 (shown in FIG. 7B). The same procedure can be used to disconnect the first site connector 2432 from the dual-medicament site connector cover 2434, using corresponding features and similarly tens-place enumerated features (e.g., 2436 corresponds to 2536). The order of disconnection from the dual-medicament site connector cover 2434 and reconnection to the dual-medicament infusion site set base 2401 is arbitrary.

In some embodiments (as shown in FIG. 6G, the infusion site connector 2632 comprises an ergonomic feature (e.g., a flared-out edge, a finger hold, a bulbous end, etc.). In some embodiments, the ergonomic feature allows the infusion site connector to be easily grasped and pulled from the infusion base. In some embodiments, as shown in FIG. 6F, the infusion site connector 2632 can have a thin section and a thick section, with the thick section being located proximal (towards) the tubing 301, and the thin section being proximal to base connection point. In some embodiments, this design feature, similar to the ergonomic feature, allows the infusion site connector to be easily grasped by the finger tips and slid away from the infusion base.

Figure 9B:
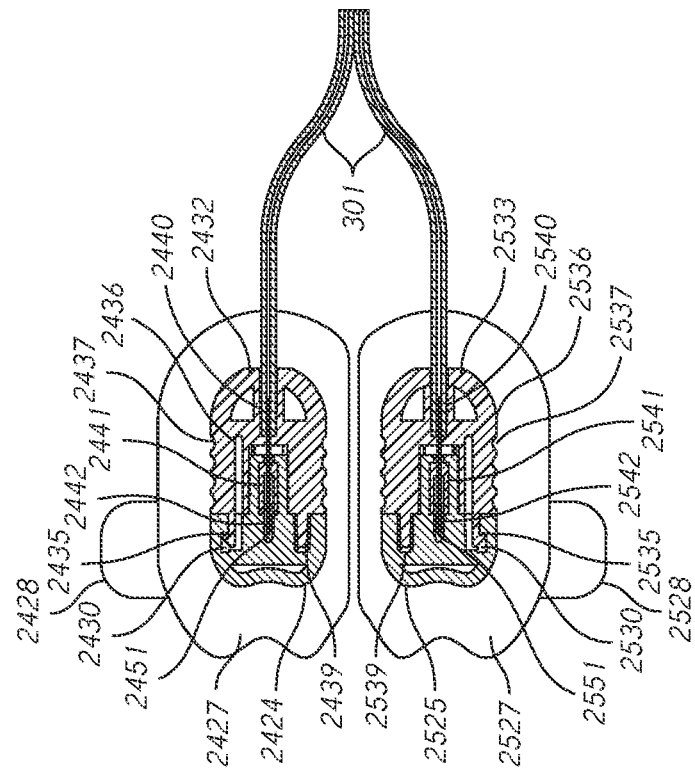
FIGS. 9A-9B illustrate views of a dual medicament infusion set where 9B is a cross-sectional view from the top.
Figure 9A:
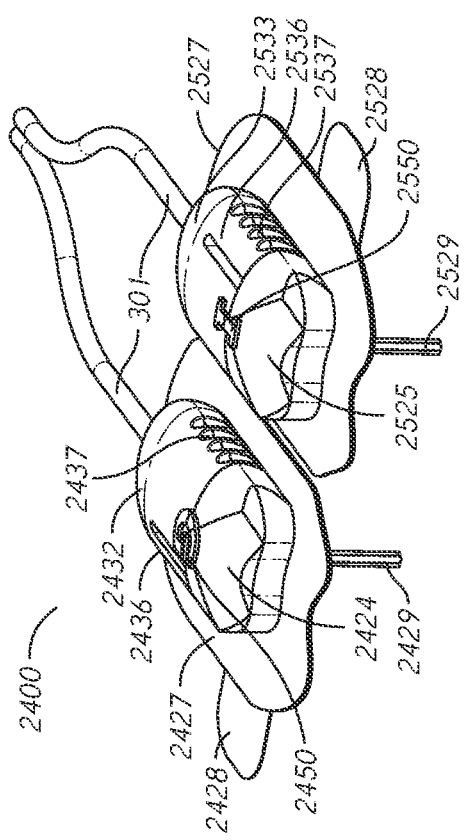

FIG. 9A shows an isometric view of the complete dual-medicament infusion set 2400 including the dual-medicament infusion site base 2401 assembled with the dual-medicament infusion site connectors. In some embodiments, as shown, the infusion set comprises a first infusion assembly comprising a first base and a first connector and a second infusion assembly comprising a second base and a second connector. In some embodiments, having the bases separate prevents needle pull in a system where both needles are fixed to a single base. In some embodiments, this feature increases comfort when the infusion set is placed on an area where movement, pulling, and discomfort can occur. FIG. 9B shows a cross-sectional view revealing the internal components of the dual-medicament infusion set 2400. In some embodiments, after connection of the first site connector 2432 and the second site connector 2533, to the first site base 2424 and the left site base 2525, respectively, two closed, independent, patent, and continuous fluid paths are created. In some embodiments, the fluid paths terminate at 90 degree, beveled, hollow, piercing members 2442, 2542 (stainless steel needles). In some embodiments, each fluid path can begin in many types of connections to a fluid reservoir such as luer locks or custom cartridge connectors that eventually communicate with the lumen of the tubing 301 which is bonded together with a straight, beveled, hollow, stainless steel needle 2440, 2540 and an infusion site connector 2432, 2533, respectively. In some embodiments, upon connecting an infusion site connector(s) to an infusion site base(s), the straight, beveled, hollow, stainless steel needle 2440, 2540 pierces a site base septum 2441, 2541 respectively, allowing fluid to be pushed through the 90 degree, beveled, hollow, stainless steel needle 2442, 2542 for delivery to the patient. In some embodiments, lettering (or other visual indicators) 2450, 2550 are present on the infusion set 2400. In some embodiments, for example as shown in FIG. 9A, the indicators 2442, 2542 provide convenience to a user, though, in some embodiments, mis-connection of components is still mechanically prevented. In some embodiments, the 90 degree, beveled, hollow, stainless steel needle 2442, 2542 is placed using a sub-assembly consisting of itself, a soft durometer tube 2451, 2551 and the site base septum 2441, 2541 which is then secured with a plug (not shown).

FIG. 10A is an isometric view showing the first site base 2424 (shown in FIG. 7B), as it would be used in the single-medicament configuration. In some embodiments, a first site base inserter 2443 can be attached as shown. FIG. 10B shows the first base 2424 after the first site base inserter 2443 has been removed. In some embodiments, the first site base inserter 2443 provides a handle for the application of the single-medicament infusion site base 2424. In some embodiments, after insertion, the first site base inserter 2443 is removed by activating the living hinge 2436 and sliding the right site base inserter 2443 out of the retention slot, 2430, to reveal the asymmetric post, 2431 that is now ready to accept a site connector 2432. Although only the first half of the dual-medicament infusion site base 2401 (shown in FIG. 7B) is shown, the second half 2433 could also be used in a single-medicament configuration. In some embodiments, the second half 2433 could be attached using the same strategy as for the first half 2432, but with components having uniquely pairing features, hinges, etc.

FIG. 11A shows an isometric view of the first site connector 2432 (shown in FIG. 8), as it would be used in the single-medicament configuration, with the first site connector cover 2446. FIG. 11B shows the first site connector 2432 after the first site connector cover 2446 has been removed. In some embodiments, the first site connector cover 2446 protects the first site connector 2432 from exposure (e.g., to dirt, grime, debris, physical damage from bumps, etc.) and can be removed by activating the living hinge 2436, to release the retention clip 2435 and then sliding the first site connector 2432 out of the retention slot 2430 (shown in FIG. 12B). In some embodiments, disconnection of the first site connector 2432 from the first site connector cover 2446 reveals the alignment post 2439 and the asymmetric post receptacle 2438, which mate with corresponding features on the first site base 2424 (shown in FIG. 10). Although this depiction describes only the first half of the dual-medicament infusion site connectors (shown in FIG. 8), the second half could also be used in a single-medicament configuration with similarly numbered features.

FIG. 12A shows an isometric view of the complete single-medicament infusion set 2400' including the single-medicament infusion site base 2424 assembled with the single-medicament infusion site connector 2432. FIG. 12B shows a cross-sectional view revealing the internal components of the single-medicament infusion set 2400'. In some embodiments, after connection of the first site connector 2432 to the first site base 2424, a closed, independent, patent, and continuous fluid path is created. In some embodiments, the closed fluid path terminates in a 90 degree piercing member, 2442 (e.g., a beveled, hollow, stainless steel needle). In some embodiments, the fluid path can begin in many types of connections to a fluid reservoir such as luer locks or custom cartridge connectors that eventually communicate with the lumen of the tubing 301. In some embodiments, the tubing 301 is bonded together with a straight piercing element 2440 (e.g., a beveled, hollow, stainless steel needle) and, in this depiction, the first site connector 2432. In some embodiments, upon connecting the first site connector 2432 to the right site base 2424, the straight, beveled, hollow, stainless steel needle 2440 pierces the site base septum 2441, allowing fluid to be pushed through the 90 degree, beveled, hollow, stainless steel needle 2442, for delivery to the patient. In some embodiments, although this depiction is analogous only to the first half of the dual-medicament infusion set (shown in FIGS. 9A-B), the second half of the infusion set (e.g., the left half) could also be used in a single-medicament configuration. In some embodiments, lettering or other visual indicators 2450, 2550 are present and provide convenience to a user. In some embodiments, beside the visual indicators, mis-connection of components is still mechanically prevented. In some embodiments, the 90 degree, beveled, hollow, stainless steel needle 2442 is placed using a sub-assembly consisting of itself, a soft durometer tube 2451 and the site base septum 2441 which is then secured with a plug (not shown).

Figure 13E:
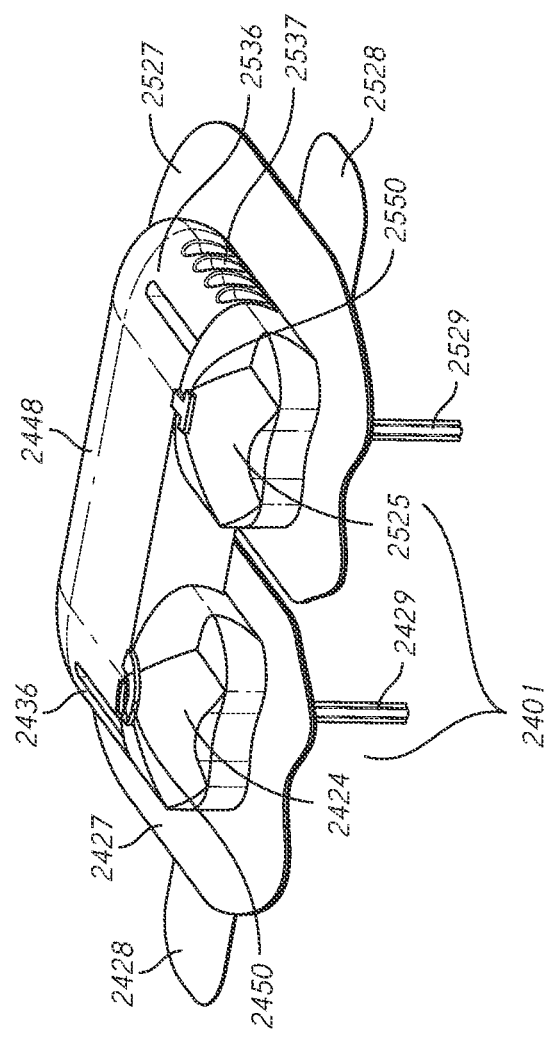

FIGS. 13A-E show isometric views of embodiments of a dual-medicament infusion set. FIG. 13A with the right site base 2424, connected to a right site base cover 2444. FIG. 13B shows the second site base 2525 connected to a second site base cover 2545. FIG. 13C shows the first site connector 2432 connected to a first site connector cover 2446. FIG. 13D shows the second (left) site connector 2533 connected to a second (left) site connector cover 2547. FIG. 13E shows the dual-medicament infusion site base 2401 connected to a dual-medicament site base cover 2448. In some embodiments, when an individual site connector must be replaced, it can be disconnected from its site base and a site base cover can be temporarily connected to the site base thereby protecting it from exposure (as in A and B) until the site connector can be replaced. In some embodiments, if both site connectors are removed together, a dual-medicament site base cover 2448 can be connected temporarily to both site bases to protect them from exposure until the site connectors can be replaced (as in E). In some embodiments, when any individual site base must be replaced, it can be disconnected from its site connector and a site connector cover is temporarily connected to the site connector thereby protecting it from exposure (as in C and D) until the site base can be replaced. In some embodiments, if both site bases are removed together, a dual-medicament site connector cover can be connected temporarily to both site connectors to protect them from exposure until the site bases can be replaced (as in FIG. 8A). A single-medicament embodiment could operate in the same manner as the right site half of A and C or the left site half of B and D.

In some embodiments, a single-medicament implementation of the infusion system that infuses only medicament A can use one of the two single-medicament infusion site connectors of the dual-medicament infusion site connectors. Similarly, the other single-medicament infusion site connector, which is distinct from the single-medicament infusion site connector for medicament A, can be used for a single-medicament implementation of the infusion system that infuses only medicament B. In some embodiments, asymmetric features in the dual-medicament infusion site connectors, such as any combination of asymmetric posts, asymmetric post receptacles, retention clips, alignment posts, and/or keys and keyways can be used to differentiate the single-medicament infusion site connector for medicament A from medicament B. In some embodiments, such features can also be used to ensure that a single-medicament implementation of the infusion system that infuses only medicament A uses only the medicament A chamber in the pump housing, and a single-medicament implementation of the infusion system that infuses only medicament B uses only the medicament B chamber in the pump housing. In some embodiments, in this way, the same molds used to manufacture the dual-medicament infusion site connectors will serve for the single-medicament infusion site connectors for a single-medicament implementation of the infusion system that infuses only medicament A or only medicament B. Thus, the constituent components of the dual-medicament infusion site base, dual-medicament infusion site connectors, tubing, and needle connectors, which serve a dual-medicament implementation of the infusion system, can be used to serve one of two distinct single-medicament implementations of the infusion system, one for medicament A and one for medicament B.

In some embodiments, software (either integrated into the infusion system or run on an auxiliary device such as a smart-phone or tablet) can be used to configure (automatically and/or manually) the infusion system to be configured either as a dual-medicament infusion system, as a single-medicament infusion system that uses only the medicament A chamber in the pump housing, or a single-medicament infusion system that uses only the medicament B chamber in the pump housing. In some embodiments, once any of these three configurations is implemented, the dual-medicament infusion site connectors or appropriate single-medicament infusion site connectors (either pertaining to medicament A or medicament B) can be chosen to match the particular configuration.

In some embodiments involving a site connector or site connectors, each site connector can be designed to connect to a site base by the action of at least one retention clip. Connection of a site connector to a site base allows a straight, beveled, hollow, stainless steel needle to pierce a septum in the site base (as in FIGS. 9 and 12). In some embodiments, once the straight, beveled, hollow, stainless steel needle in a site connector pierces the site base septum in a site base, it is brought into fluid continuity with a 90 degree, beveled, hollow, stainless steel needle, which can deliver the medicament to the delivery space. In some embodiments, this arrangement creates, for each medicament, a closed, independent, patent, and continuous fluid path from the medicament reservoir to the patient (e.g., for delivery transdermally, intradermally, subcutaneously, intramuscularly, intravenously, etc.). In some embodiments, each site base can be physically independent and can connect to or disconnect from a site connector repeatedly.

In some embodiments involving the use of a site base, the 90 degree, beveled, hollow, stainless steel needle can be overmolded, bonded, press-fitted, glued, solvent bonded, insert molded, or otherwise attached to the site base. In some embodiments, as an example other than insert molding, such a 90-degree, beveled, hollow, stainless steel needle may be sheathed with a soft durometer tube, which is in turn press-fit into the site base septum to create a sub-assembly outside the site base. In some embodiments, this sub-assembly can then be placed into a cavity in the site base (as shown in FIGS. 9 and 12) and a plug (not shown) can be used to hold the sub-assembly firmly in place while simultaneously ensuring a fluid seal.

In some embodiments involving the use of a site base, the 90 degree, beveled, hollow, stainless steel needle, the needle may be designed to protrude from the center or near the center of the site base. In some embodiments, this arrangement increases the likelihood that the site base will remain adhered to the surface of the skin for the entirety of its intended use.

In some embodiments involving multiple medicaments where a site connector can be connected to or disconnected from a site base, the site connectors and site bases can contain features such as lettering or other visual indicators to help prevent mis-connection of a site base or a site connector to incorrect site connectors or site bases. In some embodiments, such lettering or other visual indicators (colors, etc.) can be used in addition to physical features that mechanically prevent mis-connection. In some embodiments, the lettering or other visual indicators can be raised and colored differently from the base material to enhance visibility.

In some embodiments involving multiple medicaments where a site connector can be connected to or disconnected from a site base, the site connectors and the site bases can contain features such as asymmetric post receptacles, retention clips, alignment posts, and/or keys and keyways that prevent mis-connection of a site base or a site connector to incorrect site connectors or site bases.

In some embodiments involving a site connector or site connectors, each site connector can be designed to connect to a site base by the action of at least one retention clip that fits into at least one retention slot. In some embodiments involving two medicaments where only one retention clip and retention slot pair is used on each site connector and site base pair, the retention clips and retention slots may be present on the medial or lateral (as in FIGS. 7-9) sides of the site connectors and site bases. If the retention clips and retention slots are present on the lateral side of one site connector and site base pair, and on the medial site of the other site connector and site base pair, convenience is afforded to the user by allowing for the same finger to activate the living hinges. In this case, mis-connection of the site connectors to incorrect site bases is still prevented by the presence of the asymmetric posts and asymmetric post receptacles.

In some embodiments involving two medicaments, a right site connector and a left site connector (as in FIGS. 8, 9, and 13) comprise the dual-medicament infusion site connectors, can be physically independent, and can contain features such as asymmetric post receptacles, retention clips, alignment posts, and/or keys and keyways that prevent mis-connection of the dual-medicament infusion site connectors to a dual-medicament infusion site base.

In some embodiments involving two medicaments, a right (first) site base and a left (second) site base (as in FIGS. 7, 9, and 13) comprise the dual-medicament infusion site base, can be physically independent, and can contain features such as retention slots (shown in FIG. 9), asymmetric posts, and alignment post receptacles that prevent mis-connection of the dual-medicament infusion site connectors to the dual-medicament infusion site base.

In some embodiments the site connectors and site bases are designed such that any site connector and site base pair from a multiple medicament configuration can be used individually in a single medicament configuration (as in FIGS. 10-12) such that the single medicament site connectors and site bases can be manufactured from the same tools as the multiple medicament site connectors and site bases.

In some embodiments involving multiple medicaments, the site connectors can be supplied with one or more site connector covers that may couple all of the site connectors, certain groups of the site connectors, or none of the site connectors such that each site connector can be supplied with its own site connector cover. The site connector cover can be connected to and disconnected from the site connectors repeatedly and protects them from exposure (as in FIG. 8A). Likewise, the site bases can be supplied with one or more site base covers that may couple all of the site bases, certain groups of the site bases, or none of the site bases such that each site base can be supplied with its own site base cover. The site base cover can be connected to and disconnected from the site bases repeatedly and protects them from exposure (as in FIG. 13).

In some embodiments involving a single medicament or multiple medicaments wherein each site base is supplied with its own site base cover and each site connector is supplied with its own site connector cover, the site base covers and the site connector covers could be manufactured from the same tools as the site bases and the site connectors respectively. In some embodiments, each site base cover may not contain the straight, beveled, hollow, stainless steel needle and the tubing and each site connector cover may not contain the 90 degree, beveled, hollow, stainless steel needle and the site base septum.

In some embodiments involving a single medicament or multiple medicaments, the site base or site bases can be supplied with a site base inserter that connects to the site base or site bases in the same manner as the site connectors and provides a handle for the application of site base or site bases (as in FIGS. 7 and 10). In some embodiments, the handle provided by the site base inserter may be used to apply the site base manually or to load the site base(s) into an automated insertion device, such as a spring loaded inserter. In some embodiments, in the case of multiple site bases, one or more site base inserters may couple all of the site bases, certain groups of the site bases, or none of the site bases such that each site base can be supplied with its own site base inserter. In some embodiments, removal of a site base inserter would decouple any coupled site bases.

In some embodiments, the infusion pump may be equipped with a cartridge detection hardware-software system that would detect, separately, whenever each cartridge is fully loaded and secured in its corresponding pump chamber. In some embodiments, since the design described herein can ensure that only the correct medicament cartridge can be fully loaded and secured in its corresponding pump chamber, the cartridge detection system can, when functioning in conjunction with the design described herein, effectively and conclusively inform the infusion pump system of which specific medicaments are available for potential infusion. In some embodiments, the availability status of each medicament for potential infusion at any point in time would also allow the infusion pump system to set its mode of operation accordingly. In some embodiments, for example, in the case of a dual-chamber pump, the detection of both cartridges being in place would allow the infusion pump system to operate in dual-infusion mode, whereas the detection of one cartridge being in place but not the other would lead the infusion pump system to operate in a single-infusion mode that is specific to the medicament that corresponds to the cartridge that is detected to be in place. In some embodiments, this detection capability would be determined autonomously in real time, including when a cartridge is in place or out of place transiently or temporarily.

In some embodiments, the infusion pump may also be equipped with a delivery occlusion hardware-software detection system that would detect, separately, whenever the fluid-delivery path associated with each cartridge is impeded or obstructed anywhere from the cartridge, all the way through the corresponding tubing, and out to the distal end of the corresponding site base. In some embodiments, since the design described herein can ensure that only the correct tubing assembly and site base can be connected to their corresponding cartridge, the occlusion detection system would, when functioning in conjunction with the design described herein, effectively and conclusively inform the infusion pump system of which specific medicaments have a patent fluid-delivery path.

In some embodiments, with both cartridge and occlusion detection systems simultaneously present, the infusion pump may at any point in time conclusively determines which medicament is possible to deliver to the user. In some embodiments, the infusion pump could then autonomously set its mode of operation, as per the detection of which of the cartridges are in place along with the patency of their corresponding fluid-delivery paths. In some embodiments, in a specialized example of a dual-chamber pump that autonomously controls blood glucose levels by delivering insulin or an insulin analog, as well as a counter-regulatory agent (e.g. glucagon, a glucagon analog, or dextrose), such cartridge and occlusion detection systems, when functioning in conjunction with the design described here, would practically allow the infusion pump system to be prescribed in a particular configuration to deliver only insulin, or only the counter-regulatory agent, or both. Moreover, in some embodiments, such an implementation would also allow the dual-chamber infusion pump system to autonomously switch its mode of operation in real time whenever either delivery channel becomes unavailable for delivery (whether informed by cartridge detection, occlusion detection, or both), including in cases where channel availability may alternate in real time. In some embodiments, the cartridge and occlusion detection methods could be realized through a variety of hardware and software implementations, including, but not limited to, techniques that rely on magnetic field or electrical signal feedback in the case of cartridge detection, or techniques that rely on back pressure detection or flow sensor technology in the case of occlusion detection, to mention but a few.

In some embodiments, the features described in the context of one base, connector, housing, inlet connector, inlet connector cover, collar, medicament reservoir, or pump assembly can be mixed and matched and used in different combinations on other bases, connectors, housings, inlet connectors, inlet connector covers, collars, medicament reservoirs, or pump assemblies. For instance, any feature described above to prevent mischanneling can be deleted from or added to other embodiments. Redundant features can be added or deleted from the components of the medicament delivery systems.

The examples shown here are meant to be representative of a general approach to the design of an infusion system for multiple medicaments and various connectors, tubes, and cartridges to ensure proper channeling of each medicament to the patient. The geometric shapes, sizes, orientations, locations, and number of tabs, protrusions, and features, as well as the corresponding cavities, grooves, keyways, or slots are merely meant to be examples of a much greater abundance of variations on the particular examples shown here.

For instance, as described elsewhere herein, the degrees of separation between the tabs, protrusions, and features on the cap connectors and on the corresponding cavities, grooves, keyways, or slots in the pump housing, or the degrees of separation between the tabs, protrusions, and features on the pre-fitted collar assembly and the corresponding cavities, grooves, keyways, or slots on the cap connector shown here can be generalized to be placed closer together or farther apart than in the examples shown here. Additionally, the number of tabs, protrusions, and features on the cap connectors and on the corresponding cavities, grooves, keyways, or slots in the pump housing, or the number of tabs, protrusions, and features on the pre-fitted collar assembly and the corresponding cavities, grooves, keyways, or slots on the cap connector designs shown here can be generalized to one, two, three or more such features, which might have different sizes, shapes, orientations, and locations from the examples shown here. Moreover, as discussed above, the locations of the tabs, protrusions, and features on the pre-fitted collar assembly and the corresponding cavities, grooves, keyways, or slots on the cap connector designs shown here need not be limited to the neck or head (or crown) regions of the cartridge. For instance, the point of engagement between the pre-fitted collar assembly and the cap connector could alternatively occur elsewhere on the body of the cartridge, or extend over the entire length of the cartridge. In some embodiments, the tabs, protrusions, and features on the pre-fitted collar assemblies described here could instead appear directly on the surface of the cartridge (such as in the case of an injection molded cartridge), which is either pre-filled with medicament or not pre-filled with medicament.

In some embodiments, the cartridges described here can either be pre-filled with medicament or not pre-filled with medicament before or after the pre-fitted collar assemblies described here are installed onto the cartridge. In the case of the latter, such cartridges can be filled with medicament sometime after the manufacturing process, including at the point of care.

In some embodiments, for example in the case of a cartridge that is filled with medicament at the point of care, the cap connector might not contain a recessed needle, but rather might couple with said cartridge using a standard luer lock or other mechanism, as in FIG. 50, in which the medicament flows directly from the cartridge into the tubing without first passing through a needle. In this case, the tabs, protrusions, and features on the pre-fitted collar assemblies described here would still appear on the surface of the cap connector.

In some embodiments, mischanneling of medicaments can still be avoided if one cartridge is prefilled with one medicament and a second cartridge is filled at the point of care with a different medicament (using the embodiment described in FIGS. 5A-C). So long as only one cartridge needs to be filled with medicament at the point of care, and all other cartridges are pre-filled with medicaments, the designs described here can prevent medicament mischanneling.

In some embodiments, the features and components described above are applicable to reusable injection pens (e.g., insulin pens, etc.). In some embodiments, each collar, cap, input connector, etc. could be applied to prevent incorrect dosing of drugs delivered by injection pens. For example, one unique cartridge, having a first set of unique features as described above could be used to deliver long-acting insulin to a patient via a mated injection pen. Another unique cartridge, with a second set of unique features as described above could be used to deliver fast-acting or ultra-rapid insulin analogs to a patient via a different mated injection pen. As a further example, these features can be used to differentiate between more and less concentrated insulin analogs (e.g. U100, U200, or U500 insulin analogs).

The medicament described above for any embodiment can include any suitable compound or drug for treating, regulating, controlling or addressing one or more conditions of the patient. While diabetes mellitus is a target, other conditions can be addressed as well (e.g., pancreatic misfunction). The medicament can include for example a regulating agent, such as insulin, for regulating the blood glucose levels in the patient and/or a counter-regulatory agent, such as glucose or glucagon, for more effective blood glucose regulation in certain circumstances. Other type of agents can be used as well.

In some embodiments, an infusion system for multiple medicaments involving various needle sites, connectors, tubes, and cartridges that ensure proper channeling of each medicament to the patient is provided. In some embodiments, the infusion system comprises an infusion pump. In some embodiments, the infusion system comprises an infusion pump with two or more pump chambers. In some embodiments, the infusion system comprises cartridges that can be filled at the point of care with different medicaments (or may be pre-filled with different medicaments). In some embodiments, the infusion system comprises connectors and tubing that connect the cartridges to the infusion pump in such a way as to prevent mischanneling or cross-channeling of medicaments. In some embodiments, each type of cartridge for each type of medicament has unique differentiating sizes, shapes, and/or geometrical features (either as an integral part of the cartridge or as a component attached or affixed to the cartridge) that allow for unique coupling with a type of connector that itself has unique differentiating features that engage corresponding features in the pump housing and only allow for insertion of the proper cartridge into the proper pump chamber within the infusion pump.

In some embodiments, the systems described above can be used for the delivery of single medicaments, or combinations of medicaments. For instance, in some embodiments, the infusion set can be used to deliver agent A (e.g., insulin), while the features of that infusion set would be incompatible with the medicament reservoir for agent B (e.g., glucagon). Alternatively, in some embodiments, the infusion set can be used to deliver agent B, while the features of that infusion set would be incompatible with the medicament reservoir for agent A. Additionally, in some embodiments, as described above, dual medicaments can be delivered without mischanneling (e.g., bi-hormonal delivery, dual drug delivery, etc.). As is apparent from the disclosure above, configurations for the delivery of a plurality of medicaments (e.g., two, three, four, or more) without mischanneling can be provided.

In some embodiments, methods of making the infusion systems disclosed herein are provided. In some embodiments, various needle sites, connectors, tubes, and cartridges that ensure proper channeling of each medicament to the patient are assembled. In some embodiments, the method comprises assembling an infusion system with an infusion pump. In some embodiments, the method comprises assembling an infusion system with a pump having two or more pump chambers. In some embodiments, the method comprises assembling an infusion system with connectors and tubing that connect the cartridges to the infusion pump in such a way as to prevent mischanneling or cross-channeling of medicaments. In some embodiments, each type of cartridge for each type of medicament is assembled to have unique differentiating sizes, shapes, and/or geometrical features (either as an integral part of the cartridge or as a component attached or affixed to the cartridge) that allow for unique coupling with a type of connector that itself has unique differentiating features that engage corresponding features in the pump housing and only allow for insertion of the proper cartridge into the proper pump chamber within the infusion pump.

In some embodiments, the pump can include a controller. In some embodiments, the controller includes a memory and one or more hardware processors. The memory can include a non-transitory, computer-readable medium capable of storing computer-executable instructions for the pump or infusion system. The executable instructions can correspond to the processes and functions described above. For example, the executable instructions can correspond to the detection sequence described above and/or other processes such as reading optical codes, operating valves, and/or providing indications as described elsewhere herein. In some embodiments, the executable instructions also include instructions for controlling hardware components of the pump, for example, the motor, scanners, etc. The executable instructions can be implemented in C, C++, JAVA, or any other suitable programming languages. In some embodiments, the controller can include electronic circuits, for example, application specific circuitry such as ASICs and FPGAs, where some or all of the portions of the executable instructions can be implemented using the electronic circuits.

In certain embodiments, the computer-readable medium storing computer-executable instructions, when executed by one or more hardware processors, cause the one or more hardware processors to perform one or more of the following: urge the drive nut forward with force that is insufficient to move a plunger of an medicament reservoir, detect when the drive nut has contacted the plunger, determine if the plunger is that of an appropriately or inappropriately placed medicament, increase the force applied to the drive nut to deliver the medicament where the medicament reservoir is appropriate to deliver the medicament, or decrease the force applied to the drive nut and/or stop and/or retract the drive nut where the medicament reservoir is inappropriately placed in the pump.

In certain embodiments, the computer-readable medium storing computer-executable instructions, when executed by one or more hardware processors, cause the one or more hardware processors to perform one or more of the following: receive information concerning the medicament reservoir that is present in the pump, compare the medicament reservoir to medicament settings on the pump assembly, indicate a deviation from or proximity to the medicament settings based at least in part on a comparison of the settings required for the medicament reservoir and the settings on the pump, and/or adjust the settings of the pump to match appropriate medicament settings based on the medicament reservoir that is present.

One or more of the settings of the infusion assembly or other information as described elsewhere herein can be stored as one or more executable program modules in the memory of the controller and/or on other types of non-transitory computer-readable storage media, and the system can interact with computing assets over a network or other communication link. In some embodiments, the system may have additional components or fewer components than described above. For example, the controller of the pump can communicate to a server or another computing device over the network.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software as discussed above with respect to controller.

What is claimed is:

1. An inlet connector set for delivering multiple medicaments to a patient, the inlet connector set comprising:
    a first inlet connector comprising:
    a tightening feature configured to affix the first inlet connector to a first receptacle of an infusion pump;
    a capture feature configured to engage a first medicament reservoir and to couple the first inlet connector to the first medicament reservoir;
    a needle recessed within the capture feature of the first inlet connector, the needle being configured to receive the first medicament from the first medicament reservoir; and
    a check valve configured to resist an unintended distribution of the first medicament from the first medicament reservoir; and
    a second inlet connector comprising:
    a tightening feature configured to affix the second inlet connector to a second receptacle of the infusion pump;
    a capture feature configured to engage a second medicament reservoir and to couple the second inlet connector to the second medicament reservoir; and
    a needle recessed within the capture feature of the second inlet connector, the needle being configured to receive the second medicament from the second medicament reservoir,
    wherein the first check valve is configured to allow the first medicament to flow from the first medicament reservoir in response to a first threshold fluid pressure being applied to the first medicament,
    and wherein the first threshold fluid pressure is greater than a gravitationally induced hydrostatic pressure caused by placing the first reservoir set above an infusion site of the patient.

2. The inlet connector set of claim 1, wherein the second inlet connector comprises a second check valve configured to resist unintended distribution of the second medicament from the second medicament reservoir.

3. The inlet connector set of claim 1, wherein the first medicament inlet connector comprises features configured to prevent coupling to the second medicament reservoir.

4. The inlet connector set of claim 3, wherein the second medicament inlet connector comprises features configured to prevent coupling to the first medicament reservoir.

5. The inlet connector set of claim 1, wherein the first threshold fluid pressure is a pressure induced by a lead screw of the infusion pump urging a plunger of the first medicament reservoir forward.

6. The inlet connector set of claim 1, wherein the first check valve is a membrane that deforms under pressure from the first medicament.

7. The inlet connector set of claim 1, wherein the first needle is recessed within the first inlet connector such that the first inlet connector is configured to reduce the chance that a user contacts the first needle as the first inlet connector is handled.

8. The inlet connector set of claim 7, wherein the second needle is recessed within the second inlet connector such that the second inlet connector is configured to reduce the chance that the user contacts the second needle as the second inlet connector is handled.

9. An infusion set comprising the connector set of claim 1 and further comprising a first infusion connector and a first fluid conduit, the first fluid conduit providing a first fluid path from the first inlet connector to the first infusion connector.

10. The infusion set of claim 9, further comprising a second infusion connector and a second fluid conduit, the second fluid conduit providing a second fluid path from the second inlet connector to the second infusion connector.

11. A medicament infusion system comprising the infusion set of claim 9 and an infusion base configured to receive the first infusion connector.

12. The medicament infusion system of claim 11, wherein the infusion base is configured to receive a second infusion connector.

13. The medicament infusion system of claim 11, further comprising the first and second medicament reservoirs.

14. An inlet connector set for delivering multiple medicaments to a patient, the inlet connector set comprising:
a first inlet connector comprising:
a tightening feature configured to affix the first inlet connector to a first receptacle of an infusion pump;
a capture feature configured to engage a first medicament reservoir and to couple the first inlet connector to the first medicament reservoir;
a needle recessed within the capture feature of the first inlet connector, the needle being configured to receive the first medicament from the first medicament reservoir; and
a first check valve configured to resist an unintended distribution of the first medicament from the first medicament reservoir; and a second inlet connector comprising:
a tightening feature configured to affix the second inlet connector to a second receptacle of the infusion pump;
a capture feature configured to engage a second medicament reservoir and to couple the second inlet connector to the second medicament reservoir;
a second check valve configured to resist unintended distribution of the second medicament from the second medicament reservoir; and
a needle recessed within the capture feature of the second inlet connector, the needle being configured to receive the second medicament from the second medicament reservoir;
wherein the first medicament inlet connector comprises features configured to prevent coupling to the second medicament reservoir,
wherein the first check valve is configured to allow the first medicament to flow from the first medicament reservoir in response to a first threshold fluid pressure being applied to the first medicament,
and wherein the first threshold fluid pressure is greater than a gravitationally induced hydrostatic pressure caused by placing the first reservoir set above an infusion site of the patient.

15. The inlet connector set of claim 14, wherein the first threshold fluid pressure is a pressure induced by a lead screw of the infusion pump urging a plunger of the first medicament reservoir forward.

16. The inlet connector set of claim 14, wherein the second check valve is configured to allow the second medicament to flow from the second medicament reservoir in response to a second threshold fluid pressure being applied to the second medicament and wherein the second threshold fluid pressure is greater than a gravitationally induced hydrostatic pressure caused by placing the second reservoir set above the infusion site of the patient.

* * * * *